US012600752B2

(12) United States Patent (10) Patent No.: US 12,600,752 B2
Baric et al. (45) Date of Patent: Apr. 14, 2026

(54) METHODS AND COMPOSITIONS FOR RECOMBINANT DENGUE VIRUSES OR VACCINE AND DIAGNOSTIC DEVELOPMENT

(71) Applicant: The University of North Carolina at Chapel Hill, Chapel Hill, NC (US)

(72) Inventors: Ralph Baric, Haw River, NC (US); Ellen Young, Hillsborough, NC (US); Jennifer Munt, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 1001 days.

(21) Appl. No.: 17/778,055

(22) PCT Filed: Nov. 20, 2020

(86) PCT No.: PCT/US2020/061661
§ 371 (c)(1),
(2) Date: May 19, 2022

(87) PCT Pub. No.: WO2021/102363
PCT Pub. Date: May 27, 2021

(65) Prior Publication Data
US 2023/0018080 A1 Jan. 19, 2023

Related U.S. Application Data

(60) Provisional application No. 62/938,133, filed on Nov. 20, 2019.

(51) Int. Cl.
*C07K 14/18* (2006.01)
*A61K 39/12* (2006.01)
*C12N 7/00* (2006.01)

(52) U.S. Cl.
CPC .......... *C07K 14/1825* (2013.01); *A61K 39/12* (2013.01); *C12N 7/00* (2013.01)

(58) Field of Classification Search
None
See application file for complete search history.

(56) References Cited

U.S. PATENT DOCUMENTS

| | | | |
|---|---|---|---|
| 4,501,729 A | 2/1985 | Boucher et al. | |
| 4,708,871 A | 11/1987 | Geysen | |
| 7,862,829 B2 | 1/2011 | Johnston et al. | |
| 8,691,961 B1 | 4/2014 | Puffer et al. | |
| 9,376,486 B2 | 6/2016 | Macary et al. | |
| 9,821,050 B2 * | 11/2017 | De Silva | G01N 33/56983 |
| 10,398,768 B2 | 9/2019 | Baric et al. | |
| 10,870,682 B2 * | 12/2020 | Messer | A61P 37/02 |

FOREIGN PATENT DOCUMENTS

| | | |
|---|---|---|
| WO | 9400153 A1 | 1/1994 |
| WO | 9517210 A1 | 6/1995 |
| WO | 9633739 A1 | 10/1996 |

OTHER PUBLICATIONS

Guzman, et al. Viruses. Dec. 2010;2(12):2649-62. doi: 10.3390/v2122649. Epub Dec. 8, 2010. (Year: 2010).*
Fahimi et al. "Dengue viruses and promising envelope protein domain III-based vaccines" Applied Microbiology and Biotechnology, 102:2977-2996 (2018).
International Search Report and the Written Opinion of the International Searching Authority corresponding to International Patent Application No. PCT/US2020/061661 (13 pages) (mailed Mar. 16, 2021).
Rajpoot et al. "Dengue envelope-based 'four-in-one' virus-like particles produced using Pichia pastoris induce enhancement-lacking, domain III-directed tetravalent neutralising antibodies in mice" Scientific Reports, 8(8643):1-14 (2018).
Andrade et al. "Analysis of Individuals from a Dengue-Endemic Region Helps Define the Footprint and Repertoire of Antibodies Targeting Dengue Virus 3 Type-Specific Epitopes" MBio, 8(5):e01205-17 (2017).
Gallichotte et al. "Epitope Addition and Ablation via Manipulation of a Dengue Virus Serotype 1 Infectious Clone" MSphere, 2(1):e00380-16 (2017).
Gallichotte et al. "Genetic Variation between Dengue Virus Type 4 Strains Impacts Human Antibody Binding and Neutralization" Cell Reports, 25:1214-1224 (2018).
Gallichotte et al. "Human dengue virus serotype 2 neutralizing antibodies target two distinct quaternary epitopes" PLoS Pathogens, 14:e1006934 (2018).
Gallichotte et al. "The Molecular Specificity of the Human Antibody Response to Dengue Virus Infections" Advances in Experimental Medicine and Biology, 1062:63-76 (2018).
GenBank® Database Accession No. DQ211652 "West Nile virus strain NY99, complete genome" www.ncbi.nlm.nih.gov (5 pages) (Jun. 7, 2006).
GenBank® Database Accession No. JX503529 "Yellow fever virus strain YF/Vaccine/USA/Sanofi-Pasteur-17D-204/JF795AA/YFVax, complete genome" www.ncbi.nlm.nih.gov (5 pages) (Sep. 16, 2012).
GenBank® Database Accession No. U14163 "Japanese encephalitis virus SA14 polyprotein mRNA, complete cds" www.ncbi.nlm.nih.gov (5 pages) (Sep. 13, 1994).
Geysen et al. "A Priori Delineation of a Peptide Which Mimics a Discontinuous Antigenic Determinant" Molecular Immunology, 23:709-715 (1986).
Geysen et al. "Use of peptide synthesis to probe viral antigens for epitopes to a resolution of a single amino acid" Proceedings of the National Academy of Sciences USA, 81:3998-4002 (1984).

(Continued)

*Primary Examiner* — Benjamin P Blumel
*Assistant Examiner* — Jeffrey Mark Sifford
(74) *Attorney, Agent, or Firm* — Myers Bigel, P.A.

(57) ABSTRACT

The present invention provides compositions and methods of use comprising a chimeric dengue virus E glycoprotein comprising a dengue virus E glycoprotein backbone, which comprises amino acid substitutions that may introduce an epitope that is recognized by an antibody from a dengue virus serotype that is different from the dengue virus serotype of the dengue virus E glycoprotein backbone.

31 Claims, 11 Drawing Sheets

Specification includes a Sequence Listing.

(56)                    References Cited

OTHER PUBLICATIONS

Hopp et al. "Prediction of protein antigenic determinants from amino acid sequences" Proceedings of the National Academy of Sciences USA, 78(6):3824-3828 (1981).

International Preliminary Report on Patentability corresponding to International Patent Application No. PCT/US2020/061661 (7 pages) (dated Jun. 2, 2022).

Kyte et al. "A Simple Method for Displaying the Hydropathic Character of a Protein" Journal of Molecular Biology, 157:105-132 (1982).

Meloen et al. "Mimotopes: realization of an unlikely concept" Journal of Molecular Recognition, 13:352-359 (2000).

Messer et al. "Functional Transplant of a Dengue Virus Serotype 3 (DENV3)-Specific Human Monoclonal Antibody Epitope into DENV1" Journal of Virology, 90(10):5090-5097 (2016).

Pal et al. "Immunization with the Chlamydia trachomatis major outer membrane protein, using adjuvants developed for human vaccines, can induce partial protection in a mouse model against a genital challenge" Vaccine, 24 (6):766-775 (2005).

Sabchareon et al. "Protective efficacy of the recombinant, live-attenuated, CYD tetravalent dengue vaccine in Thai schoolchildren: a randomised, controlled phase 2b trial" Lancet, 380:1559-1567 (2012).

Swanstrom et al. "Beyond Neutralizing Antibody Levels: The Epitope Specificity of Antibodies Induced by National Institutes of Health Monovalent Dengue Virus Vaccines" The Journal of Infectious Diseases, 220:219-222 (2019).

Tyle et al. "Iontophoretic Devices for Drug Delivery" Pharmaceutical Research, 3(6):318-326 (1986).

Widman et al. "Transplantation of a quaternary structure neutralizing antibody epitope from dengue virus serotype 3 into serotype 4" Scientific Reports, 7:17169 (2017).

Young et al. "Identification of Dengue Virus Serotype 3 Specific Antigenic Sites Targeted by Neutralizing Human Antibodies" Cell Host & Microbe, 27:710-724 (2020).

* cited by examiner

FIG. 1A                DENV3/1 A (23aa)
FIG. 1B                DENV3/1 B (23aa)
FIG. 1C                DENV 3/1 C (35aa)
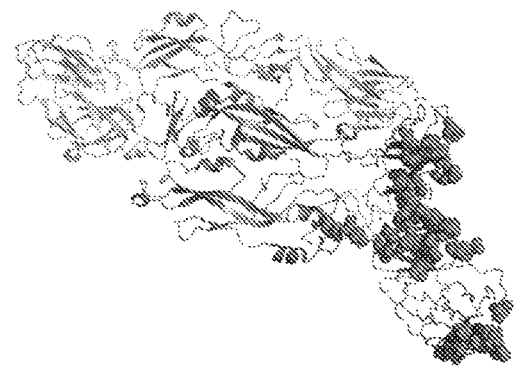
FIG. 1D                DENV 3/1 D (38aa)
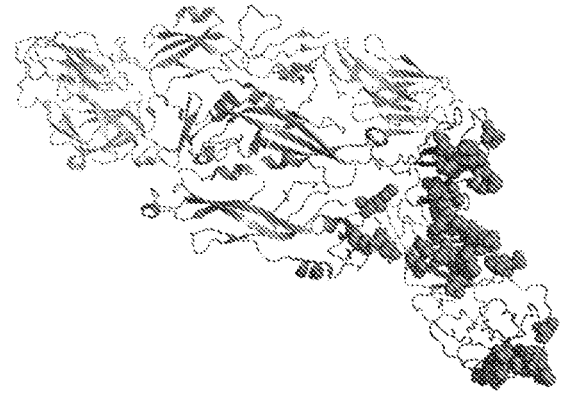

FIG. 1E               DENV3/1 B – 4 x $10^5$ ffu/ml
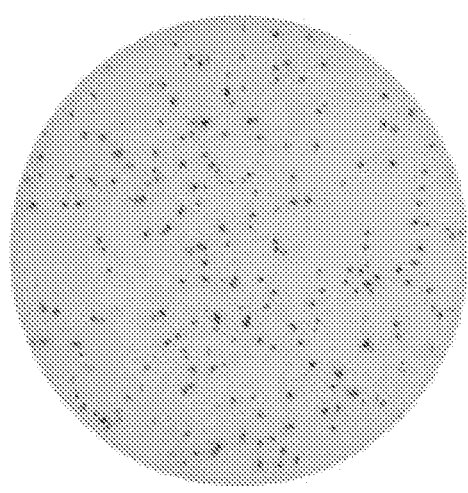
DENV 3/1 C – 1 x $10^6$ ffu/ml
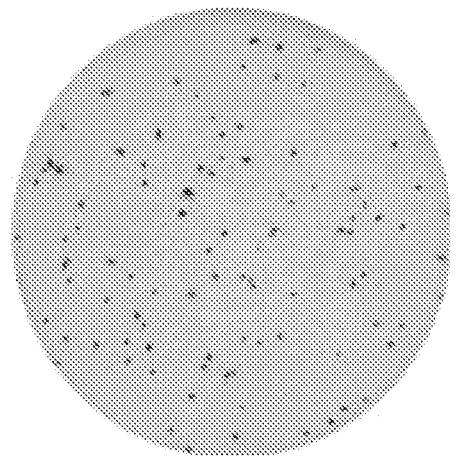
DENV 3/1 D – 3 x $10^6$ ffu/ml
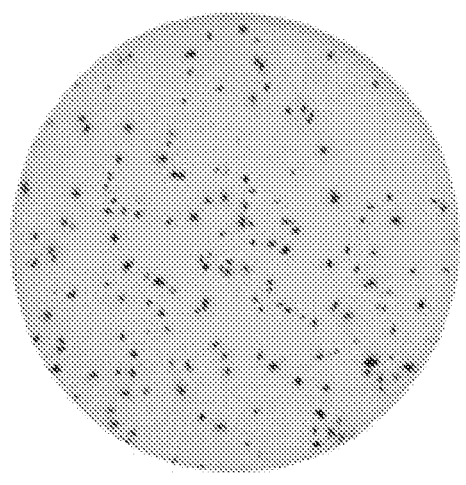

FIG. 1F

| | 46 | 50 | 52 | 53 | 55 | 138 | 141 | 156 | 157 | 158 | 160 | 161 | 163 | 169 | 171 | 173 | 174 | 176 | 177 | 180 |
|---|---|---|---|---|---|---|---|---|---|---|---|---|---|---|---|---|---|---|---|---|
| DENV3 ic | Q | A | Q | L | T | T | I | Q | - | V | T | E | S | T | A | I | P | E | T | A |
| DENV3/1 A | F | V | N | P | V | S | V | T | E | H | T | I | T | P | S | I | Q | T | D | A |
| DENV3/1 B | L | V | Q | P | V | S | | T | E | H | T | I | T | P | S | I | Q | T | D | A |
| DENV3/1 C | L | A | Q | L | T | S | V | T | E | H | T | I | T | P | S | I | Q | T | D | A |
| DENV3/1 D | L | A | N | P | V | S | V | T | E | H | T | I | T | P | S | I | Q | T | D | A |
| DENV1 ic | L | V | N | P | V | S | V | T | E | H | T | I | T | P | S | I | Q | T | D | A |
| Domain | I | | | | | II | | | | | | | | | | | | | | |

| | 182 | 184 | 272 | 275 | 277 | 293 | 304 | 305 | 307 | 325 | 327 | 329 | 377 | 380 | 382 | 384 | 385 | 389 | 390 |
|---|---|---|---|---|---|---|---|---|---|---|---|---|---|---|---|---|---|---|---|
| DENV3 ic | G | E | S | G | S | E | N | T | V | E | K | E | N | I | I | D | N | I | N |
| DENV3/1 A | G | E | T | T | E | T | N | E | V | E | K | E | N | I | I | D | N | I | N |
| DENV3/1 B | G | E | T | T | E | T | N | E | V | E | K | E | N | I | I | D | N | I | N |
| DENV3/1 C | T | D | T | T | G | S | K | K | E | T | Y | V | A | E | K | | | L | S |
| DENV3/1 D | T | D | T | T | G | S | K | K | E | T | Y | V | A | E | K | | | L | S |
| DENV1 ic | T | D | T | T | G | S | K | K | E | T | Y | V | A | E | K | | | L | S |
| Domain | II | | | | | | | | | | | | III | | | | | | |

FIG. 1G
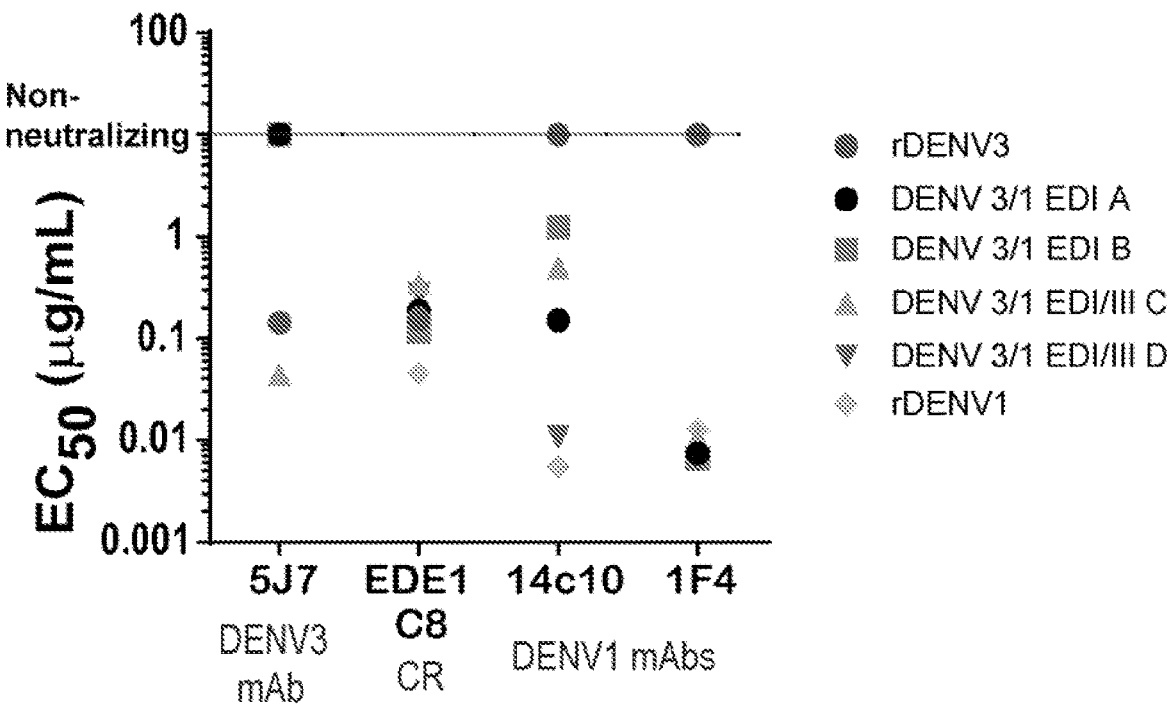
Legend:
- rDENV3
- DENV 3/1 EDI A
- DENV 3/1 EDI B
- DENV 3/1 EDI/III C
- DENV 3/1 EDI/III D
- rDENV1
FIG. 2A
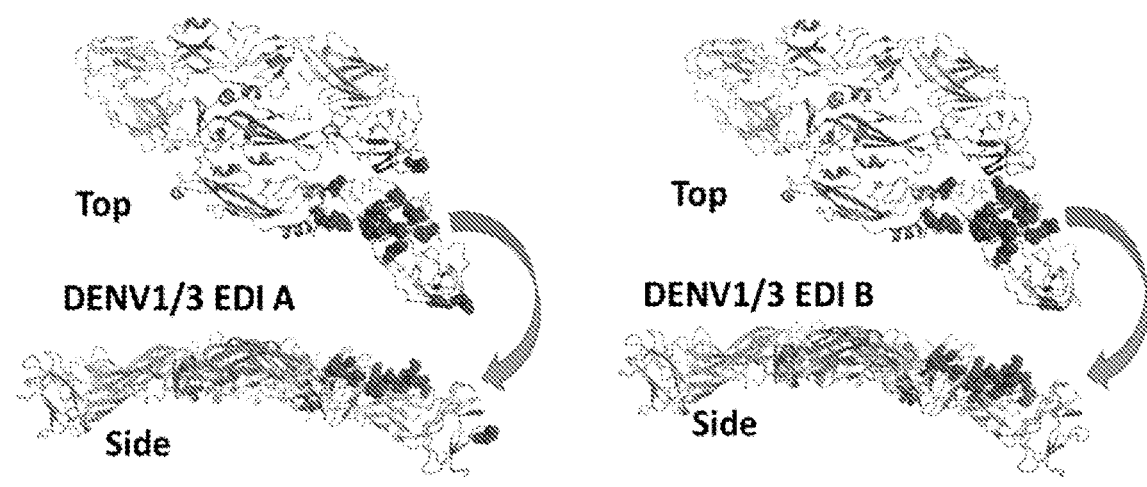
FIG. 2B

DENV1/3-A $1 \times 10^{5}$ ffu/ml

DENV1/3-B $1 \times 10^{6}$ ffu/ml

| | 46 | 52 | 138 | 141 | 156 | 157 | 158 | 160 | 161 | 163 | 169 | 171 | 173 | 174 | 176 | 177 | 180 | 182 | 184 | 272 | 275 | 277 | 293 | 384 | 385 |
|---|---|---|---|---|---|---|---|---|---|---|---|---|---|---|---|---|---|---|---|---|---|---|---|---|---|
| DENV1 ic | L | N | S | V | T | E | H | T | I | T | P | S | I | Q | T | D | A | T | D | T | T | T | E | E | K |
| DENV1/3 A | Q | Q | T | V | Q | S | H | V | T | E | P | T | A | I | P | E | A | T | D | N | G | S | T | D | N |
| DENV1/3 B | Q | N | T | I | Q | - | - | V | T | E | S | T | A | I | P | E | T | G | E | N | G | S | E | E | K |
| DENV3 ic | Q | Q | T | I | Q | - | - | V | T | E | S | T | A | I | P | E | T | G | E | N | G | S | E | D | N |
| domain | I | II | | | | | | | | | | | I | | | | | | | | | | | III | |

FIG. 3A

Indonesia GT I     Thailand GT II     Sri Lanka GT III     Puerto Rico GT IV

FIG. 3B

| DENV3 | Genotype | 6 | 22 | 50 | 62 | 63 | 68 | 81 | 113 | 120 | 124 | 132 | 139 | 154 | 160 | 169 | 171 | 172 | 224 | 226 | 231 | 270 | 301 | 302 | 303 | 322 | 329 | 380 | 383 | 386 |
|---|---|---|---|---|---|---|---|---|---|---|---|---|---|---|---|---|---|---|---|---|---|---|---|---|---|---|---|---|---|---|
| Sri Lanka 1989 | III | I | D | A | E | G | I | V | L | Q | P | Y | V | E | A | T | A | I | T | T | R | N | T | N | T | V | A | I | N | K |
| Indonesia 1982 | I | V | D | A | E | G | V | I | L | Q | S | H | V | E | A | V | A | I | T | T | K | T | L | N | A | V | A | I | K | K |
| Thailand 1995 | II | V | D | A | E | G | I | I | L | Q | P | H | V | D | V | V | A | I | T | T | R | N | L | N | T | V | A | I | K | K |
| Cuba 2002 | III | V | V | A | E | G | I | V | L | Q | P | Y | V | E | A | T | A | I | T | T | R | N | T | N | T | V | V | I | N | K |
| Puerto Rico 1977 | IV | V | E | V | G | A | T | T | S | H | L | H | I | E | A | A | V | T | A | V | R | I | S | G | T | I | A | T | K | R |
| domain | | | I | | | | II | | | | | | | | I | | | | II | | | | | III | | | | | III | | |

FIG. 4A                         Gain of function

FIG. 4B                         Loss of function

Gain-of-Function – DENV3 Puerto Rico backbone with Domain 1, 2 or 3 changed to Sri Lanka DENV3 G-III with G-IV EDI   DENV3 G-IV with G-III EDII   DENV3 G-IV with G-III EDIII

Loss-of-Function – DENV3 Sri Lanka backbone with Domain 1, 2 or 3 changed to Puerto Rico DENV3 G-III with G-IV EDI   DENV3 G-III with G-IV EDII   DENV3 G-III with G-IV EDIII

FIG. 5

| | 46 | 50 | 52 | 53 | 55 | 63 | 66 | 68 | 81 | 83 | 88 | 90 | 93 | 94 | 96 | 114 | 120 | 122 | 123 |
|---|---|---|---|---|---|---|---|---|---|---|---|---|---|---|---|---|---|---|---|
| DENV 1 | L | V | N | P | V | A | S | T | T | V | T | F | R | R | F | I | K | V | T |
| DENV 1/3-C | L | V | N | L | T | G | T | I | V | P | Q | Y | K | H | Y | V | Q | L | E |
| DENV 1/3-D | L | V | N | P | V | G | T | I | V | P | Q | Y | K | H | Y | V | Q | L | E |
| DENV 1/3-E | Q | A | Q | L | T | G | T | I | V | P | Q | Y | K | H | Y | V | Q | L | E |
| DENV 1/3-F | L | A | Q | L | T | G | T | I | V | P | Q | Y | K | H | Y | V | Q | L | E |
| DENV 3 | Q | A | Q | L | T | G | T | I | V | P | Q | Y | K | H | Y | V | Q | L | E |

| | 124 | 125 | 129 | 197 | 203 | 205 | 207 | 210 | 214 | 225 | 227 | 228 | 229 | 234 | 235 | 242 | 272 | 275 | 277 |
|---|---|---|---|---|---|---|---|---|---|---|---|---|---|---|---|---|---|---|---|
| DENV 1 | K | L | I | V | K | S | L | K | L | S | S | Q | E | Q | D | T | T | T | T |
| DENV 1/3-C | P | I | V | I | N | A | M | R | F | T | E | T | P | K | E | N | N | T | T |
| DENV 1/3-D | P | I | I | V | K | S | L | K | F | T | E | T | P | K | E | N | T | T | T |
| DENV 1/3-E | P | I | V | I | N | A | M | R | F | T | E | T | P | K | E | N | N | G | S |
| DENV 1/3-F | P | I | V | I | N | A | M | R | F | T | E | T | P | K | E | N | N | G | S |
| DENV 3 | P | I | V | I | N | A | M | R | F | T | E | T | P | K | E | N | N | G | S |

FIG. 6A

| | 300 | 304 | 305 | 307 | 309 | 320 | 322 | 323 | 325 | 327 | 329 | 339 | 340 | 342 | 343 | 345 | 346 | 347 | 357 | 360 | 363 | 377 | 380 | 382 | 384 | 385 | 389 | 390 |
|---|---|---|---|---|---|---|---|---|---|---|---|---|---|---|---|---|---|---|---|---|---|---|---|---|---|---|---|---|
| E pro DENV1 | V | G | S | K | E | V | V | Q | K | E | T | S | Q | E | K | V | T | Q | I | D | K | Y | V | A | E | K | L | S |
| E pro DV1-3 domain3 3aa remain DV1 | A | N | T | V | K | I | I | K | E | K | E | T | E | E | K | K | T | H | V | K | E | N | I | I | D | N | I | N |
| E pro DV1-3 domain3 2aa remain DV1 | A | N | T | V | K | I | I | K | E | K | E | T | E | E | K | K | A | H | V | K | E | N | I | I | D | N | I | N |
| E pro DV1-3 domain3 all DV3 | A | N | T | V | K | I | I | K | E | K | E | T | E | G | Q | K | A | H | V | K | E | N | I | I | D | N | I | N |
| E pro DENV3 | A | N | T | V | K | I | I | K | E | K | E | T | E | G | Q | K | A | H | V | K | E | N | I | I | D | N | I | N |

SEQUENCE LISTING

<160> NUMBER OF SEQ ID NOS: 17

<210> SEQ ID NO 1
<211> LENGTH: 493
<212> TYPE: PRT
<213> ORGANISM: Dengue virus type 3

<400> SEQUENCE: 1

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
            20                  25                  30

Thr Met Ala Lys Asn Lys Pro Thr Leu Asp Ile Glu Leu Gln Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Ile Leu Leu Thr Met Lys Asn Lys Ala Trp Met Val His Arg
        195                 200                 205

Gln Trp Phe Phe Asp Leu Pro Leu Pro Trp Thr Ser Gly Ala Thr Thr
    210                 215                 220
```

```
Glu Thr Pro Thr Trp Asn Arg Lys Glu Leu Leu Val Thr Phe Lys Asn
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Ala Met Cys Thr Asn Thr Phe
    290                 295                 300

Val Leu Lys Lys Glu Val Ser Glu Thr Gln His Gly Thr Ile Leu Ile
305                 310                 315                 320

Lys Val Glu Tyr Lys Gly Glu Asp Ala Pro Cys Lys Ile Pro Phe Ser
                325                 330                 335

Thr Glu Asp Gly Gln Gly Lys Ala His Asn Gly Arg Leu Ile Thr Ala
            340                 345                 350

Asn Pro Val Val Thr Lys Lys Glu Glu Pro Val Asn Ile Glu Ala Glu
        355                 360                 365

Pro Pro Phe Gly Glu Ser Asn Ile Val Ile Gly Ile Gly Asp Asn Ala
    370                 375                 380

Leu Lys Ile Asn Trp Tyr Lys Lys Gly Ser Ser Ile Gly Lys Met Phe
385                 390                 395                 400

Glu Ala Thr Ala Arg Gly Ala Arg Arg Met Ala Ile Leu Gly Asp Thr
                405                 410                 415

Ala Trp Asp Phe Gly Ser Val Gly Gly Val Leu Asn Ser Leu Gly Lys
            420                 425                 430

Met Val His Gln Ile Phe Gly Ser Ala Tyr Thr Ala Leu Phe Ser Gly
        435                 440                 445

Val Ser Trp Val Met Lys Ile Gly Ile Gly Val Leu Leu Thr Trp Ile
    450                 455                 460

Gly Leu Asn Ser Lys Asn Thr Ser Met Ser Phe Ser Cys Ile Ala Ile
465                 470                 475                 480

Gly Ile Ile Thr Leu Tyr Leu Gly Ala Val Val Gln Ala
                485                 490
```

```
<210> SEQ ID NO 2
<211> LENGTH: 495
<212> TYPE: PRT
<213> ORGANISM: Dengue virus type 1

<400> SEQUENCE: 2
```

```
Met Arg Cys Val Gly Ile Gly Asn Arg Asp Phe Val Glu Gly Leu Ser
1                   5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110
```

-continued

```
Leu Ile Thr Cys Ala Lys Phe Lys Cys Val Thr Lys Leu Glu Gly Lys
        115                 120                 125

Ile Val Gln Tyr Glu Asn Leu Lys Tyr Ser Val Ile Val Thr Val His
        130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Val Leu Leu Thr Met Lys Lys Lys Ser Trp Leu Val
        195                 200                 205

His Lys Gln Trp Phe Leu Asp Leu Pro Leu Pro Trp Thr Ser Gly Ala
        210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Val Met Cys Thr Gly
        290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
                340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
        370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
        435                 440                 445

Ser Gly Val Ser Trp Thr Met Lys Ile Gly Ile Gly Ile Leu Leu Thr
        450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495
```

<210> SEQ ID NO 3
<211> LENGTH: 493
<212> TYPE: PRT
<213> ORGANISM: Artificial
<220> FEATURE:

<223> OTHER INFORMATION: DENV3/1 chimera B

<400> SEQUENCE: 3

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Leu Lys Thr
            35                  40                  45

Glu Val Thr Gln Pro Ala Val Leu Arg Lys Leu Cys Ile Glu Gly Lys
        50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Ser Val Ile Ile Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Gly Leu Glu Cys Ser Pro Arg Thr Gly Leu Asp
            180                 185                 190

Phe Asn Glu Met Ile Leu Leu Thr Met Lys Asn Lys Ala Trp Met Val
            195                 200                 205

His Arg Gln Trp Phe Phe Asp Leu Pro Leu Pro Trp Thr Ser Gly Ala
        210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Glu Leu Lys Gly Met Ser Tyr Ala Met Cys Thr Asn
    290                 295                 300

Thr Phe Val Leu Lys Lys Glu Val Ser Glu Thr Gln His Gly Thr Ile
305                 310                 315                 320

Leu Ile Lys Val Glu Tyr Lys Gly Glu Asp Ala Pro Cys Lys Ile Pro
                325                 330                 335

Phe Ser Thr Glu Asp Gly Gln Gly Lys Ala His Asn Gly Arg Leu Ile
            340                 345                 350

Thr Ala Asn Pro Val Val Thr Lys Lys Glu Glu Pro Val Asn Ile Glu
        355                 360                 365

Ala Glu Pro Pro Phe Gly Glu Ser Asn Ile Val Ile Gly Ile Gly Glu
    370                 375                 380

Lys Ala Leu Lys Ile Asn Trp Tyr Lys Lys Gly Ser Ser Ile Gly Lys
385                 390                 395                 400
```

-continued

Met Phe Glu Ala Thr Ala Arg Gly Ala Arg Arg Met Ala Ile Leu Gly
                405                     410                     415

Asp Thr Ala Trp Asp Phe Gly Ser Val Gly Gly Val Leu Asn Ser Leu
                420                     425                     430

Gly Lys Met Val His Gln Ile Phe Gly Ser Ala Tyr Thr Ala Leu Phe
                435                     440                     445

Ser Gly Val Ser Trp Val Met Lys Ile Gly Ile Gly Val Leu Leu Thr
        450                     455                     460

Trp Ile Gly Leu Asn Ser Lys Asn Thr Ser Met Ser Phe Ser Cys Ile
465                     470                     475                     480

Ala Ile Gly Ile Ile Thr Leu Tyr Leu Gly Ala Val Val
                485                     490

<210> SEQ ID NO 4
<211> LENGTH: 493
<212> TYPE: PRT
<213> ORGANISM: Artificial
<220> FEATURE:
<223> OTHER INFORMATION: DENv3/1 chimera C

<400> SEQUENCE: 4

Met Arg Cys Val Gly Ile Gly Asn Arg Asp Phe Val Glu Gly Leu Ser
1                       5                       10                      15

Gly Ala Thr Trp Val Asp Val Val Leu Glu His Gly Gly Cys Val Thr
                20                      25                      30

Thr Met Ala Lys Asn Lys Pro Thr Leu Asp Ile Glu Leu Leu Lys Thr
                35                      40                      45

Glu Ala Thr Gln Leu Ala Thr Leu Arg Lys Leu Cys Ile Glu Gly Lys
        50                      55                      60

Ile Thr Asn Ile Thr Thr Asp Ser Arg Cys Pro Thr Gln Gly Glu Ala
65                      70                      75                      80

Val Leu Pro Glu Glu Gln Asp Gln Asn Tyr Val Cys Lys His Thr Tyr
                85                      90                      95

Val Asp Arg Gly Trp Gly Asn Gly Cys Gly Leu Phe Gly Lys Gly Ser
                100                     105                     110

Leu Val Thr Cys Ala Lys Phe Gln Cys Leu Glu Pro Ile Glu Gly Lys
                115                     120                     125

Val Val Gln Tyr Glu Asn Leu Lys Tyr Ser Val Ile Val Thr Val His
        130                     135                     140

Thr Gly Asp Gln His Gln Val Gly Asn Glu Thr Thr Glu His Gly Thr
145                     150                     155                     160

Ile Ala Thr Ile Thr Pro Gln Ala Pro Thr Ser Glu Ile Gln Leu Thr
                165                     170                     175

Asp Tyr Gly Ala Leu Thr Leu Asp Cys Ser Pro Arg Thr Gly Leu Asp
                180                     185                     190

Phe Asn Glu Met Ile Leu Leu Thr Met Lys Asn Lys Ala Trp Met Val
                195                     200                     205

His Arg Gln Trp Phe Phe Asp Leu Pro Leu Pro Trp Thr Ser Gly Ala
        210                     215                     220

Thr Thr Glu Thr Pro Thr Trp Asn Arg Lys Glu Leu Leu Val Thr Phe
225                     230                     235                     240

Lys Asn Ala His Ala Lys Lys Gln Glu Val Val Val Leu Gly Ser Gln
                245                     250                     255

Glu Gly Ala Met His Thr Ala Leu Thr Gly Ala Thr Glu Ile Gln Thr
                260                     265                     270

-continued

```
Ser Gly Thr Thr Thr Ile Phe Ala Gly His Leu Lys Cys Arg Leu Lys
        275                 280                 285

Met Asp Lys Leu Thr Leu Lys Gly Met Ser Tyr Ala Met Cys Thr Gly
    290                 295                 300

Ser Phe Lys Leu Lys Lys Glu Val Ser Glu Thr Gln His Gly Thr Ile
305                 310                 315                 320

Leu Ile Lys Val Lys Tyr Glu Gly Thr Asp Ala Pro Cys Lys Ile Pro
                325                 330                 335

Phe Ser Thr Glu Asp Gly Gln Gly Lys Ala His Asn Gly Arg Leu Ile
            340                 345                 350

Thr Ala Asn Pro Val Val Thr Lys Lys Glu Glu Pro Val Asn Ile Glu
            355                 360                 365

Ala Glu Pro Pro Phe Gly Glu Ser Tyr Ile Val Val Gly Ala Gly Glu
    370                 375                 380

Lys Ala Leu Lys Leu Ser Trp Tyr Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Val Gly Gly Val Leu Asn Ser Leu
            420                 425                 430

Gly Lys Met Val His Gln Ile Phe Gly Ser Ala Tyr Thr Ala Leu Phe
            435                 440                 445

Ser Gly Val Ser Trp Val Met Lys Ile Gly Ile Gly Val Leu Leu Thr
    450                 455                 460

Trp Ile Gly Leu Asn Ser Lys Asn Thr Ser Met Ser Phe Ser Cys Ile
465                 470                 475                 480

Ala Ile Gly Ile Ile Thr Leu Tyr Leu Gly Ala Val Val
                485                 490
```

```
<210> SEQ ID NO 5
<211> LENGTH: 493
<212> TYPE: PRT
<213> ORGANISM: Artificial
<220> FEATURE:
<223> OTHER INFORMATION: DENV3/1 chimera D

<400> SEQUENCE: 5

Met Arg Cys Val Gly Ile Gly Asn Arg Asp Phe Val Glu Gly Leu Ser
1               5                   10                  15

Gly Ala Thr Trp Val Asp Val Val Leu Glu His Gly Gly Cys Val Thr
                20                  25                  30

Thr Met Ala Lys Asn Lys Pro Thr Leu Asp Ile Glu Leu Leu Lys Thr
            35                  40                  45

Glu Ala Thr Asn Pro Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Ser Val Ile Val Thr Val His
    130                 135                 140
```

-continued

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Ile Leu Leu Thr Met Lys Asn Lys Ala Trp Met Val
        195                 200                 205

His Arg Gln Trp Phe Phe Asp Leu Pro Leu Pro Trp Thr Ser Gly Ala
    210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
        275                 280                 285

Met Asp Lys Leu Thr Leu Lys Gly Met Ser Tyr Ala Met Cys Thr Gly
    290                 295                 300

Ser Phe Lys Leu Lys Lys Glu Val Ser Glu Thr Gln His Gly Thr Ile
305                 310                 315                 320

Leu Ile Lys Val Lys Tyr Glu Gly Thr Asp Ala Pro Cys Lys Ile Pro
                325                 330                 335

Phe Ser Thr Glu Asp Gly Gln Gly Lys Ala His Asn Gly Arg Leu Ile
            340                 345                 350

Thr Ala Asn Pro Val Val Thr Lys Lys Glu Glu Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Tyr Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Val Gly Gly Val Leu Asn Ser Leu
            420                 425                 430

Gly Lys Met Val His Gln Ile Phe Gly Ser Ala Tyr Thr Ala Leu Phe
        435                 440                 445

Ser Gly Val Ser Trp Val Met Lys Ile Gly Ile Gly Val Leu Leu Thr
    450                 455                 460

Trp Ile Gly Leu Asn Ser Lys Asn Thr Ser Met Ser Phe Ser Cys Ile
465                 470                 475                 480

Ala Ile Gly Ile Ile Thr Leu Tyr Leu Gly Ala Val Val
                485                 490

<210> SEQ ID NO 6
<211> LENGTH: 495
<212> TYPE: PRT
<213> ORGANISM: Artificial
<220> FEATURE:
<223> OTHER INFORMATION: DENV1/3 chimera A

<400> SEQUENCE: 6

Met Arg Cys Val Gly Ile Gly Asn Arg Asp Phe Val Glu Gly Leu Ser
1                   5                   10                  15

-continued

```
Gly Ala Thr Trp Val Asp Val Val Leu Glu His Gly Ser Cys Val Thr
            20              25              30

Thr Met Ala Lys Asp Lys Pro Thr Leu Asp Ile Glu Leu Gln Lys Thr
            35              40              45

Glu Val Thr Gln Pro Ala Val Leu Arg Lys Leu Cys Ile Glu Ala Lys
        50              55              60

Ile Ser Asn Thr Thr Thr Asp Ser Arg Cys Pro Thr Gln Gly Glu Ala
65              70              75              80

Thr Leu Val Glu Glu Gln Asp Thr Asn Phe Val Cys Arg Arg Thr Phe
            85              90              95

Val Asp Arg Gly Trp Gly Asn Gly Cys Gly Leu Phe Gly Lys Gly Ser
        100             105             110

Leu Ile Thr Cys Ala Lys Phe Lys Cys Val Thr Lys Leu Glu Gly Lys
        115             120             125

Ile Val Gln Tyr Glu Asn Leu Lys Tyr Thr Val Ile Val Thr Val His
        130             135             140

Thr Gly Asp Gln His Gln Val Gly Asn Glu Thr Gln Ser His Gly Val
145             150             155             160

Thr Ala Glu Ile Thr Pro Gln Ala Pro Thr Thr Glu Ala Ile Leu Pro
                165             170             175

Glu Tyr Gly Ala Leu Thr Leu Asp Cys Ser Pro Arg Thr Gly Leu Asp
            180             185             190

Phe Asn Glu Met Val Leu Leu Thr Met Lys Lys Lys Ser Trp Leu Val
            195             200             205

His Lys Gln Trp Phe Leu Asp Leu Pro Leu Pro Trp Thr Ser Gly Ala
        210             215             220

Ser Thr Ser Gln Glu Thr Trp Asn Arg Gln Asp Leu Leu Val Thr Phe
225             230             235             240

Lys Thr Ala His Ala Lys Lys Gln Glu Val Val Val Leu Gly Ser Gln
                245             250             255

Glu Gly Ala Met His Thr Ala Leu Thr Gly Ala Thr Glu Ile Gln Asn
            260             265             270

Ser Gly Gly Thr Ser Ile Phe Ala Gly His Leu Lys Cys Arg Leu Lys
        275             280             285

Met Asp Lys Leu Thr Leu Lys Gly Met Ser Tyr Val Met Cys Thr Gly
        290             295             300

Ser Phe Lys Leu Glu Lys Glu Val Ala Glu Thr Gln His Gly Thr Val
305             310             315             320

Leu Val Gln Val Lys Tyr Glu Gly Thr Asp Ala Pro Cys Lys Ile Pro
                325             330             335

Phe Ser Ser Gln Asp Glu Lys Gly Val Thr Gln Asn Gly Arg Leu Ile
            340             345             350

Thr Ala Asn Pro Ile Val Thr Asp Lys Glu Lys Pro Val Asn Ile Glu
            355             360             365

Ala Glu Pro Pro Phe Gly Glu Ser Tyr Ile Val Val Gly Ala Gly Asp
        370             375             380

Asn Ala Leu Lys Leu Ser Trp Phe Lys Lys Gly Ser Ser Ile Gly Lys
385             390             395             400

Met Phe Glu Ala Thr Ala Arg Gly Ala Arg Arg Met Ala Ile Leu Gly
                405             410             415

Asp Thr Ala Trp Asp Phe Gly Ser Ile Gly Gly Val Phe Thr Ser Val
            420             425             430

Gly Lys Leu Ile His Gln Ile Phe Gly Thr Ala Tyr Gly Val Leu Phe
```

-continued

```
              435                 440                 445
Ser Gly Val Ser Trp Thr Met Lys Ile Gly Ile Gly Ile Leu Leu Thr
        450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 7
<211> LENGTH: 493
<212> TYPE: PRT
<213> ORGANISM: Artificial
<220> FEATURE:
<223> OTHER INFORMATION: DENV1/3 chimera B

<400> SEQUENCE: 7

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Gln Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
        115                 120                 125

Ile Val Gln Tyr Glu Asn Leu Lys Tyr Thr Val Ile Ile Thr Val His
    130                 135                 140

Thr Gly Asp Gln His Gln Val Gly Asn Glu Thr Gln Gly Val Thr Ala
145                 150                 155                 160

Glu Ile Thr Pro Gln Ala Ser Thr Thr Glu Ala Ile Leu Pro Glu Tyr
                165                 170                 175

Gly Thr Leu Gly Leu Glu Cys Ser Pro Arg Thr Gly Leu Asp Phe Asn
            180                 185                 190

Glu Met Val Leu Leu Thr Met Lys Lys Lys Ser Trp Leu Val His Lys
        195                 200                 205

Gln Trp Phe Leu Asp Leu Pro Leu Pro Trp Thr Ser Gly Ala Ser Thr
    210                 215                 220

Ser Gln Glu Thr Trp Asn Arg Gln Asp Leu Leu Val Thr Phe Lys Thr
225                 230                 235                 240

Ala His Ala Lys Lys Gln Glu Val Val Val Leu Gly Ser Gln Glu Gly
                245                 250                 255

Ala Met His Thr Ala Leu Thr Gly Ala Thr Glu Ile Gln Asn Ser Gly
            260                 265                 270

Gly Thr Ser Ile Phe Ala Gly His Leu Lys Cys Arg Leu Lys Met Asp
        275                 280                 285

Lys Leu Glu Leu Lys Gly Met Ser Tyr Val Met Cys Thr Gly Ser Phe
    290                 295                 300

Lys Leu Glu Lys Glu Val Ala Glu Thr Gln His Gly Thr Val Leu Val
```

-continued

```
305                  310                  315                  320

Gln Val Lys Tyr Glu Gly Thr Asp Ala Pro Cys Lys Ile Pro Phe Ser
                 325                  330                  335

Ser Gln Asp Glu Lys Gly Val Thr Gln Asn Gly Arg Leu Ile Thr Ala
                 340                  345                  350

Asn Pro Ile Val Thr Asp Lys Glu Lys Pro Val Asn Ile Glu Ala Glu
                 355                  360                  365

Pro Pro Phe Gly Glu Ser Tyr Ile Val Val Gly Ala Gly Glu Lys Ala
                 370                  375                  380

Leu Lys Leu Ser Trp Phe Lys Lys Gly Ser Ser Ile Gly Lys Met Phe
385                  390                  395                  400

Glu Ala Thr Ala Arg Gly Ala Arg Arg Met Ala Ile Leu Gly Asp Thr
                 405                  410                  415

Ala Trp Asp Phe Gly Ser Ile Gly Gly Val Phe Thr Ser Val Gly Lys
                 420                  425                  430

Leu Ile His Gln Ile Phe Gly Thr Ala Tyr Gly Val Leu Phe Ser Gly
                 435                  440                  445

Val Ser Trp Thr Met Lys Ile Gly Ile Gly Ile Leu Leu Thr Trp Leu
                 450                  455                  460

Gly Leu Asn Ser Arg Ser Thr Ser Leu Ser Met Thr Cys Ile Ala Val
465                  470                  475                  480

Gly Met Val Thr Leu Tyr Leu Gly Val Met Val Gln Ala
                 485                  490
```

```
<210> SEQ ID NO 8
<211> LENGTH: 495
<212> TYPE: PRT
<213> ORGANISM: Artificial
<220> FEATURE:
<223> OTHER INFORMATION: DENV1/3 chimera C

<400> SEQUENCE: 8

Met Arg Cys Val Gly Ile Gly Asn Arg Asp Phe Val Glu Gly Leu Ser
1                    5                   10                   15

Gly Ala Thr Trp Val Asp Val Val Leu Glu His Gly Ser Cys Val Thr
                 20                   25                   30

Thr Met Ala Lys Asp Lys Pro Thr Leu Asp Ile Glu Leu Leu Lys Thr
                 35                   40                   45

Glu Val Thr Asn Leu Ala Thr Leu Arg Lys Leu Cys Ile Glu Gly Lys
                 50                   55                   60

Ile Thr Asn Ile Thr Thr Asp Ser Arg Cys Pro Thr Gln Gly Glu Ala
65                   70                   75                   80

Val Leu Pro Glu Glu Gln Asp Gln Asn Tyr Val Cys Lys His Thr Tyr
                 85                   90                   95

Val Asp Arg Gly Trp Gly Asn Gly Cys Gly Leu Phe Gly Lys Gly Ser
                 100                  105                  110

Leu Val Thr Cys Ala Lys Phe Gln Cys Leu Glu Pro Ile Glu Gly Lys
                 115                  120                  125

Val Val Gln Tyr Glu Asn Leu Lys Tyr Ser Val Ile Val Thr Val His
                 130                  135                  140

Thr Gly Asp Gln His Gln Val Gly Asn Glu Thr Thr Glu His Gly Thr
145                  150                  155                  160

Ile Ala Thr Ile Thr Pro Gln Ala Pro Thr Ser Glu Ile Gln Leu Thr
                 165                  170                  175

Asp Tyr Gly Ala Leu Thr Leu Asp Cys Ser Pro Arg Thr Gly Leu Asp
```

-continued

```
              180              185              190

Phe Asn Glu Met Ile Leu Leu Thr Met Lys Asn Lys Ala Trp Met Val
         195              200              205

His Arg Gln Trp Phe Phe Asp Leu Pro Leu Pro Trp Thr Ser Gly Ala
    210              215              220

Thr Thr Glu Thr Pro Thr Trp Asn Arg Lys Glu Leu Leu Val Thr Phe
225              230              235              240

Lys Asn Ala His Ala Lys Lys Gln Glu Val Val Val Leu Gly Ser Gln
         245              250              255

Glu Gly Ala Met His Thr Ala Leu Thr Gly Ala Thr Glu Ile Gln Asn
         260              265              270

Ser Gly Thr Thr Thr Ile Phe Ala Gly His Leu Lys Cys Arg Leu Lys
         275              280              285

Met Asp Lys Leu Thr Leu Lys Gly Met Ser Tyr Val Met Cys Thr Gly
    290              295              300

Ser Phe Lys Leu Glu Lys Glu Val Ala Glu Thr Gln His Gly Thr Val
305              310              315              320

Leu Val Gln Val Lys Tyr Glu Gly Thr Asp Ala Pro Cys Lys Ile Pro
         325              330              335

Phe Ser Ser Gln Asp Glu Lys Gly Val Thr Gln Asn Gly Arg Leu Ile
         340              345              350

Thr Ala Asn Pro Ile Val Thr Asp Lys Glu Lys Pro Val Asn Ile Glu
         355              360              365

Ala Glu Pro Pro Phe Gly Glu Ser Tyr Ile Val Val Gly Ala Gly Glu
    370              375              380

Lys Ala Leu Lys Leu Ser Trp Phe Lys Lys Gly Ser Ser Ile Gly Lys
385              390              395              400

Met Phe Glu Ala Thr Ala Arg Gly Ala Arg Arg Met Ala Ile Leu Gly
         405              410              415

Asp Thr Ala Trp Asp Phe Gly Ser Ile Gly Gly Val Phe Thr Ser Val
         420              425              430

Gly Lys Leu Ile His Gln Ile Phe Gly Thr Ala Tyr Gly Val Leu Phe
         435              440              445

Ser Gly Val Ser Trp Thr Met Lys Ile Gly Ile Gly Ile Leu Leu Thr
    450              455              460

Trp Leu Gly Leu Asn Ser Arg Ser Thr Ser Leu Ser Met Thr Cys Ile
465              470              475              480

Ala Val Gly Met Val Thr Leu Tyr Leu Gly Val Met Val Gln Ala
         485              490              495
```

```
<210> SEQ ID NO 9
<211> LENGTH: 495
<212> TYPE: PRT
<213> ORGANISM: Artificial
<220> FEATURE:
<223> OTHER INFORMATION: DENV1/3 chimera D

<400> SEQUENCE: 9

Met Arg Cys Val Gly Ile Gly Asn Arg Asp Phe Val Glu Gly Leu Ser
1               5               10              15

Gly Ala Thr Trp Val Asp Val Val Leu Glu His Gly Ser Cys Val Thr
         20              25              30

Thr Met Ala Lys Asp Lys Pro Thr Leu Asp Ile Glu Leu Leu Lys Thr
         35              40              45

Glu Val Thr Asn Pro Ala Val Leu Arg Lys Leu Cys Ile Glu Gly Lys
```

```
             50                    55                    60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
            115                 120                 125

Ile Val Gln Tyr Glu Asn Leu Lys Tyr Ser Val Ile Val Thr Val His
            130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
                180                 185                 190

Phe Asn Glu Met Val Leu Leu Thr Met Lys Lys Lys Ser Trp Leu Val
            195                 200                 205

His Lys Gln Trp Phe Phe Asp Leu Pro Leu Pro Trp Thr Ser Gly Ala
            210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Thr
                260                 265                 270

Ser Gly Thr Thr Thr Ile Phe Ala Gly His Leu Lys Cys Arg Leu Lys
            275                 280                 285

Met Asp Lys Leu Thr Leu Lys Gly Met Ser Tyr Val Met Cys Thr Gly
            290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Val Gly Ala Gly Glu
            370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
            450                 455                 460

Trp Leu Gly Leu Asn Ser Arg Ser Thr Ser Leu Ser Met Thr Cys Ile
465                 470                 475                 480
```

Ala Val Gly Met Val Thr Leu Tyr Leu Gly Val Met Val Gln Ala
                485                 490                 495

<210> SEQ ID NO 10
<211> LENGTH: 495
<212> TYPE: PRT
<213> ORGANISM: Artificial
<220> FEATURE:
<223> OTHER INFORMATION: DENV1/3 chimera E

<400> SEQUENCE: 10

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Gln Lys Thr
            35                  40                  45

Glu Ala Thr Gln Leu Ala Thr Leu Arg Lys Leu Cys Ile Glu Gly Lys
        50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
            115                 120                 125

Val Val Gln Tyr Glu Asn Leu Lys Tyr Ser Val Ile Val Thr Val His
        130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Ile Leu Leu Thr Met Lys Asn Lys Ala Trp Met Val
            195                 200                 205

His Arg Gln Trp Phe Phe Asp Leu Pro Leu Pro Trp Thr Ser Gly Ala
        210                 215                 220

Thr Thr Glu Thr Pro Thr Trp Asn Arg Lys Glu Leu Leu Val Thr Phe
225                 230                 235                 240

Lys Asn Ala His Ala Lys Lys Gln Glu Val Val Val Leu Gly Ser Gln
                245                 250                 255

Glu Gly Ala Met His Thr Ala Leu Thr Gly Ala Thr Glu Ile Gln Asn
            260                 265                 270

Ser Gly Gly Thr Ser Ile Phe Ala Gly His Leu Lys Cys Arg Leu Lys
            275                 280                 285

Met Asp Lys Leu Thr Leu Lys Gly Met Ser Tyr Val Met Cys Thr Gly
        290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
        355                 360                 365

Ala Glu Pro Pro Phe Gly Glu Ser Tyr Ile Val Val Gly Ala Gly Glu
    370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
                435                 440                 445

Ser Gly Val Ser Trp Thr Met Lys Ile Gly Ile Gly Ile Leu Leu Thr
    450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495

<210> SEQ ID NO 11
<211> LENGTH: 495
<212> TYPE: PRT
<213> ORGANISM: Artificial
<220> FEATURE:
<223> OTHER INFORMATION: DENV1/3 chimera F

<400> SEQUENCE: 11

Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
        35                  40                  45

Glu Ala Thr Gln Leu Ala Thr Leu Arg Lys Leu Cys Ile Glu Gly Lys
    50                  55                  60

Ile Thr Asn Ile Thr Thr Asp Ser Arg Cys Pro Thr Gln Gly Glu Ala
65                  70                  75                  80

Val Leu Pro Glu Glu Gln Asp Gln Asn Tyr Val Cys Lys His Thr Tyr
                85                  90                  95

Val Asp Arg Gly Trp Gly Asn Gly Cys Gly Leu Phe Gly Lys Gly Ser
            100                 105                 110

Leu Val Thr Cys Ala Lys Phe Gln Cys Leu Glu Pro Ile Glu Gly Lys
        115                 120                 125

Val Val Gln Tyr Glu Asn Leu Lys Tyr Ser Val Ile Val Thr Val His
    130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Ile Leu Leu Thr Met Lys Asn Lys Ala Trp Met Val
        195                 200                 205

His Arg Gln Trp Phe Phe Asp Leu Pro Leu Pro Trp Thr Ser Gly Ala
    210                 215                 220

-continued

```
Thr Thr Glu Thr Pro Thr Trp Asn Arg Lys Glu Leu Leu Val Thr Phe
225                 230                 235                 240

Lys Asn Ala His Ala Lys Lys Gln Glu Val Val Leu Gly Ser Gln
                245                 250                 255

Glu Gly Ala Met His Thr Ala Leu Thr Gly Ala Thr Glu Ile Gln Asn
                260                 265                 270

Ser Gly Gly Thr Ser Ile Phe Ala Gly His Leu Lys Cys Arg Leu Lys
            275                 280                 285

Met Asp Lys Leu Thr Leu Lys Gly Met Ser Tyr Val Met Cys Thr Gly
        290                 295                 300

Ser Phe Lys Leu Glu Lys Glu Val Ala Glu Thr Gln His Gly Thr Val
305                 310                 315                 320

Leu Val Gln Val Lys Tyr Glu Gly Thr Asp Ala Pro Cys Lys Ile Pro
                325                 330                 335

Phe Ser Ser Gln Asp Glu Lys Gly Val Thr Gln Asn Gly Arg Leu Ile
            340                 345                 350

Thr Ala Asn Pro Ile Val Thr Asp Lys Glu Lys Pro Val Asn Ile Glu
            355                 360                 365

Ala Glu Pro Pro Phe Gly Glu Ser Tyr Ile Val Val Gly Ala Gly Glu
        370                 375                 380

Lys Ala Leu Lys Leu Ser Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
        450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495
```

```
<210> SEQ ID NO 12
<211> LENGTH: 495
<212> TYPE: PRT
<213> ORGANISM: Artificial
<220> FEATURE:
<223> OTHER INFORMATION: DENV1/3 chimera

<400> SEQUENCE: 12
```

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
                20                  25                  30

Thr Met Ala Lys Asp Lys Pro Thr Leu Asp Ile Glu Leu Leu Lys Thr
            35                  40                  45

Glu Val Thr Asn Pro Ala Val Leu Arg Lys Leu Cys Ile Glu Ala Lys
        50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95
```

```
Val Asp Arg Gly Trp Gly Asn Gly Cys Gly Leu Phe Gly Lys Gly Ser
              100             105             110

Leu Ile Thr Cys Ala Lys Phe Lys Cys Val Thr Lys Leu Glu Gly Lys
              115             120             125

Ile Val Gln Tyr Glu Asn Leu Lys Tyr Ser Val Ile Val Thr Val His
              130             135             140

Thr Gly Asp Gln His Gln Val Gly Asn Glu Thr Thr Glu His Gly Thr
145             150             155             160

Ile Ala Thr Ile Thr Pro Gln Ala Pro Thr Ser Glu Ile Gln Leu Thr
              165             170             175

Asp Tyr Gly Ala Leu Thr Leu Asp Cys Ser Pro Arg Thr Gly Leu Asp
              180             185             190

Phe Asn Glu Met Val Leu Leu Thr Met Lys Lys Lys Ser Trp Leu Val
              195             200             205

His Lys Gln Trp Phe Leu Asp Leu Pro Leu Pro Trp Thr Ser Gly Ala
              210             215             220

Ser Thr Ser Gln Glu Thr Trp Asn Arg Gln Asp Leu Leu Val Thr Phe
225             230             235             240

Lys Thr Ala His Ala Lys Lys Gln Glu Val Val Val Leu Gly Ser Gln
              245             250             255

Glu Gly Ala Met His Thr Ala Leu Thr Gly Ala Thr Glu Ile Gln Thr
              260             265             270

Ser Gly Thr Thr Thr Ile Phe Ala Gly His Leu Lys Cys Arg Leu Lys
              275             280             285

Met Asp Lys Leu Thr Leu Lys Gly Met Ser Tyr Ala Met Cys Thr Asn
290             295             300

Thr Phe Val Leu Lys Lys Glu Val Ser Glu Thr Gln His Gly Thr Ile
305             310             315             320

Leu Ile Lys Val Glu Tyr Lys Gly Glu Asp Ala Pro Cys Lys Ile Pro
              325             330             335

Phe Ser Thr Glu Asp Glu Lys Gly Lys Thr His Asn Gly Arg Leu Ile
              340             345             350

Thr Ala Asn Pro Val Val Thr Lys Lys Glu Glu Pro Val Asn Ile Glu
              355             360             365

Ala Glu Pro Pro Phe Gly Glu Ser Asn Ile Val Ile Gly Ile Gly Asp
              370             375             380

Asn Ala Leu Lys Ile Asn Trp Phe Lys Lys Gly Ser Ser Ile Gly Lys
385             390             395             400

Met Phe Glu Ala Thr Ala Arg Gly Ala Arg Arg Met Ala Ile Leu Gly
              405             410             415

Asp Thr Ala Trp Asp Phe Gly Ser Ile Gly Gly Val Phe Thr Ser Val
              420             425             430

Gly Lys Leu Ile His Gln Ile Phe Gly Thr Ala Tyr Gly Val Leu Phe
              435             440             445

Ser Gly Val Ser Trp Thr Met Lys Ile Gly Ile Gly Ile Leu Leu Thr
              450             455             460

Trp Leu Gly Leu Asn Ser Arg Ser Thr Ser Leu Ser Met Thr Cys Ile
465             470             475             480

Ala Val Gly Met Val Thr Leu Tyr Leu Gly Val Met Val Gln Ala
              485             490             495
```

<210> SEQ ID NO 13
<211> LENGTH: 495

<212> TYPE: PRT
<213> ORGANISM: Artificial
<220> FEATURE:
<223> OTHER INFORMATION: DENV1/3 chimera

<400> SEQUENCE: 13

```
Met Arg Cys Val Gly Ile Gly Asn Arg Asp Phe Val Glu Gly Leu Ser
1               5                   10                  15

Gly Ala Thr Trp Val Asp Val Val Leu Glu His Gly Ser Cys Val Thr
            20                  25                  30

Thr Met Ala Lys Asp Lys Pro Thr Leu Asp Ile Glu Leu Leu Lys Thr
        35                  40                  45

Glu Val Thr Asn Pro Ala Val Leu Arg Lys Leu Cys Ile Glu Ala Lys
    50                  55                  60

Ile Ser Asn Thr Thr Thr Asp Ser Arg Cys Pro Thr Gln Gly Glu Ala
65                  70                  75                  80

Thr Leu Val Glu Glu Gln Asp Thr Asn Phe Val Cys Arg Arg Thr Phe
                85                  90                  95

Val Asp Arg Gly Trp Gly Asn Gly Cys Gly Leu Phe Gly Lys Gly Ser
            100                 105                 110

Leu Ile Thr Cys Ala Lys Phe Lys Cys Val Thr Lys Leu Glu Gly Lys
            115                 120                 125

Ile Val Gln Tyr Glu Asn Leu Lys Tyr Ser Val Ile Val Thr Val His
        130                 135                 140

Thr Gly Asp Gln His Gln Val Gly Asn Glu Thr Thr Glu His Gly Thr
145                 150                 155                 160

Ile Ala Thr Ile Thr Pro Gln Ala Pro Thr Ser Glu Ile Gln Leu Thr
                165                 170                 175

Asp Tyr Gly Ala Leu Thr Leu Asp Cys Ser Pro Arg Thr Gly Leu Asp
            180                 185                 190

Phe Asn Glu Met Val Leu Leu Thr Met Lys Lys Lys Ser Trp Leu Val
            195                 200                 205

His Lys Gln Trp Phe Leu Asp Leu Pro Leu Pro Trp Thr Ser Gly Ala
    210                 215                 220

Ser Thr Ser Gln Glu Thr Trp Asn Arg Gln Asp Leu Leu Val Thr Phe
225                 230                 235                 240

Lys Thr Ala His Ala Lys Lys Gln Glu Val Val Val Leu Gly Ser Gln
            245                 250                 255

Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
            275                 280                 285

Met Asp Lys Leu Thr Leu Lys Gly Met Ser Tyr Ala Met Cys Thr Asn
    290                 295                 300

Thr Phe Val Leu Lys Lys Glu Val Ser Glu Thr Gln His Gly Thr Ile
305                 310                 315                 320

Leu Ile Lys Val Glu Tyr Lys Gly Glu Asp Ala Pro Cys Lys Ile Pro
                325                 330                 335

Phe Ser Thr Glu Asp Glu Lys Gly Lys Ala His Asn Gly Arg Leu Ile
            340                 345                 350

Thr Ala Asn Pro Val Val Thr Lys Lys Glu Glu Pro Val Asn Ile Glu
        355                 360                 365

Ala Glu Pro Pro Phe Gly Glu Ser Asn Ile Val Ile Gly Ile Gly Asp
    370                 375                 380
```

-continued

```
Asn Ala Leu Lys Ile Asn Trp Phe Lys Lys Gly Ser Ser Ile Gly Lys
385             390             395             400

Met Phe Glu Ala Thr Ala Arg Gly Ala Arg Arg Met Ala Ile Leu Gly
                405             410             415

Asp Thr Ala Trp Asp Phe Gly Ser Ile Gly Gly Val Phe Thr Ser Val
            420             425             430

Gly Lys Leu Ile His Gln Ile Phe Gly Thr Ala Tyr Gly Val Leu Phe
        435             440             445

Ser Gly Val Ser Trp Thr Met Lys Ile Gly Ile Gly Ile Leu Leu Thr
    450             455             460

Trp Leu Gly Leu Asn Ser Arg Ser Thr Ser Leu Ser Met Thr Cys Ile
465             470             475             480

Ala Val Gly Met Val Thr Leu Tyr Leu Gly Val Met Val Gln Ala
                485             490             495

<210> SEQ ID NO 14
<211> LENGTH: 495
<212> TYPE: PRT
<213> ORGANISM: Artificial
<220> FEATURE:
<223> OTHER INFORMATION: DENV1/3 chimera

<400> SEQUENCE: 14

Met Arg Cys Val Gly Ile Gly Asn Arg Asp Phe Val Glu Gly Leu Ser
1               5               10              15

Gly Ala Thr Trp Val Asp Val Val Leu Glu His Gly Ser Cys Val Thr
                20              25              30

Thr Met Ala Lys Asp Lys Pro Thr Leu Asp Ile Glu Leu Leu Lys Thr
            35              40              45

Glu Val Thr Asn Pro Ala Val Leu Arg Lys Leu Cys Ile Glu Ala Lys
        50              55              60

Ile Ser Asn Thr Thr Thr Asp Ser Arg Cys Pro Thr Gln Gly Glu Ala
65              70              75              80

Thr Leu Val Glu Glu Gln Asp Thr Asn Phe Val Cys Arg Arg Thr Phe
                85              90              95

Val Asp Arg Gly Trp Gly Asn Gly Cys Gly Leu Phe Gly Lys Gly Ser
            100             105             110

Leu Ile Thr Cys Ala Lys Phe Lys Cys Val Thr Lys Leu Glu Gly Lys
        115             120             125

Ile Val Gln Tyr Glu Asn Leu Lys Tyr Ser Val Ile Val Thr Val His
    130             135             140

Thr Gly Asp Gln His Gln Val Gly Asn Glu Thr Thr Glu His Gly Thr
145             150             155             160

Ile Ala Thr Ile Thr Pro Gln Ala Pro Thr Ser Glu Ile Gln Leu Thr
                165             170             175

Asp Tyr Gly Ala Leu Thr Leu Asp Cys Ser Pro Arg Thr Gly Leu Asp
            180             185             190

Phe Asn Glu Met Val Leu Leu Thr Met Lys Lys Lys Ser Trp Leu Val
        195             200             205

His Lys Gln Trp Phe Leu Asp Leu Pro Leu Pro Trp Thr Ser Gly Ala
    210             215             220

Ser Thr Ser Gln Glu Thr Trp Asn Arg Gln Asp Leu Leu Val Thr Phe
225             230             235             240

Lys Thr Ala His Ala Lys Lys Gln Glu Val Val Val Leu Gly Ser Gln
                245             250             255
```

```
Glu Gly Ala Met His Thr Ala Leu Thr Gly Ala Thr Glu Ile Gln Thr
            260                 265                 270

Ser Gly Thr Thr Thr Ile Phe Ala Gly His Leu Lys Cys Arg Leu Lys
            275                 280                 285

Met Asp Lys Leu Thr Leu Lys Gly Met Ser Tyr Ala Met Cys Thr Asn
            290                 295                 300

Thr Phe Val Leu Lys Lys Glu Val Ser Glu Thr Gln His Gly Thr Ile
305                 310                 315                 320

Leu Ile Lys Val Glu Tyr Lys Gly Glu Asp Ala Pro Cys Lys Ile Pro
                325                 330                 335

Phe Ser Thr Glu Asp Gly Gln Gly Lys Ala His Asn Gly Arg Leu Ile
            340                 345                 350

Thr Ala Asn Pro Val Val Thr Lys Lys Glu Glu Pro Val Asn Ile Glu
            355                 360                 365

Ala Glu Pro Pro Phe Gly Glu Ser Asn Ile Val Ile Gly Ile Gly Asp
            370                 375                 380

Asn Ala Leu Lys Ile Asn Trp Phe Lys Lys Gly Ser Ser Ile Gly Lys
385                 390                 395                 400

Met Phe Glu Ala Thr Ala Arg Gly Ala Arg Arg Met Ala Ile Leu Gly
                405                 410                 415

Asp Thr Ala Trp Asp Phe Gly Ser Ile Gly Gly Val Phe Thr Ser Val
                420                 425                 430

Gly Lys Leu Ile His Gln Ile Phe Gly Thr Ala Tyr Gly Val Leu Phe
            435                 440                 445

Ser Gly Val Ser Trp Thr Met Lys Ile Gly Ile Gly Ile Leu Leu Thr
            450                 455                 460

Trp Leu Gly Leu Asn Ser Arg Ser Thr Ser Leu Ser Met Thr Cys Ile
465                 470                 475                 480

Ala Val Gly Met Val Thr Leu Tyr Leu Gly Val Met Val Gln Ala
                485                 490                 495
```

<210> SEQ ID NO 15
<211> LENGTH: 166
<212> TYPE: PRT
<213> ORGANISM: Artificial
<220> FEATURE:
<223> OTHER INFORMATION: DENV1 prM sequence prM_DV1_WP74

<400> SEQUENCE: 15

```
Phe His Leu Thr Thr Arg Gly Gly Glu Pro His Met Ile Val Ser Lys
1               5                   10                  15

Gln Glu Arg Gly Lys Ser Leu Leu Phe Lys Thr Ser Ala Gly Val Asn
            20                  25                  30

Met Cys Thr Leu Ile Ala Met Asp Leu Gly Glu Leu Cys Glu Asp Thr
            35                  40                  45

Met Thr Tyr Lys Cys Pro Arg Ile Thr Glu Thr Glu Pro Asp Asp Val
            50                  55                  60

Asp Cys Trp Cys Asn Ala Thr Glu Thr Trp Val Thr Tyr Gly Thr Cys
65                  70                  75                  80

Ser Gln Thr Gly Glu His Arg Arg Asp Lys Arg Ser Val Ala Leu Ala
                85                  90                  95

Pro His Val Gly Leu Gly Leu Glu Thr Arg Thr Glu Thr Trp Met Ser
            100                 105                 110

Ser Glu Gly Ala Trp Lys Gln Ile Gln Lys Val Glu Thr Trp Ala Leu
            115                 120                 125
```

```
Arg His Pro Gly Phe Thr Val Ile Ala Leu Phe Leu Ala His Ala Ile
    130             135             140

Gly Thr Ser Ile Thr Gln Lys Gly Ile Ile Phe Ile Leu Leu Met Leu
145             150             155             160

Val Thr Pro Ser Met Ala
            165

<210> SEQ ID NO 16
<211> LENGTH: 166
<212> TYPE: PRT
<213> ORGANISM: Artificial
<220> FEATURE:
<223> OTHER INFORMATION: DENV3 prM sequence prM_DV3_3001

<400> SEQUENCE: 16

Phe His Leu Thr Ser Arg Asp Gly Glu Pro Arg Met Ile Val Gly Lys
1               5               10              15

Asn Glu Arg Gly Lys Ser Leu Leu Phe Lys Thr Ala Ser Gly Ile Asn
            20              25              30

Met Cys Thr Leu Ile Ala Met Asp Leu Gly Glu Met Cys Asp Asp Thr
        35              40              45

Val Thr Tyr Lys Cys Pro His Ile Thr Glu Val Glu Pro Glu Asp Ile
    50              55              60

Asp Cys Trp Cys Asn Leu Thr Ser Thr Trp Val Thr Tyr Gly Thr Cys
65              70              75              80

Asn Gln Ala Gly Glu His Arg Arg Asp Lys Arg Ser Val Ala Leu Ala
            85              90              95

Pro His Val Gly Met Gly Leu Asp Thr Arg Thr Gln Thr Trp Met Ser
            100             105             110

Ala Glu Gly Ala Trp Arg Gln Val Glu Lys Val Glu Thr Trp Ala Leu
        115             120             125

Arg His Pro Gly Phe Thr Ile Leu Ala Leu Phe Leu Ala His Tyr Ile
    130             135             140

Gly Thr Ser Leu Thr Gln Lys Val Val Ile Phe Ile Leu Leu Met Leu
145             150             155             160

Val Thr Pro Ser Met Thr
            165

<210> SEQ ID NO 17
<211> LENGTH: 166
<212> TYPE: PRT
<213> ORGANISM: Artificial
<220> FEATURE:
<223> OTHER INFORMATION: Chimeric prM_of_DENV1_West_Pac_'74-
      DENV3_Dom_2_s

<400> SEQUENCE: 17

Phe His Leu Thr Ser Arg Asp Gly Glu Pro Arg Met Ile Val Gly Lys
1               5               10              15

Asn Glu Arg Gly Lys Ser Leu Leu Phe Lys Thr Ala Ser Gly Ile Asn
            20              25              30

Met Cys Thr Leu Ile Ala Met Asp Leu Gly Glu Met Cys Asp Asp Thr
        35              40              45

Leu Thr Tyr Lys Cys Pro His Ile Thr Glu Val Glu Pro Glu Asp Ile
    50              55              60

Asp Cys Trp Cys Asn Leu Thr Ser Thr Trp Val Thr Tyr Gly Thr Cys
65              70              75              80

Asn Gln Ala Gly Glu His Arg Arg Asp Lys Arg Ser Val Ala Leu Ala
```

-continued

```
              85              90              95
Pro His Val Gly Met Gly Leu Asp Thr Arg Thr Gln Thr Trp Met Ser
            100             105             110

Ser Glu Gly Ala Trp Lys Gln Ile Gln Lys Val Glu Thr Trp Ala Leu
        115             120             125

Arg His Pro Gly Phe Thr Val Ile Ala Leu Phe Leu Ala His Ala Ile
    130             135             140

Gly Thr Ser Ile Thr Gln Lys Gly Ile Ile Phe Ile Leu Leu Met Leu
145             150             155             160

Val Thr Pro Ser Met Ala
                165
```

METHODS AND COMPOSITIONS FOR RECOMBINANT DENGUE VIRUSES OR VACCINE AND DIAGNOSTIC DEVELOPMENT

STATEMENT OF PRIORITY

This patent application is a 35 U.S.C. § 371 national phase application of PCT Application PCT/US2020/061661 filed Nov. 20, 2020, which claims the benefit, under 35 U.S.C. § 119(e), of U.S. Provisional Application No. 62/938,133, filed on Nov. 20, 2019, the entire contents of each of which are incorporated by reference herein.

STATEMENT OF GOVERNMENT SUPPORT

This invention was made with government support under Grant Nos. AI107731, AI109769, AI125198, and AI106695, awarded by the National Institutes of Health. The government has certain rights in the invention.

STATEMENT REGARDING ELECTRONIC FILING OF A SEQUENCE LISTING

A Sequence Listing in ASCII text format, submitted under 37 C.F.R. § 1.821, entitled 5470-864_ST25.txt, 65,271 bytes in size, generated on May 10, 2022 and filed via EFS-Web, is provided in lieu of a paper copy. This Sequence Listing is hereby incorporated herein by reference into the specification for its disclosures.

FIELD OF THE INVENTION

The present invention is directed to dengue virus vaccines that induce neutralizing antibodies against more than one dengue virus serotype from a single source.

BACKGROUND OF THE INVENTION

Dengue virus (DENV) is a mosquito-borne flavivirus that is spreading at an unprecedented rate and has developed into a major health and economic burden in over 50 countries. Current DENV vaccines protecting against all four DENV serotypes must be delivered as a "tetravalent" formulation of four viruses or four recombinant proteins, each intended to confer protection against that serotype. The correct mix of serotypes in the tetravalent cocktail to achieve a balanced antibody response is not known, underscored by the recent failure of the most advanced tetravalent live attenuated chimeric virus to provide clinically meaningful protection in a large phase 2B trial in Thailand (Sabchareon et al. 2012). Viral interference is thought to contribute to failure as one or more virus serotypes out-compete the others.

The present invention overcomes previous shortcomings in the art by providing chimeric dengue viruses that induce neutralizing antibodies against more than one dengue virus serotype from a single source.

SUMMARY OF THE INVENTION

In one aspect, the present invention provides a chimeric dengue virus E glycoprotein comprising a dengue virus E glycoprotein backbone that comprises amino acid substitutions that introduce an epitope and/or domain that is recognized by an antibody that is reactive with a dengue virus serotype that is different from the dengue virus serotype of the dengue virus E glycoprotein backbone, wherein the dengue virus E glycoprotein backbone is from dengue virus serotype 3 and the antibody is reactive with dengue virus serotype 1.

In another aspect, the present invention provides a chimeric dengue virus E glycoprotein comprising a dengue virus E glycoprotein backbone that comprises amino acid substitutions that introduce an epitope and/or domain that is recognized by an antibody that is reactive with a dengue virus serotype that is different from the dengue virus serotype of the dengue virus E glycoprotein backbone, wherein the dengue virus E glycoprotein backbone is from dengue virus serotype 1 and the antibody is reactive with dengue virus serotype 3.

In one aspect, the present invention provides a chimeric dengue virus E glycoprotein, comprising the following amino acid substitutions wherein the numbering is based on the reference amino acid sequence of an E glycoprotein of dengue virus serotype 3 (DENV3) identified as SEQ ID NO:1: T138S, Q156H, V158T, S167P, A171I, I172Q, P174T, E175D, N270T, G273T, S275T, and D382E, and wherein said dengue virus E glycoprotein further comprises an insertion of the amino acid residues T and E between amino acid residues 155 and 156.

In another aspect, the present invention provides a chimeric dengue virus E glycoprotein, comprising the following amino acid substitutions wherein the numbering is based on the reference amino acid sequence of an E glycoprotein of dengue virus serotype 3 (DENV3) identified as SEQ ID NO:1: Q46L, A50V, L53P, T55V, T138S, Q156H, V158T, T159I, E161T, S167P, T169S, A171I, I172Q, P174T, E175D, T178A, N270T, G273T, S275T, D382E, and N383K, and wherein said dengue virus E glycoprotein further comprises an insertion of the amino acid residues T and E between amino acid residues 155 and 156.

In one aspect, the present invention provides a chimeric dengue virus E glycoprotein, comprising the following amino acid substitutions wherein the numbering is based on the reference amino acid sequence of an E glycoprotein of dengue virus serotype 3 (DENV3) identified as SEQ ID NO:1: Q46L, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S, and wherein said dengue virus E glycoprotein further comprises an insertion of the amino acid residues T and E between amino acid residues 155 and 156.

In another aspect, the present invention provides a chimeric dengue virus E glycoprotein, comprising the following amino acid substitutions wherein the numbering is based on the reference amino acid sequence of an E glycoprotein of dengue virus serotype 3 (DENV3) identified as SEQ ID NO:1: Q46L, Q52N, L53P, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S, and wherein said dengue virus E glycoprotein further comprises an insertion of the amino acid residues T and E between amino acid residues 155 and 156.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: L46Q, N52Q, S138T, T156Q, E157S, T160V, I161T, T163E, S171T, I173A, Q174I, T176P, D177E, T272N, T275G, T277S, E384D, and K385N.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: L46Q, S138T, V141I, T156Q, T160V, I161V, T163E, P169S, S171T, I173A, Q174I, T176P, D177E, A180T, T182G, D184E, T272N, T275G, T277S, and T293E.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, and T272N.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: A63G, S66T, T68I, T81V, V83P, T88Q, F90Y, R93K, R94H, F96Y, I114V, K120Q, V122L, T123E, K124P, L125I, L214F, S225T, S227E, Q228T, E229P, Q234K, D235E, T242N, and T272N.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: L46Q, V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: V300A, G304N, S305T, K307V, E309K, A313S, V320I, V322I, Q323K, K325E, E327K, T329E, S339T, Q340E, V345K, Q347H, I357V, D360K, K363E, Y377N, V380I, A382I, E384D, K385N, L389I, and S390N.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: V300A, G304N, S305T, K307V, E309K, A313S, V320I, V322I, Q323K, K325E, E327K, T329E, S339T, Q340E, V345K, T346A, Q347H, I357V, D360K, K363E, Y377N, V380I, A382I, E384D, K385N, L389I, and S390N.

In another aspect, the present invention provides a chimeric dengue virus E glycoprotein comprising the following amino acid substitutions wherein the numbering is based on the reference amino acid sequence of an E glycoprotein of dengue virus serotype 1 (DENV1) identified as SEQ ID NO:2: V300A, G304N, S305T, K307V, E309K, A313S, V320I, V322I, Q323K, K325E, E327K, T329E, S339T, Q340E, E342G, K343Q, V345K, T346A, Q347H, I357V, D360K, K363E, Y377N, V380I, A382I, E384D, K385N, L389I, and S390N.

Additionally provided herein is a dengue virus particle, a flavivirus particle and/or a virus like particle (VLP) comprising the E glycoprotein of this invention.

An isolated nucleic acid molecule encoding the E glycoprotein of this invention is also provided herein, as well as an isolated nucleic acid molecule encoding the dengue virus particle, flavivirus particle or VLP of this invention.

The present invention also provides a composition comprising the E glycoprotein of this invention in a pharmaceutically acceptable carrier and also provides a composition comprising the nucleic acid molecule of this invention, the vector of this invention, the particle of this invention and/or the population of this invention, in a pharmaceutically acceptable carrier.

The present invention further provides the E glycoprotein of this invention, the dengue virus particle of this invention, the flavivirus particle of this invention, the VLP of this invention, the nucleic acid molecule of this invention, the vector of this invention, the population of this invention and/or the composition of this invention, singly or in any combination, for use in the manufacture of a medicament for producing an immune response to a dengue virus in a subject, for treating a dengue virus infection in a subject in need thereof, for preventing a dengue virus infection in a subject and/or for protecting a subject from the effects of dengue virus infection, and/or for use in any of the methods as disclosed herein.

Also provided herein is the use of the E glycoprotein of this invention, the dengue virus particle of this invention, the flavivirus particle of this invention, the VLP of this invention, the nucleic acid molecule of this invention, the vector of this invention, the population of this invention and/or the composition of this invention, singly or in any combination, for use in producing an immune response to a dengue virus in a subject, in treating a dengue virus infection in a subject in need thereof, in preventing a dengue virus infection in a subject and/or in protecting a subject from the effects of dengue virus infection, and/or for use in any of the methods as disclosed herein.

Also provided herein is a method of producing an immune response to a dengue virus in a subject (e.g., a subject in need thereof), comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

Additionally provided herein is a method of treating a dengue virus infection in a subject (e.g., a subject in need thereof), comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

Further provided herein is a method of preventing a disorder associated with dengue virus infection in a subject (e.g., a subject in need thereof), comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

As an additional aspect, the present invention provides a method of protecting a subject from the effects of dengue virus infection, comprising administering to the subject an effective amount of the E glycoprotein of this invention, the flavivirus particle of this invention, the VLP of this invention, the nucleic acid molecule of this invention, the population of this invention, and/or the composition of this invention and any combination thereof.

In further aspects, the present invention provides methods of identifying the presence of a neutralizing antibody to specific dengue virus serotypes or combinations thereof (e.g., 3/1 and/or 1/3) in a biological sample from a subject, comprising: a) administering a composition comprising a particular E glycoprotein this invention to the subject in an amount effective to induce an antibody response to the E glycoprotein; b) contacting a biological sample from the subject with flavivirus particles comprising the particular E glycoprotein above under conditions whereby neutralization of the flavivirus particles can be detected; and c) detecting neutralization in step (b), thereby identifying the presence of a neutralizing antibody to the specific dengue virus serotypes or combinations thereof in the biological sample from the subject.

The present invention additionally provides a method of identifying the presence of a neutralizing antibody to specific dengue virus serotypes or combinations thereof (e.g., 3/1 and/or 1/3) in a biological sample from a subject, comprising: a) contacting a biological sample from a subject that has been administered a particular E glycoprotein of this invention with flavivirus particles comprising the E glycoprotein under conditions whereby neutralization of the flavivirus particles can be detected; and b) detecting neutralization in step (a), thereby identifying the presence of a neutralizing antibody to the specific dengue virus serotypes or combinations thereof in the biological sample from the subject.

In other embodiments, the present invention provides a method of identifying an immunogenic composition that induces a neutralizing antibody to specific dengue virus serotypes or combinations thereof (e.g., 3/1 and/or 1/3) in a subject, comprising: a) administering an immunogenic composition comprising a particular E glycoprotein of this invention to a subject in an amount effective to induce an antibody response to the E glycoprotein; b) contacting a biological sample from the subject with flavivirus particles comprising the E glycoprotein of step (a) under conditions whereby neutralization of the flavivirus particles can be detected; c) determining if the biological sample comprises an antibody that neutralizes flavivirus particles comprising the E glycoprotein of step (a); and d) identifying the immunogenic composition as inducing a neutralizing antibody to the specific dengue virus serotypes or combinations thereof in the subject if the biological sample comprises an antibody that neutralizes flavivirus particles comprising the E glycoprotein of (a).

Further provided herein is a method of identifying an immunogenic composition that induces a neutralizing antibody to specific dengue virus serotypes or combinations thereof (e.g., 3/1 and/or 1/3) in a subject, the method comprising: a) contacting a biological sample from a subject that has been administered an immunogenic composition comprising a particular E glycoprotein of this invention with flavivirus particles comprising the E glycoprotein under conditions whereby neutralization of the flavivirus particles can be detected; b) determining if the biological sample comprises an antibody that neutralizes flavivirus particles comprising the E glycoprotein of step (a); and c) identifying the immunogenic composition as inducing a neutralizing antibody to the specific dengue virus serotypes or combinations thereof in the subject if the biological sample comprises an antibody that neutralizes flavivirus particles comprising the E glycoprotein of (a).

The present invention also provides a method of detecting an antibody to a specific dengue virus serotype or combination thereof in a sample, comprising: a) contacting the sample with a particular E glycoprotein of this invention under conditions whereby an antigen/antibody complex can form; and b) detecting formation of an antigen/antibody complex, thereby detecting an antibody to the specific dengue virus serotype or combination thereof in the sample.

Additionally provided herein is a method of identifying an antibody to a specific dengue virus serotype or combination thereof in a biological sample from a subject, comprising: a) administering a composition comprising a particular E glycoprotein of this invention to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an antibody to dengue virus serotype 3 and/or 1 in the biological sample from the subject.

A further aspect of the invention provides a method of identifying an antibody to a specific dengue virus serotype or combinations thereof in a biological sample from a subject, comprising: a) contacting a biological sample from a subject that has been administered an immunogenic composition comprising a particular E glycoprotein of this invention with the E glycoprotein under conditions whereby an antigen/antibody complex can form; and c) detecting formation of an antigen/antibody complex, thereby identifying an antibody dengue virus serotype 3 and/or 1 in the biological sample from the subject.

The present invention additionally provides a method of identifying an immunogenic composition that induces an antibody to a specific dengue virus serotype or combination thereof in a subject, the method comprising: a) contacting a biological sample from a subject that has been administered an immunogenic composition comprising a particular E glycoprotein of this invention with the E glycoprotein under conditions whereby an antigen/antibody complex can form; and b) detecting formation of an antigen/antibody complex, thereby identifying an immunogenic composition that induces an antibody to the specific dengue virus serotype or combination thereof in the subject.

A further embodiment of the invention is a method of identifying an immunogenic composition that induces a neutralizing antibody to a specific dengue virus serotype or combination thereof in a subject, comprising: a) administering an immunogenic composition comprising a particular E glycoprotein to a subject in an amount effective to induce an antibody response to the E glycoprotein; b) contacting a biological sample from the subject with the E glycoprotein of (a) under conditions whereby an antigen/antibody complex can form; and c detecting formation an antigen/antibody complex, thereby identifying an immunogenic composition that induces a neutralizing antibody to the specific dengue virus serotype or combination thereof in the subject.

BRIEF DESCRIPTION OF THE DRAWINGS

FIGS. 1A-1D show DENV3/1 chimera PyMOL representations of DENV1 residues transplanted into DENV3 backbone. Number of amino acids changed is in parenthesis. FIG. 1E shows foci at 48 hours on Vero-81 cells for designated chimeric viruses. FIG. 1F shows an amino acid alignment of changed residues in DENV3/1 chimeras. Blank spaces in DENV3 indicate residues not present in DENV1. The residue numbering is based on the reference amino acid sequence of an E glycoprotein of dengue virus serotype 3 (DENV3) identified as SEQ ID NO:1: FIG. 1G shows DENV3/1 chimeras contain DENV1-specific, DENV3-specific and cross-reactive epitopes. $IC_{50}$ values of Vero-81 cell FRNT of DENV3-specific hmAb 5J7, cross-reactive hmAb EDEI C8 and DENV1-specific hmAbs 1F4 and 14c10.

FIGS. 2A-2B shows PyMOL software-generated representations of changed residues in the DENV1/3 EDI-A and DENV1/3 EDI-B chimeras. Transplanted DENV1 residues are shown in spheres on a DENV3 backbone. Top and side views are shown.

FIG. 3A shows DENV3 E glycoprotein dimers for Genotypes I-IV. Amino acid residues that differ from those in the Sri Lanka genotype III are shown as spheres. A black sphere indicates the residue is unique to that genotype and not shared between the genotypes. Shaded spheres indicate residues seen in two or more genotypes. FIG. 3B shows an amino acid alignment of the E glycoproteins of FIG. 3A. The residue numbering is based on the reference amino acid sequence of an E glycoprotein of dengue virus serotype 3 (DENV3) identified as SEQ ID NO:1: Domains are indicated in bar at bottom.

FIGS. 4A and 4B show $IC_{50}$ values of Vero-81 cell FRNT for 5J7 hmAb for gain-of-function (FIG. 4A) and loss-of-function (FIG. 4B) chimeras corresponding to FIG. 4C.

FIG. 5 compares the substitution positions and residues of additional DENV1/3 chimeras in tabulated form against the parental DENV1 and DENV3 residues. The residue numbering is based on the reference amino acid sequence of an E glycoprotein of dengue virus serotype 1 (DENV1) identified as SEQ ID NO:2. "E_of_DENV1_West_Pac_'74-DENV3_Domain_2_with DV1 hinge" is identified as DENV1/3-C, "E_of_DENV1_West_Pac_'74-

DENV3_Domain_2_with DV1 hinge" is identified as DENV1/3-D, "E_of_DENV1_West_Pac_'74-DENV3_Domain_2_+hinge+Q46" is identified as DENV1/3-E, and "E_of_DENV1_West_Pac_'74-DENV3_Domain_2_+hinge+Q46" is identified as DENV1/3-F. The residue of each DENV1/3 chimera at positions not indicated align with the residue of the parental DENV1.

Figure 6B:
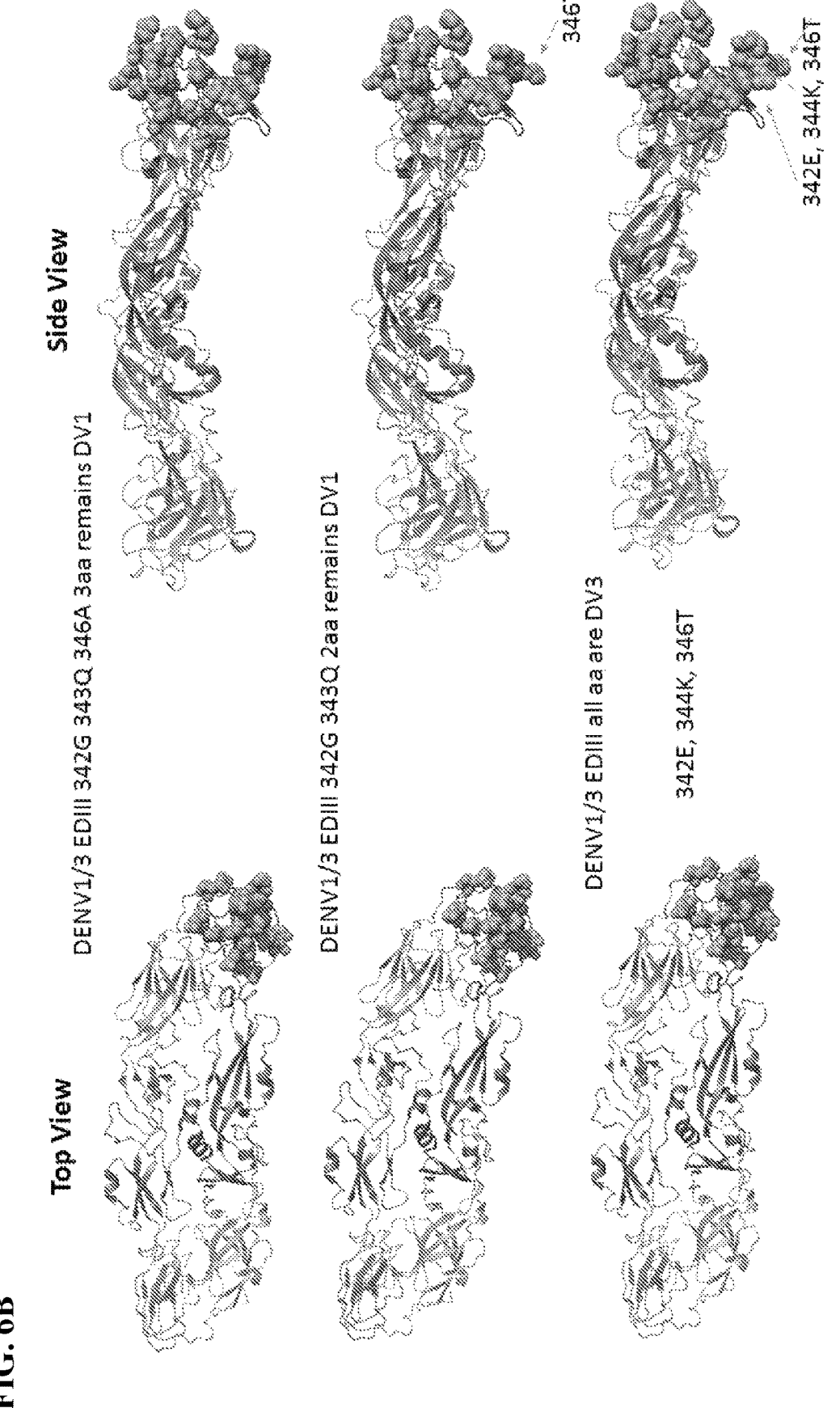

FIG. 6A compares the substitution positions and residues of additional DENV1/3 chimeras in tabulated form against the parental DENV1 and DENV3 residues. The residue numbering is based on the reference amino acid sequence of an E glycoprotein of dengue virus serotype 1 (DENV1) identified as SEQ ID NO:2. FIG. 6B shows PyMOL representations of DENV3 residues transplanted into DENV1 backbone.

DETAILED DESCRIPTION OF THE INVENTION

The present invention is based on the unexpected discovery that epitope regions that define a DENV serotype can be transferred into a protein backbone of a different DENV serotype to create a chimeric molecule that contains antibody targets for both serotypes, thereby functioning as a bivalent vaccine that can induce neutralizing antibodies against two different DENV serotypes from a single source. Thus, in one embodiment, the present invention provides a platform for construction of a chimeric dengue virus E glycoprotein backbone that comprises amino acid substitutions that introduce epitopes that are recognized by an antibody that is reactive with a dengue virus serotype that is different from the dengue virus serotype of the dengue virus E glycoprotein backbone.

In some embodiments, that dengue virus E glycoprotein backbone is from dengue virus serotype 3. In some embodiments, the dengue virus E glycoprotein backbone can be from dengue virus serotype 1, dengue virus serotype 2, or dengue virus serotype 4.

In some embodiments, the antibody that is reactive with a dengue virus serotype that is different from the dengue virus serotype of the dengue virus E glycoprotein backbone is an antibody that is reactive with dengue virus serotype 1. In other embodiments, the antibody that is reactive with a dengue virus serotype that is different from the dengue virus serotype of the dengue virus E glycoprotein backbone is an antibody that is reactive with dengue virus serotype 2, dengue virus serotype 3 or dengue virus serotype 4.

It would be understood that any combination of a first dengue virus serotype for the dengue virus E glycoprotein backbone and a second dengue virus serotype that is the target of the antibody that recognizes the epitope introduced into the E glycoprotein backbone can be used, provided that the first dengue virus serotype and the second dengue virus serotype are different (i.e., not the same serotype).

In some embodiments, a chimeric dengue virus E glycoprotein of the present invention may comprise one or more amino acid substitutions and/or insertions as listed in FIGS. 1F, 2D, 3B, 4C, 5 and/or 6A, wherein the numbering is based on the reference amino acid sequence of an E glycoprotein of dengue virus serotype 3 (DENV3) identified as SEQ ID NO:1.

>E_pro_DENV3_3001_baric (DENV3 reference seq)
(SEQ ID NO: 1)
MRCVGIGNRDFVEGLSGATWVDVVLEHGGCVTTMAKNKPTLDIELQKTEA -continued

TQLATLRKLCIEGKITNITTDSRCPTQGEAVLPEEQDQNYVCKHTYVDRG

WGNGCGLFGKGSLVTCAKFQCLEPIEGKVVQYENLKYTVIITVHTGDQHQ

VGNETQGVTAEITPQASTTEAILPEYGTLGLECSPRTGLDFNEMILLTMK

NKAWMVHRQWFFDLPLPWTSGATTETPTWNRKELLVTFKNAHAKKQEVVV

LGSQEGAMHTALTGATEIQNSGGTSIFAGHLKCRLKMDKLELKGMSYAMC

TNTFVLKKEVSETQHGTILIKVEYKGEDAPCKIPFSTEDGQGKAHNGRLI

TANPVVTKKEEPVNIEAEPPFGESNIVIGIGDNALKINWYKKGSSIGKMF

EATARGARRMAILGDTAWDFGSVGGVLNSLGKMVHQIFGSAYTALFSGVS

WVMKIGIGVLLTWIGLNSKNTSMSFSCIAIGIITLYLGAVVQA

The DENV3 backbone may comprise the amino acid sequence of any DENV3 genotype and/or strain and/or isolate currently known or as yet identified and/or isolated. Non-limiting examples of DENV3 genotypes, strains, and/ or isolates include Genotype I, II, III, IV, and strains such as Sri Lanka 1989, Indonesia 1982, Thailand 1995, Cuba 2002, and Puerto Rico 1977.

In some embodiments, an amino acid residue is substituted adjacent to an insertion. The substitution and residue positions may be described in one or more ways that are redundant in generating the same resultant amino acid sequence. Thus, a disclosure of one such description is herein considered a disclosure of each and inclusive of all such redundant disclosures. For example, an amino acid sequence comprising a substitution at position 156 of a Q to an H (i.e., Q156H) and comprising an insertion of the amino acid residues T and E between amino acid residues 155 and 156, wherein the numbering is based on the reference amino acid sequence of an E glycoprotein of dengue virus serotype 3 (DENV) identified as SEQ ID NO:1 would result in the amino acid sequence as 155T, 156T, 157E, 158H. This modification could redundantly be disclosed by describing a substitution of Q to T at position 156 (i.e., Q156T) and an insertion of the amino acid residues E and H between amino acid residues 156 and 157, also leading to 155T, 156T, 157E, 158H. Thus, wherein the resultant amino acid sequence is identical, any disclosure provided herein describing one way to produce the resultant amino acid sequence is considered a disclosure of each and inclusive of all such redundant disclosures.

In some embodiments, a chimeric dengue virus E glycoprotein of the present invention may comprise the following amino acid substitutions wherein the numbering is based on the reference amino acid sequence of an E glycoprotein of dengue virus serotype 3 (DENV3) identified as SEQ ID NO:1: Q46L, A50V, L53P, T55V, T138S, Q156H, V158T, T159I, E161T, S167P, T169S, A171I, I172Q, P174T, E175D, T178A, N270T, G273T, S275T, D382E, and N383K, and wherein said dengue virus E glycoprotein further comprises an insertion of the amino acid residues T and E between amino acid residues 155 and 156.

In some embodiments, the chimeric dengue virus E glycoprotein of this invention can comprise, consist essentially of or consist of the amino acid sequence:

(SEQ ID NO: 3)
MRCVGIGNRDEVEGLSGATWVDVVLEHGGCVTTMAKNKPTLDIELLKTEV

TQPAVLRKLCIEGKITNITTDSRCPTQGEAVLPEEQDQNYVCKHTYVDRG

-continued

WGNGCGLFGKGSLVTCAKFQCLEPIEGKVVQYENLKYSVIITVHTGDQHQ

VGNETTEHGTIATITPQAPTSEIQLTDYGALGLECSPRTGLDFNEMILLT

MKNKAWMVHRQWFFDLPLPWTSGATTETPTWNRKELLVTFKNAHAKKQEV

VVLGSQEGAMHTALTGATEIQTSGTTTIFAGHLKCRLKMDKLELKGMSYA

MCTNTFVLKKEVSETQHGTILIKVEYKGEDAPCKIPFSTEDGQGKAHNGR

LITANPVVTKKEEPVNIEAEPPFGESNIVIGIGEKALKINWYKKGSSIGK

MFEATARGARRMAILGDTAWDFGSVGGVLNSLGKMVHQIFGSAYTALFSG

VSWVMKIGIGVLLTWIGLNSKNTSMSFSCIAIGIITLYLGAVV
("3/1 large"; "3/1 B")

In some embodiments, a chimeric dengue virus E glycoprotein of the present invention may comprise the following amino acid substitutions wherein the numbering is based on the reference amino acid sequence of an E glycoprotein of dengue virus serotype 3 (DENV3) identified as SEQ ID NO:1: Q46L, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S, and wherein said dengue virus E glycoprotein further comprises an insertion of the amino acid residues T and E between amino acid residues 155 and 156.

In some embodiments, the chimeric dengue virus E glycoprotein of this invention can comprise, consist essentially of or consist of the amino acid sequence:

(SEQ ID NO: 4)
MRCVGIGNRDEVEGLSGATWVDVVLEHGGCVTTMAKNKPTLDIELLKTEA

TQLATLRKLCIEGKITNITTDSRCPTQGEAVLPEEQDQNYVCKHTYVDRG

WGNGCGLFGKGSLVTCAKFQCLEPIEGKVVQYENLKYSVIVTVHTGDQHQ

VGNETTEHGTIATITPQAPTSEIQLTDYGALTLDCSPRTGLDFNEMILLT

MKNKAWMVHRQWFFDLPLPWTSGATTETPTWNRKELLVTFKNAHAKKQEV

VVLGSQEGAMHTALTGATEIQTSGTTTIFAGHLKCRLKMDKLTLKGMSYA

MCTGSFKLKKEVSETQHGTILIKVKYEGTDAPCKIPFSTEDGQGKAHNGR

LITANPVVTKKEEPVNIEAEPPFGESYIVVGAGEKALKLSWYKKGSSIGK

MFEATARGARRMAILGDTAWDFGSVGGVLNSLGKMVHQIFGSAYTALFSG

VSWVMKIGIGVLLTWIGLNSKNTSMSFSCIAIGIITLYLGAVV
("3/1 whole + 5J7"; "3/1 C")

In some embodiments, a chimeric dengue virus E glycoprotein of the present invention may comprise the following amino acid substitutions wherein the numbering is based on the reference amino acid sequence of an E glycoprotein of dengue virus serotype 3 (DENV3) identified as SEQ ID NO:1: Q46L, Q52N, L53P, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S, and wherein said dengue virus E glycoprotein further comprises an insertion of the amino acid residues T and E between amino acid residues 155 and 156.

In some embodiments, the chimeric dengue virus E glycoprotein of this invention can comprise, consist essentially of or consist of the amino acid sequence:

(SEQ ID NO: 5)

```
MRCVGIGNRDEVEGLSGATWVDVVLEHGGCVTTMAKNKPTLDIELLKTEA

TNPATLRKLCIEGKITNITTDSRCPTQGEAVLPEEQDQNYVCKHTYVDRG

WGNGCGLFGKGSLVTCAKFQCLEPIEGKVVQYENLKYSVIVTVHTGDQHQ

VGNETTEHGTIATITPQAPTSEIQLTDYGALTLDCSPRTGLDFNEMILLT

MKNKAWMVHRQWFFDLPLPWTSGATTETPTWNRKELLVTFKNAHAKKQEV

VVLGSQEGAMHTALTGATEIQTSGTTTIFAGHLKCRLKMDKLTLKGMSYA

MCTGSFKLKKEVSETQHGTILIKVKYEGTDAPCKIPFSTEDGQGKAHNGR

LITANPVVTKKEEPVNIEAEPPFGESYIVVGAGEKALKLSWYKKGSSIGK

MFEATARGARRMAILGDTAWDFGSVGGVLNSLGKMVHQIFGSAYTALFSG

VSWVMKIGIGVLLTWIGLNSKNTSMSFSCIAIGIITLYLGAVV
("3/1 whole - 5J7"; "3/1 D")
```

In some embodiments, a chimeric dengue virus E glyco-protein of the present invention may comprise the following amino acid substitutions wherein the numbering is based on the reference amino acid sequence of an E glycoprotein of dengue virus serotype 3 (DENV3) identified as SEQ ID NO:1: T138S, Q156H, V158T, S167P, A171I, I172Q, P174T, E175D, N270T, G273T, S275T, and D382E, and wherein said dengue virus E glycoprotein further comprises an insertion of the amino acid residues T and E between amino acid residues 155 and 156. In some embodiments, a chimeric dengue virus E glycoprotein of the present inven-tion may further comprise one or more of the following amino acid substitutions: A50V, L53P, and/or V305K.

In some embodiments, a chimeric dengue virus E glyco-protein of the present invention may comprise one or more amino acid substitutions and/or insertions as listed in FIGS. 1F, 2D, 3B, 4C, 5 and/or 6A, wherein the numbering is based on the reference amino acid sequence of an E glycoprotein of dengue virus serotype 1 (DENV1) identified as SEQ ID NO:2.

```
>E_pro_DV1 (DENV1 reference seq)
                                    (SEQ ID NO: 2)
MRCVGIGNRDFVEGLSGATWVDVVLEHGSCVTTMAKDKPTLDIELLKTEV

TNPAVLRKLCIEAKISNTTTDSRCPTQGEATLVEEQDTNFVCRRTFVDRG

WGNGCGLFGKGSLITCAKFKCVTKLEGKIVQYENLKYSVIVTVHTGDQHQ

VGNETTEHGTIATITPQAPTSEIQLTDYGALTLDCSPRTGLDFNEMVLLT

MKKKSWLVHKQWFLDLPLPWTSGASTSQETWNRQDLLVTFKTAHAKKQEV

VVLGSQEGAMHTALTGATEIQTSGTTTIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKGSSIGK

MEEATARGARRMAILGDTAWDEGSIGGVFTSVGKLIHQIFGTAYGVLFSG

VSWTMKIGIGILLTWLGLNSRSTSLSMTCIAVGMVTLYLGVMVQA
```

The DENV1 backbone may comprise the amino acid sequence of any DENV1 genotype and/or strain and/or isolate currently known or as yet identified and/or isolated. Non-limiting examples of DENV1 genotypes, strains, and/or isolates include Genotypes I, II, III, IV, and V, and strains Western Pacific 1974.

In some embodiments, a chimeric dengue virus E glyco-protein of the present invention may comprise the following amino acid substitutions wherein the numbering is based on the reference amino acid sequence of an E glycoprotein of dengue virus serotype 1 (DENV1) identified as SEQ ID NO:2: L46Q, N52Q, S138T, T156Q, E157S, T160V, I161T, T163E, S171T, I173A, Q174I, T176P, D177E, T272N, T275G, T277S, E384D, and K385N.

In some embodiments, the chimeric dengue virus E gly-coprotein of this invention can comprise, consist essentially of or consist of the amino acid sequence:

(SEQ ID NO: 6)

```
MRCVGIGNRDEVEGLSGATWVDVVLEHGSCVTTMAKDKPTLDIELQKTEV

TQPAVLRKLCIEAKISNTTTDSRCPTQGEATLVEEQDTNFVCRRTFVDRG

WGNGCGLFGKGSLITCAKFKCVTKLEGKIVQYENLKYTVIVTVHTGDQHQ

VGNETQSHGVTAEITPQAPTTEAILPEYGALTLDCSPRTGLDFNEMVLLT

MKKKSWLVHKQWFLDLPLPWTSGASTSQETWNRQDLLVTFKTAHAKKQEV

VVLGSQEGAMHTALTGATEIQNSGGTSIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGDNALKLSWFKKGSSIGK

MEEATARGARRMAILGDTAWDEGSIGGVFTSVGKLIHQIFGTAYGVLFSG

VSWTMKIGIGILLTWLGLNSRSTSLSMTCIAVGMVTLYLGVMVQA
(DENV1/3-A)
```

In some embodiments, a chimeric dengue virus E glyco-protein of the present invention may comprise the following amino acid substitutions wherein the numbering is based on the reference amino acid sequence of an E glycoprotein of dengue virus serotype 1 (DENV1) identified as SEQ ID NO:2: L46Q, S138T, V141I, T156Q, T160V, I161T, T163E, P169S, S171T, I173A, Q174I, T176P, D177E, A180T, T182G, D184E, T272N, T275G, T277S, and T293E, and wherein said dengue virus E glycoprotein further comprises a deletion of the amino acid residues E157 and H158.

In some embodiments, the chimeric dengue virus E gly-coprotein of this invention can comprise, consist essentially of or consist of the amino acid sequence:

(SEQ ID NO: 7)

```
MRCVGIGNRDEVEGLSGATWVDVVLEHGSCVTTMAKDKPTLDIELQKTEV

TNPAVLRKLCIEAKISNTTTDSRCPTQGEATLVEEQDTNFVCRRTFVDRG

WGNGCGLFGKGSLITCAKFKCVTKLEGKIVQYENLKYTVIITVHTGDQHQ

VGNETQGVTAEITPQASTTEAILPEYGTLGLECSPRTGLDFNEMVLLTMK

KKSWLVHKQWFLDLPLPWTSGASTSQETWNRQDLLVTFKTAHAKKQEVVV

LGSQEGAMHTALTGATEIQNSGGTSIFAGHLKCRLKMDKLELKGMSYVMC

TGSFKLEKEVAETQHGTVLVQVKYEGTDAPCKIPFSSQDEKGVTQNGRLI

TANPIVTDKEKPVNIEAEPPFGESYIVVGAGEKALKLSWFKKGSSIGKMF

EATARGARRMAILGDTAWDFGSIGGVFTSVGKLIHQIFGTAYGVLFSGVS

WTMKIGIGILLTWLGLNSRSTSLSMTCIAVGMVTLYLGVMVQA
(DENV1/3-B)
```

In some embodiments, a chimeric dengue virus E glyco-protein of the present invention may comprise the following amino acid substitutions wherein the numbering is based on the reference amino acid sequence of an E glycoprotein of dengue virus serotype 1 (DENV1) identified as SEQ ID NO:2: P53L, V55T, A63G, S66T, T68I, T81V, V83P, T88Q, F90Y, R93K, R94H, F96Y, I114V, K120Q, V122L, T123E,

13

K124P, L125I, I129V, V197I, K203N, S205A, L207M, K210R, L214F, S225T, S227E, Q228T, E229P, Q234K, D235E, T242N, and T272N.

In some embodiments, the chimeric dengue virus E glycoprotein of this invention can comprise, consist essentially of or consist of the amino acid sequence:

```
                                        (SEQ ID NO: 8)
MRCVGIGNRDEVEGLSGATWVDVVLEHGSCVTTMAKDKPTLDIELLKTEV

TNLATLRKLCIEGKITNITTDSRCPTQGEAVLPEEQDQNYVCKHTYVDRG

WGNGCGLFGKGSLVTCAKFQCLEPIEGKVVQYENLKYSVIVTVHTGDQHQ

VGNETTEHGTIATITPQAPTSEIQLTDYGALTLDCSPRTGLDFNEMILLT

MKNKAWMVHRQWFFDLPLPWTSGATTETPTWNRKELLVTFKNAHAKKQEV

VVLGSQEGAMHTALTGATEIQNSGTTTIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKGSSIGK

MEEATARGARRMAILGDTAWDEGSIGGVFTSVGKLIHQIFGTAYGVLFSG

VSWTMKIGIGILLTWLGLNSRSTSLSMTCIAVGMVTLYLGVMVQA
(E_of_DENV1_West_Pac_'74-DENV3_Domain_2_with
DV1 hinge; "DENV1/3-C")
```

In some embodiments, a chimeric dengue virus E glycoprotein of the present invention may comprise the following amino acid substitutions wherein the numbering is based on the reference amino acid sequence of an E glycoprotein of dengue virus serotype 1 (DENV1) identified as SEQ ID NO:2: A63G, S66T, T68I, T81V, V83P, T88Q, F90Y, R93K, R94H, F96Y, I114V, K120Q, V122L, T123E, K124P, L125I, L214F, S225T, S227E, Q228T, E229P, Q234K, D235E, T242N, and T272N.

In some embodiments, the chimeric dengue virus E glycoprotein of this invention can comprise, consist essentially of or consist of the amino acid sequence:

```
                                        (SEQ ID NO: 9)
MRCVGIGNRDEVEGLSGATWVDVVLEHGSCVTTMAKDKPTLDIELLKTEV

TNPAVLRKLCIEGKITNITTDSRCPTQGEAVLPEEQDQNYVCKHTYVDRG

WGNGCGLFGKGSLVTCAKFQCLEPIEGKIVQYENLKYSVIVTVHTGDQHQ

VGNETTEHGTIATITPQAPTSEIQLTDYGALTLDCSPRTGLDFNEMVLLT

MKKKSWLVHKQWFFDLPLPWTSGATTETPTWNRKELLVTFKNAHAKKQEV

VVLGSQEGAMHTALTGATEIQTSGTTTIFAGHLKCRLKMDKLTLKGMSYV

MCTGSFKLEKEVAETQHGTVLVQVKYEGTDAPCKIPFSSQDEKGVTQNGR

LITANPIVTDKEKPVNIEAEPPFGESYIVVGAGEKALKLSWFKKGSSIGK

MEEATARGARRMAILGDTAWDEGSIGGVFTSVGKLIHQIFGTAYGVLFSG

VSWTMKIGIGILLTWLGLNSRSTSLSMTCIAVGMVTLYLGVMVQA (E_of_DENV1_West_Pac_'74-DENV3_Domain_2_with DV1 hinge bigger; "DENV1/3-D")
```

In some embodiments, a chimeric dengue virus E glycoprotein of the present invention may comprise the following amino acid substitutions wherein the numbering is based on the reference amino acid sequence of an E glycoprotein of dengue virus serotype 1 (DENV1) identified as SEQ ID NO:2: L46Q, V50A, N52Q, P53L, V55T, A63G, S66T, T68I, T81V, V83P, T88Q, F90Y, R93K, R94H, F96Y, I114V,

14

K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S.

In some embodiments, the chimeric dengue virus E glycoprotein of this invention can comprise, consist essentially of or consist of the amino acid sequence:

```
                                        (SEQ ID NO: 10)
MRCVGIGNRDEVEGLSGATWVDVVLEHGSCVTTMAKDKPTLDIELQKTE

ATQLATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQNSGGTSIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPEGESYIVVGAGEKALKLSWF

KKGSSIGKMEEATARGARRMAILGDTAWDEGSIGGVFTSVGKLIHQIFG

TAYGVLFSGVSWTMKIGIGILLTWLGLNSRSTSLSMTCIAVGMVTLYLG

VMVQA (E_of_DENV1_West_Pac_'74-DENV3_Domain_2_ + hinge + Q46; "DENV1/3-E")
```

In some embodiments, a chimeric dengue virus E glycoprotein of the present invention may comprise the following amino acid substitutions wherein the numbering is based on the reference amino acid sequence of an E glycoprotein of dengue virus serotype 1 (DENV1) identified as SEQ ID NO:2: V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S.

In some embodiments, the chimeric dengue virus E glycoprotein of this invention can comprise, consist essentially of or consist of the amino acid sequence:

```
                                        (SEQ ID NO: 11)
MRCVGIGNRDEVEGLSGATWVDVVLEHGSCVTTMAKDKPTLDIELLKTE

ATQLATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQNSGGTSIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPEGESYIVVGAGEKALKLSWF

KKGSSIGKMEEATARGARRMAILGDTAWDEGSIGGVFTSVGKLIHQIFG

TAYGVLFSGVSWTMKIGIGILLTWLGLNSRSTSLSMTCIAVGMVTLYLG

VMVQA (E_of_DENV1_West_Pac_'74-DENV3_Domain_2_ + hinge w DVIL46; "DENV1/3-F")
```

In some embodiments, a chimeric dengue virus E glycoprotein of the present invention may comprise the following amino acid substitutions wherein the numbering is based on the reference amino acid sequence of an E glycoprotein of dengue virus serotype 1 (DENV1) identified as SEQ ID NO:2: V300A, G304N, S305T, K307V, E309K, A313S, V320I, V322I, Q323K, K325E, E327K, T329E, S339T, Q340E, V345K, Q347H, I357V, D360K, K363E, Y377N, V380I, A382I, E384D, K385N, L389I, and S390N.

In some embodiments, the chimeric dengue virus E glycoprotein of this invention can comprise, consist essentially of or consist of the amino acid sequence:

```
                                    (SEQ ID NO: 12)
MRCVGIGNRDEVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDEK

GKTHNGRLITANPVVTKKEEPVNIEAEPPFGESNIVIGIGDNALKINWF

KKGSSIGKMEEATARGARRMAILGDTAWDEGSIGGVFTSVGKLIHQIFG

TAYGVLFSGVSWTMKIGIGILLTWLGLNSRSTSLSMTCIAVGMVTLYLG

VMVQA (E_pro_DV1-3_domain3_A346T_3aaDV1)
```

In some embodiments, a chimeric dengue virus E glycoprotein of the present invention may comprise the following amino acid substitutions wherein the numbering is based on the reference amino acid sequence of an E glycoprotein of dengue virus serotype 1 (DENV1) identified as SEQ ID NO:2: V300A, G304N, S305T, K307V, E309K, A313S, V320I, V322I, Q323K, K325E, E327K, T329E, S339T, Q340E, V345K, T346A, Q347H, I357V, D360K, K363E, Y377N, V380I, A382I, E384D, K385N, L389I, and S390N.

In some embodiments, the chimeric dengue virus E glycoprotein of this invention can comprise, consist essentially of or consist of the amino acid sequence:

```
                                    (SEQ ID NO: 13)
MRCVGIGNRDEVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDEK

GKAHNGRLITANPVVTKKEEPVNIEAEPPFGESNIVIGIGDNALKINWF

KKGSSIGKMEEATARGARRMAILGDTAWDEGSIGGVFTSVGKLIHQIFG

TAYGVLFSGVSWTMKIGIGILLTWLGLNSRSTSLSMTCIAVGMVTLYLG

VMVQA (E_pro_DV1-3_domain3_354-2 + 5)
```

In some embodiments, a chimeric dengue virus E glycoprotein of the present invention may comprise the following amino acid substitutions wherein the numbering is based on the reference amino acid sequence of an E glycoprotein of dengue virus serotype 1 (DENV1) identified as SEQ ID NO:2: V300A, G304N, S305T, K307V, E309K, A313S, V320I, V322I, Q323K, K325E, E327K, T329E, S339T, Q340E, E342G, K343Q, V345K, T346A, Q347H, I357V, D360K, K363E, Y377N, V380I, A382I, E384D, K385N, L389I, and S390N.

In some embodiments, the chimeric dengue virus E glycoprotein of this invention can comprise, consist essentially of or consist of the amino acid sequence:

```
                                    (SEQ ID NO: 14)
MRCVGIGNRDEVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDGQ

GKAHNGRLITANPVVTKKEEPVNIEAEPPFGESNIVIGIGDNALKINWF

KKGSSIGKMEEATARGARRMAILGDTAWDEGSIGGVFTSVGKLIHQIFG

TAYGVLFSGVSWTMKIGIGILLTWLGLNSRSTSLSMTCIAVGMVTLYLG

VMVQA
(E_pro_DV1-3_domain3_all_DV3)
```

Figure 4C:
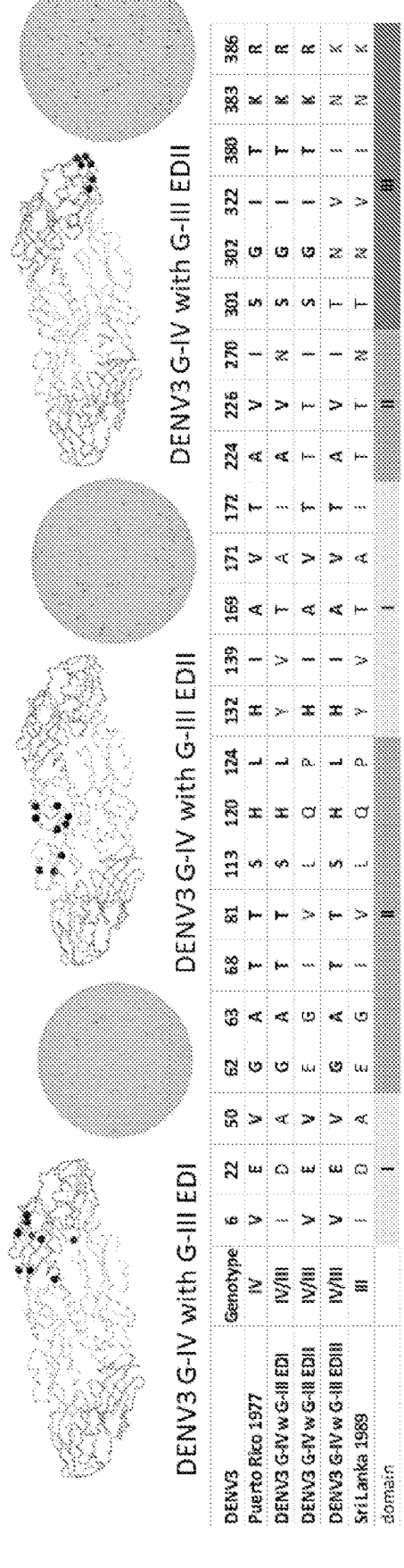
FIG. 4C shows gain-of-function genotype IV DENV3 chimeras with EDI, EDII, or EDIII from genotype III DENV3 (FIG. 4C, top panel), and loss-of-function genotype III DENV3 chimeras with EDI, EDII, or EDIII from genotype IIV DENV3 (FIG. 4C, bottom panel). The residue numbering shown in FIG. 4C is based on the reference amino acid sequence of an E glycoprotein of dengue virus serotype 3 (DENV3) identified as SEQ ID NO:1.

In some embodiments, a chimeric dengue virus E glycoprotein of the present invention may comprise one or more of the substitutions as shown in the tables of FIG. 4C, in any combination, wherein the numbering is based on the reference amino acid sequence of an E glycoprotein of dengue virus serotype 3 (DENV3) identified as SEQ ID NO:1: Non-limiting examples of a backbone of such a chimeric dengue virus E glycoprotein include DENV1, DENV2, DENV3, DENV4, and any genotypes, strains, and/or isolates thereof.

The present invention also provides a dengue virus particle, a flavivirus particle and a virus like particle (VLP) comprising the chimeric E glycoprotein of this invention. The dengue virus E glycoprotein of the invention can be present in an intact virus particle (e.g., a killed or live attenuated virus particle or a recombinant dengue virus vector) or a virus-like particle (VLP), which may optionally be an intact dengue virus particle or dengue virus VLP.

Also provided is an isolated nucleic acid molecule encoding the E glycoprotein of this invention, an isolated nucleic acid molecule encoding the dengue virus particle, the flavivirus particle or the VLP of this invention, a vector comprising the nucleic acid molecule of this invention and a population of dengue virus particles and/or flavivirus particles comprising the dengue virus particle and/or flavivirus particle this invention.

Further provided herein is a composition comprising the E glycoprotein of this invention in a pharmaceutically acceptable carrier, a composition comprising the nucleic acid molecule of this invention in a pharmaceutically acceptable carrier, a composition comprising the virus particle of this invention, a composition comprising the population of this invention in a pharmaceutically acceptable carrier and a composition comprising the VLP of this invention in a pharmaceutically acceptable carrier.

Production of the chimeras of this invention can be carried out by introducing some (e.g., 1, 2, 3, 4, 5, 6, 7, 8, 9, 10, 11, 12, 13, 14, 15, etc.) or all of the amino acid substitutions identified as being part of a dengue virus epitope and/or dengue virus protein domain (e.g., such as in FIGS. 1F, 2D, 3B, 4C, 5 and/or 6A) into a dengue virus E glycoprotein backbone or flavivirus E glycoprotein backbone. Not every amino acid identified as part of a dengue virus epitope or dengue virus protein domain is required to be substituted to produce a chimeric protein of this invention. For example, in some embodiments further substitutions and/or omission of substitutions of about 1, 2, 3, 4 or 5 amino acids at either end of the contiguous amino acid sequences identified as part of a dengue virus epitope or dengue virus domain can be included in the production of a chimera of this invention. The number of substitutions necessary to produce the desired conformational epitope or domain can be readily determined by one of ordinary skill in the art according to the teachings herein and according to protocols well known in the art. The amino acid residue numbering provided in the amino acid sequences set forth here is based on the respective unmodified (e.g., wild type) E glycoprotein amino acid sequence of the respective DENV serotype, as provided herein (e.g., DENV3 3001, SEQ ID NO:1, e.g., DENV1, SEQ ID NO:2). However it would be readily understood by one of ordinary skill in the art that the equivalent amino acid positions in other dengue virus E glycoprotein amino acid sequences or other flavivirus E glycoprotein amino acid sequences can be readily identified and employed in the production of the chimeric proteins of this invention.

FIG. 1F shows three novel examples of modifications that can be made to the nucleotide sequence encoding the DENV3 E glycoprotein to introduce an epitope and/or domain that is recognized by monoclonal antibody reactive with DENV1. The amino acid sequences that result from translation of a nucleotide sequence comprising these substitutions are:

>Epro_3001_DV3-1match_TDV_large
("3/1 large" "3/1 B")

(SEQ ID NO: 3)
MRCVGIGNRDFVEGLSGATWVDVVLEHGGCVTTMAKNKPTLDIELLKTE

VTQPAVLRKLCIEGKITNITTDSRCPTQGEAVLPEEQDQNYVCKHTYVD

RGWGNGCGLFGKGSLVTCAKFQCLEPIEGKVVQYENLKYSVIITVHTGD

QHQVGNETTEHGTIATITPQAPTSEIQLTDYGALGLECSPRTGLDFNEM

ILLTMKNKAWMVHRQWFFDLPLPWTSGATTETPTWNRKELLVTFKNAHA

KKQEVVVLGSQEGAMHTALTGATEIQTSGTTTIFAGHLKCRLKMDKLEL

KGMSYAMCTNTFVLKKEVSETQHGTILIKVEYKGEDAPCKIPFSTEDGQ

GKAHNGRLITANPVVTKKEEPVNIEAEPPFGESNIVIGIGEKALKINWY

KKGSSIGKMEEATARGARRMAILGDTAWDFGSVGGVLNSLGKMVHQIFG

SAYTALFSGVSWVMKIGIGVLLTWIGLNSKNTSMSFSCIAIGIITLYLG

AVV

>Epro_DV3-1_1F4_14c10_5J7_whole
("3/1 whole + 5J7" "3/1 C")

(SEQ ID NO: 4)
MRCVGIGNRDFVEGLSGATWVDVVLEHGGCVTTMAKNKPTLDIELLKTE

-continued
ATQLATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQTSGTTTIFAGHLKCRLKMDKLTL

KGMSYAMCTGSFKLKKEVSETQHGTILIKVKYEGTDAPCKIPFSTEDGQ

GKAHNGRLITANPVVTKKEEPVNIEAEPPFGESYIVVGAGEKALKLSWY

KKGSSIGKMFEATARGARRMAILGDTAWDFGSVGGVLNSLGKMVHQIFG

SAYTALFSGVSWVMKIGIGVLLTWIGLNSKNTSMSFSCIAIGIITLYLG

AVV

>Epro_DV3-1_1F4_14c10_whole
("3/1 whole - 5J7" "3/1 D")

(SEQ ID NO: 5)
MRCVGIGNRDFVEGLSGATWVDVVLEHGGCVTTMAKNKPTLDIELLKTE

ATNPATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQTSGTTTIFAGHLKCRLKMDKLTL

KGMSYAMCTGSFKLKKEVSETQHGTILIKVKYEGTDAPCKIPFSTEDGQ

GKAHNGRLITANPVVTKKEEPVNIEAEPPFGESYIVVGAGEKALKLSWY

KKGSSIGKMFEATARGARRMAILGDTAWDFGSVGGVLNSLGKMVHQIFG

SAYTALFSGVSWVMKIGIGVLLTWIGLNSKNTSMSFSCIAIGIITLYLG

AVV

It would be understood that the modifications shown in FIG. 1F provide three examples of how the amino acid sequence above can be obtained and that, due to the degeneracy of the amino acid codons, numerous other modifications can be made to the nucleotide sequence encoding the DENV3 E glycoprotein to obtain this amino acid sequence.

Figures 2C, 2D, 2E:
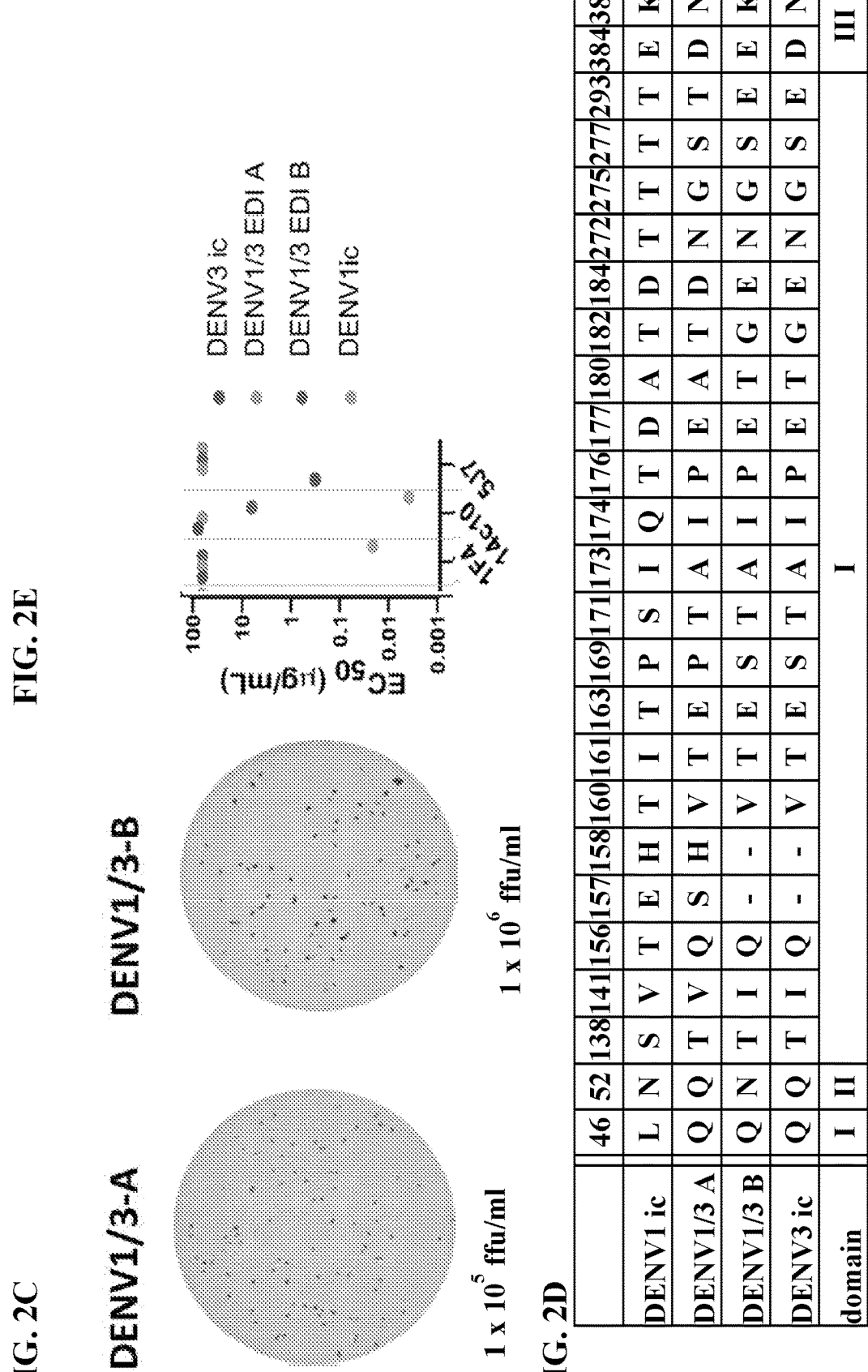
FIG. 2C shows foci at 48 hours on Vero-81 cells for designated chimeric viruses.
FIG. 2D shows an amino acid alignment of changed residues in DENV1/3 EDI chimeras. The residue numbering is based on the reference amino acid sequence of an E glycoprotein of dengue virus serotype 1 (DENV1) identified as SEQ ID NO:2. Blank spaces in DENV3 indicate residues not present in DENV1.
FIG. 2E shows $IC_{50}$ values of Vero-81 cell FRNT of hmAbs against chimeric DENV1/3 viruses. 9 of 10 group 1 hmAbs neutralized both chimeric DENV1/3 viruses. DENV1/3 EDI-B neutralization pattern is most similar to that of DENV3.

FIG. 2D shows two novel examples of modifications that can be made to the nucleotide sequence encoding the DENV1 E glycoprotein to introduce an epitope and/or domain that is recognized by monoclonal antibody reactive with DENV3. The amino acid sequences that result from translation of a nucleotide sequence comprising these substitutions are:

>DENV1-3-A (SEQ ID NO: 6)
MRCVGIGNRDFVEGLSGATWVDVVLEHGSCVTTMAKDKPTLDIELQKTE

VTQPAVLRKLCIEAKISNTTTDSRCPTQGEATLVEEQDTNFVCRRTFVD

RGWGNGCGLFGKGSLITCAKFKCVTKLEGKIVQYENLKYTVIVTVHTGD

QHQVGNETQSHGVTAEITPQAPTTEAILPEYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQNSGGTSIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPFGESYIVVGAGDNALKLSWF

-continued

KKGSSIGKMEEATARGARRMAILGDTAWDEGSIGGVFTSVGKLIHQIFG

TAYGVLFSGVSWTMKIGIGILLTWLGLNSRSTSLSMTCIAVGMVTLYLG

VMVQA

YDENV1-3-B (SEQ ID NO: 7)
MRCVGIGNRDFVEGLSGATWVDVVLEHGSCVTTMAKDKPTLDIELQKTE

VTNPAVLRKLCIEAKISNTTTDSRCPTQGEATLVEEQDTNFVCRRTFVD

RGWGNGCGLFGKGSLITCAKFKCVTKLEGKIVQYENLKYTVIITVHTGD

QHQVGNETQGVTAEITPQASTTEAILPEYGTLGLECSPRTGLDFNEMVL

LTMKKKSWLVHKQWFLDLPLPWTSGASTSQETWNRQDLLVTFKTAHAKK

QEVVVLGSQEGAMHTALTGATEIQNSGGTSIFAGHLKCRLKMDKLELKG

MSYVMCTGSFKLEKEVAETQHGTVLVQVKYEGTDAPCKIPFSSQDEKGV

TQNGRLITANPIVTDKEKPVNIEAEPPFGESYIVVGAGEKALKLSWFKK

GSSIGKMFEATARGARRMAILGDTAWDFGSIGGVFTSVGKLIHQIFGTA

YGVLFSGVSWTMKIGIGILLTWLGLNSRSTSLSMTCIAVGMVTLYLGVM

VQA

It would be understood that the modifications shown in FIG. 2D provide two examples of how the amino acid sequence above can be obtained and that, due to the degeneracy of the amino acid codons, numerous other modifications can be made to the nucleotide sequence encoding the DENV1 E glycoprotein to obtain this amino acid sequence.

FIG. 5 shows four additional novel examples of modifications that can be made to the nucleotide sequence encoding the DENV1 E glycoprotein to introduce an epitope and/or domain that is recognized by monoclonal antibody reactive with DENV3. The amino acid sequences that result from translation of a nucleotide sequence comprising these substitutions are:

>E_of_DENV1_West_Pac_'74-DENV3_Domain_2_with DV1
hinge "DENV1/3-C"

(SEQ ID NO: 8)
MRCVGIGNRDFVEGLSGATWVDVVLEHGSCVTTMAKDKPTLDIELLKTE

VTNLATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQNSGTTTIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPFGESYIVVGAGEKALKLSWF

KKGSSIGKMEEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

>E_of_DENV1_West_Pac_'74-DENV3_Domain_2_with
DV1 hinge bigger "DENV1/3-D"

(SEQ ID NO: 9)
MRCVGIGNRDFVEGLSGATWVDVVLEHGSCVTTMAKDKPTLDIELLKTE

VTNPAVLRKLCIEGKITNITTDSRCPTQGEAVLPEEQDQNYVCKHTYVD

-continued

RGWGNGCGLFGKGSLVTCAKFQCLEPIEGKIVQYENLKYSVIVTVHTGD

QHQVGNETTEHGTIATITPQAPTSEIQLTDYGALTLDCSPRTGLDFNEM

VLLTMKKKSWLVHKQWFFDLPLPWTSGATTETPTWNRKELLVTFKNAHA

KKQEVVVLGSQEGAMHTALTGATEIQTSGTTTIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPFGESYIVVGAGEKALKLSWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

>E_of_DENV1_West_Pac_'74-DENV3_Domain_2_+
hinge + Q46 "DENV1/3-E"

(SEQ ID NO: 10)
MRCVGIGNRDFVEGLSGATWVDVVLEHGSCVTTMAKDKPTLDIELQKTE

ATQLATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQNSGGTSIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPFGESYIVVGAGEKALKLSWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

>E_of_DENV1_West_Pac_'74-DENV3_Domain_2_+
hinge w DV1 L46 "DENV1/3-F"

(SEQ ID NO: 11)
MRCVGIGNRDFVEGLSGATWVDVVLEHGSCVTTMAKDKPTLDIELLKTE

ATQLATLRKLCIEGKITNITTDSRCPTQGEAVLPEEQDQNYVCKHTYVD

RGWGNGCGLFGKGSLVTCAKFQCLEPIEGKVVQYENLKYSVIVTVHTGD

QHQVGNETTEHGTIATITPQAPTSEIQLTDYGALTLDCSPRTGLDFNEM

ILLTMKNKAWMVHRQWFFDLPLPWTSGATTETPTWNRKELLVTFKNAHA

KKQEVVVLGSQEGAMHTALTGATEIQNSGGTSIFAGHLKCRLKMDKLTL

KGMSYVMCTGSFKLEKEVAETQHGTVLVQVKYEGTDAPCKIPFSSQDEK

GVTQNGRLITANPIVTDKEKPVNIEAEPPFGESYIVVGAGEKALKLSWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

It would be understood that the modifications shown in FIG. 5 provide four examples of how the amino acid sequence above can be obtained and that, due to the degeneracy of the amino acid codons, numerous other modifications can be made to the nucleotide sequence encoding the DENV1 E glycoprotein to obtain this amino acid sequence.

FIG. 6A shows three additional novel examples of modifications that can be made to the nucleotide sequence encoding the DENV1 E glycoprotein to introduce an epitope and/or domain that is recognized by monoclonal antibody reactive with DENV3. The amino acid sequences that result from translation of a nucleotide sequence comprising these substitutions are:

>E_pro_DV1-3_domain3_A346T_3aaDV1

(SEQ ID NO: 12)

MRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDEK

GKTHNGRLITANPVVTKKEEPVNIEAEPPFGESNIVIGIGDNALKINWF

KKGSSIGKMEEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

>E_pro_DV1-3_domain3_354-2 + 5

(SEQ ID NO: 13)

MRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDEK

GKAHNGRLITANPVVTKKEEPVNIEAEPPFGESNIVIGIGDNALKINWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

>E_pro_DV1-3_domain3_all_DV3

(SEQ ID NO: 14)

MRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDGQ

GKAHNGRLITANPVVTKKEEPVNIEAEPPFGESNIVIGIGDNALKINWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

It would be understood that the modifications shown in FIG. 6A provide three examples of how the amino acid sequence above can be obtained and that, due to the degeneracy of the amino acid codons, numerous other modifications can be made to the nucleotide sequence encoding the DENV1 E glycoprotein to obtain this amino acid sequence.

In some embodiments, the present invention provides a chimeric E glycoprotein that may interact with a chimeric prM protein. Non-limiting examples of a chimeric E glycoprotein that may interact with a chimeric prM protein include chimeric E glycoproteins with one or more substitutions in domain II (DII). In some embodiments, the present invention provides a chimeric E glycoprotein that may interact with a chimeric prM protein comprising one or more of the following substitutions, wherein the numbering is based on the reference amino acid sequence of a prM protein of dengue virus serotype 1 (DENV1) identified below: T5S, G7D, H11R, S15G, Q17N, S28A, A29S, V31I, L44M, E46D, M49L, R55H, T59V, D61E, V64I, A70L, E72S, S81N, T83A, L101M, E104D, and/or E108Q.

DENV1 prM sequence: prM_DV1_WP74

(SEQ ID NO: 15)

FHLTTRGGEPHMIVSKQERGKSLLFKTSAGVNMCTLIAMDLGELCEDTM

TYKCPRITETEPDDVDCWCNATETWVTYGTCSQTGEHRRDKRSVALAPH

VGLGLETRTETWMSSEGAWKQIQKVETWALRHPGFTVIALFLAHAIGTS

ITQKGIIFILLMLVTPSMA

DENV3 prMsequence: prM_DV3_3001

(SEQ ID NO: 16)

FHLTSRDGEPRMIVGKNERGKSLLFKTASGINMCTLIAMDLGEMCDDTV

TYKCPHITEVEPEDIDCWCNLTSTWVTYGTCNQAGEHRRDKRSVALAPH

VGMGLDTRTQTWMSAEGAWRQVEKVETWALRHPGFTILALFLAHYIGTS

LTQKVVIFILLMLVTPSMT

In some embodiments, the present invention provides a chimeric E glycoprotein that may interact with a chimeric prM protein comprising the amino acid sequence:

Chimeric prM: prM_of_DENV1_West_Pac_'74-DENV3_Dom_2_s (SEQ ID NO: 17)

FHLTSRDGEPRMIVGKNERGKSLLFKTASGINMCTLIAMDLGEMCDDT

LTYKCPHITEVEPEDIDCWCNLTSTWVTYGTCNQAGEHRRDKRSVALA

PHVGMGLDTRTQTWMSSEGAWKQIQKVETWALRHPGFTVIALFLAHAI

GTSITQKGIIFILLMLVTPSMA

In some embodiments, the present invention provides a chimeric flavivirus E glycoprotein in which amino acid substitutions are made to introduce a dengue virus epitope into a flavivirus E glycoprotein from a flavivirus that is not a dengue virus. Thus, in some embodiments, the present invention provides a flavivirus E glycoprotein comprising a chimeric E glycoprotein comprising a flavivirus E glycoprotein backbone that is not a dengue virus E glycoprotein backbone, wherein the flavivirus E glycoprotein backbone comprises amino acid substitutes that introduce an epitope that is recognized by an antibody that is reactive with a dengue virus.

Nonlimiting examples of flaviviruses that can be used include yellow fever virus (YFV) (e.g., GenBank® Database Accession No. JX503529) Japanese encephalitis virus (JEV) (e.g., GenBank® Database Accession No. U14163), West Nile virus (WNV) (e.g., GenBank® Database Accession No. DQ211652) and any other flavivirus now known or later identified.

It is known in the art that many attempts to produce dengue virus vaccines result in the production of non-neutralizing antibodies, which may increase the likelihood of pathology upon subsequence exposure to natural infection or vaccine. Another approach to provide an engineered epitope is to deliver all or a portion of the dengue virus E protein incorporated into another flavivirus particle or VLP. In representative embodiments, the heterologous flavivirus is West Nile virus or Yellow Fever virus. Portions of the E protein can be grafted into the E protein of the heterologous flavivirus backbone, e.g., to reduce the generation of non-neutralizing dengue virus antibodies to non-neutralizing epitopes present in the dengue virus E protein and/or other dengue virus structural proteins.

Thus, a chimeric flavivirus or chimeric flavivirus VLP can present the quaternary dengue virus epitope in proper conformation while reducing the generation of non-neutralizing antibodies to other portions of the dengue virus E protein and/or other structural proteins that are not presented in the chimeric flavivirus or flavivirus VLP.

In some embodiments of the invention the individual and conformational epitopes of the flavivirus E glycoprotein or dengue virus E glycoprotein can be presented on a synthetic backbone or support structure so that the epitopes within the synthetic backbone or support structure mimic the conformation and arrangement of the epitopes within the structure of the E glycoprotein, virus particle or VLP.

In still further embodiments of the invention, the present invention provides peptide mimitopes (see, Meloen et al. (2000) *J. Mol. Recognit.* 13:352-359) that mimic the individual and conformational epitopes of the E glycoproteins of the invention. Mimitopes may be identified using any technique known in the art, including but not limited to surface stimulation, random peptide libraries or phage display libraries, as well as an antibody or antibodies to the individual and conformational epitopes of the E glycoproteins of the invention.

The invention further provides a nucleic acid (e.g., isolated nucleic acid) encoding a dengue virus epitope or a polypeptide of the invention.

The invention further provides a nucleic acid (e.g., an isolated nucleic acid) encoding a chimeric flavivirus VLP or a chimeric flavivirus particle (e.g., a viral coat of the flavivirus particle) of the invention.

Also provided are vectors encoding the nucleic acids of the invention.

Also provided is a cell (e.g., an isolated cell) comprising a vector, a nucleic acid molecule, a dengue virus protein, a dengue virus peptide, a dengue virus protein domain, a flavivirus protein, a flavivirus peptide, flavivirus protein domain, a chimeric dengue virus particle, a chimeric dengue virus VLP, a chimeric flavivirus VLP and/or a chimeric flavivirus particle of this invention, singly or in any combination.

The invention also provides immunogenic compositions comprising the cells, vectors, nucleic acids molecules, dengue virus proteins, chimeric dengue virus VLPs, chimeric dengue virus particles, chimeric flavivirus VLPs and/or chimeric flavivirus particles of the invention, singly or in any combination. In some embodiments, the immunogenic composition is monovalent. In some embodiments, the immunogenic composition is multivalent (e.g., bivalent, trivalent or tetravalent) for dengue virus serotypes DENV1, DENV2, DENV3 and/or DENV4 in any combination. The dengue virus chimeric E glycoproteins of this invention can be administered to a subject singly or in any combination, including any combination of priming and boosting according to such immunization protocols that are known in the art. The dengue virus chimeric E glycoprotein of this invention can be 1/2, 1/3, 1/4, 1/2/3, 1/2/4, 1/3/4, 1/2/3/4, 2/1, 2/3, 2/4, 2/1/3, 2/1/4, 2/3/4, 2/1/3/4, 3/1, 3/2, 3/4, 3/1/2, 3/1/4, 3/2/4, 3/1/2/4, 4/1, 4/2, 4/3, 4/1/3, 4/1/2, 4/3/2, or 4/3/2/1 (wherein the first number of each combination defines the serotype of the backbone and the second, third or fourth number of each combination defines the serotype of the epitope(s) or domain(s) that have been introduced into the backbone). In some embodiments, a dengue virus chimeric E glycoprotein of this invention may comprise one or more substitutions from a serotype which is the same as the serotype of the backbone. In some embodiments, a prime/boost combination would be used that results in administration of antigens representative of all four dengue virus serotypes. Such a prime/boost regimen can include administration of any combination of antigens in any order to achieve this result. A nonlimiting example of a prime/boost protocol can include priming at day 0 and boosting at 3 months and 6 months, or boosting at 6 months and 1 year, respectively. This protocol could also be modified to include only one boost at either 3 months, 6 months or 1 year.

The invention encompasses methods of producing an immune response to a dengue virus in a subject, comprising administering to the subject an effective amount of a dengue virus protein, a chimeric dengue virus particle, a chimeric dengue virus VLP, a chimeric flavivirus VLP, a chimeric flavivirus particle, a nucleic acid molecule, a vector, a cell and/or immunogenic composition of the invention, singly or in any combination.

Further, the present invention can advantageously be practiced to induce an immune response against one, two, three or all four of DENV1, DENV2, DENV3 and DENV4. In some embodiments, the dengue virus chimeric E glycoprotein of this invention and/or a nucleic acid molecule encoding the dengue virus chimeric E glycoprotein of this invention can be administered to a subject singly or in any combination and/or sequence to induce an immune response (e.g., a balanced immune response, in which the parameters of dengue immunity being measured are nearly equivalent for all four DENV serotypes) to all four DENV serotypes. It is well-known in the art that effective and safe multivalent dengue vaccines have been a challenge to design because of the problem of interference among serotypes. For example, the immune response may be predominantly directed against only some of the target serotypes. Multiple vaccinations are then required to try to achieve a response against all serotypes; however, in the case of dengue virus, this approach can be dangerous because repeated administrations to a subject with pre-existing antibodies can lead to dengue hemorrhagic fever.

A still further aspect of the invention is a method of treating a dengue virus infection, comprising administering to the subject an effective amount of a dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention, singly or in any combination or sequence of combinations.

A still further aspect of the invention is a method of preventing a dengue virus infection, comprising administering to the subject an effective amount of a dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention, singly or in any combination or sequence of combinations.

A still further aspect of the invention is a method of protecting a subject from the effects of dengue virus infection, comprising administering to the subject an effective amount of a dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention, singly or in any combination or sequence of combinations.

By "protecting a subject from the effects of dengue virus infection" it is meant that the subject does not develop a disease or disorder caused by a dengue virus infection, or if the subject does develop a disease or disorder caused by a dengue virus infection, the disease or disorder is of less severity and/or symptoms are reduced and/or less severe in the subject in comparison to what the subject would experience upon infection by a dengue virus in the absence of the administration of the dengue virus protein, a dengue virus protein domain, a dengue virus peptide, a chimeric dengue virus particle, a chimeric dengue virus VLP, a chimeric flavivirus VLP a chimeric flavivirus particle, a nucleic acid molecule, a vector, a cell, and/or immunogenic composition of this invention.

The present invention also provides a method of identifying the presence of a neutralizing antibody to dengue virus serotype 1 and/or 3 in a biological sample from a subject, comprising: a) administering a composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 to the subject in an amount effective to induce an antibody response to the E glycoprotein; b) contacting a biological sample from the subject with flavivirus particles comprising the E glycoprotein of step (a) above under conditions whereby neutralization of the flavivirus particles can be detected; and c) detecting neutralization in step (b), thereby identifying the presence of a neutralizing antibody to dengue virus serotype 1 and/or 3 in the biological sample from the subject.

In additional embodiments, the present invention provides a method of identifying the presence of a neutralizing antibody to dengue virus serotype 1 and/or 3 in a biological sample from a subject, comprising: a) administering a composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 to the subject in an amount effective to induce an antibody response to the E glycoprotein; and b) detecting neutralization in step (a), thereby identifying the presence of a neutralizing antibody to dengue virus serotype 1 and/or 3 in the biological sample from the subject.

The present invention further provides a method of identifying an immunogenic composition that induces a neutralizing antibody to dengue virus serotype 1 and/or 3 in a subject, the method comprising: a) administering a composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 to the subject in an amount effective to induce an antibody response to the E glycoprotein; b) contacting a biological sample from the subject with flavivirus particles comprising the E glycoprotein of step (a) under conditions whereby neutralization of the flavivirus particles can be detected; c) determining if the biological sample comprises an antibody that neutralizes flavivirus particles comprising the E glycoprotein of step (a); and d identifying the immunogenic composition as inducing a neutralizing antibody to dengue virus serotype 1 and/or 3 in the subject if the biological sample comprises an antibody that neutralizes flavivirus particles comprising the E glycoprotein of (a).

Additionally provided herein is a method of identifying an immunogenic composition that induces a neutralizing antibody to dengue virus serotype 1 and/or 3 in a subject, the method comprising: a) contacting a biological sample from a subject that has been administered an immunogenic composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 with flavivirus particles comprising the E glycoprotein under conditions whereby neutralization of the flavivirus particles can be detected; b) determining if the biological sample comprises an antibody that neutralizes flavivirus particles comprising the E glycoprotein of step (a); and c) identifying the immunogenic composition as inducing a neutralizing antibody to dengue virus serotype 1 and/or 3 in the subject if the biological sample comprises an antibody that neutralizes flavivirus particles comprising the E glycoprotein of (a).

Also provided herein is a method of detecting an antibody to dengue virus serotype 1 and/or 3 in a sample, comprising; a) contacting the sample with a composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 under conditions whereby an antigen/antibody complex can form; and b) detecting formation of an antigen/antibody complex, thereby detecting an antibody to dengue virus serotype 1 and/or 3 in the sample.

In yet further embodiments, the present invention provides a method of identifying an antibody to dengue virus serotype 1 and/or 3 in a biological sample from a subject, comprising: a) administering a composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 to the subject in an amount effective to induce an antibody response to the E glycoprotein; b) contacting a biological sample from the subject with the E glycoprotein of (a) under conditions whereby an antigen/antibody complex can form; and c) detecting formation of an antigen/antibody complex, thereby identifying an antibody to dengue virus serotype 1 and/or 3 in the biological sample from the subject.

The present invention further provides a method of identifying an antibody to dengue virus serotype 1 and/or 3 in a biological sample from a subject, comprising: a) contacting a biological sample from a subject that has been administered an immunogenic composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 with the E glycoprotein under conditions whereby an antigen/antibody complex can form; and b) detecting formation of an antigen/antibody complex, thereby identifying an antibody dengue virus serotype 1 and/or 3 in the biological sample from the subject.

Also provided herein is a method of identifying an immunogenic composition that induces an antibody to dengue virus serotype 1 and/or 3 in a subject, the method comprising: a) contacting a biological sample from a subject that has been administered an immunogenic composition comprising an E glycoprotein comprising an E glycoprotein backbone of serotype 3 comprising amino acid substitutions that introduce an epitope that is recognized by an antibody that is reactive with dengue virus serotype 1 and/or a composition comprising an E glycoprotein comprising an E glycoprotein backbone of serotype 1 comprising amino acid substitutions that introduce an epitope that is recognized by an antibody that is reactive with dengue virus serotype 3 and/or a composition comprising an E glycoprotein comprising an E glycoprotein backbone of serotype 3 comprising amino acid substitutions that introduce a dengue virus protein domain of dengue virus serotype 1 and/or a composition comprising an E glycoprotein comprising an E glycoprotein backbone of serotype 1 comprising amino acid substitutions that introduce a dengue virus protein domain of dengue virus serotype 3 with the E glycoprotein under conditions whereby an antigen/antibody complex can form; and b) detecting formation of an antigen/antibody complex, thereby identifying an immunogenic composition that induces an antibody to dengue virus serotype 1 and/or 3 in the subject.

In some embodiments, the present invention provides a method of determining an amount of the antibodies produced to the transplanted epitope or domain. For example, DENV3 antibodies that target the 5J7 region could be measured by comparing neutralization of a DENV1/3 chimera with the parent DENV1, with the expectation that DENV3 antibodies could neutralize some portion of DENV1/3 chimera but not parental DENV1.

There are four serotypes of dengue virus (DENV-1, DENV-2, DENV-3 and DENV-4). Within each serotype there are a number of different strains or genotypes. The dengue virus antigens and epitopes of the invention can be derived from any dengue virus, including all serotypes, strains and genotypes, now known or later identified.

In some embodiments of the invention, the dengue virus may be UNC1017 strain (DENV1), West Pacific 74 strain (DENV1), S16803 strain (DENV2), UNC2005 strain (DENV2), UNC3001 strain (DENV3), UNC3043 (DENV3 strain 059.AP-2 from Philippines, 1984), UNC3009 strain (DENV3, D2863, Sri Lanka 1989), UNC3066 (DENV3, strain 1342 from Puerto Rico 1977), CH53489 strain (DENV3), Indonesia 1982 (DENV3), Cuba 2002 (DENV3), UNC4019 strain (DENV4), or TVP-360 (DENV4).

The present invention provides additional no limiting examples of chimeric dengue virus E glycoprotein's of this invention that can be used in the compositions and methods described herein in the SEQUENCES section provided herein.

In embodiments of the invention, an "immunogenically active fragment" of a dengue virus polypeptide (e.g., the E protein) comprises, consists essentially of or consists of at least about 6, 8, 10, 12, 15, 20, 30, 50, 75, 100, 125, 150, 200, 250, 300, 350, 400, 450 or more amino acids, optionally contiguous amino acids, and/or less than about 495, 475, 450, 425, 400, 350, 300, 250, 200, 150, 100, 75 or 50 amino acids, optionally contiguous amino acids, including any combination of the foregoing as long as the lower limit is less than the upper limit, and the "immunogenically active fragment" induces an immune response (e.g., IgG and/or IgA that react with the native antigen), optionally a protective immune response, against dengue virus in a host and induces the production of antibodies that specifically bind to the quaternary dengue virus epitope newly identified by the inventors.

The term "epitope" as used herein means a specific amino acid sequence that, when present in the proper conformation, provides a reactive site for an antibody (e.g., B cell epitope) or T cell receptor (e.g., T cell epitope).

Portions of a given polypeptide that include a B-cell epitope can be identified using any number of epitope mapping techniques that are known in the art. (See, e.g., Epitope Mapping Protocols in Methods in Molecular Biology, Vol. 66, Glenn E. Morris, Ed., 1996, Humana Press, Totowa, N.J.). For example, linear epitopes can be determined by, e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998-4002; Geysen et al. (1986) *Molec. Immunol.* 23:709-715.

Similarly, conformational epitopes can be readily identified by determining spatial conformation of amino acids such as by, e.g., x-ray crystallography and 2-dimensional nuclear magnetic resonance. Antigenic regions of proteins can also be identified using standard antigenicity and hydropathy plots, such as those calculated using, e.g., the Omiga version 1.0 software program available from the Oxford Molecular Group. This computer program employs the Hopp/Woods method (Hopp et al. *Proc. Natl. Acad. Sci USA* (1981) 78:3824-3828) for determining antigenicity profiles and the Kyte-Doolittle technique (Kyte et al. *J. Mol. Biol.* (1982) 157:105-132) for hydropathy plots.

Generally, T-cell epitopes that are involved in stimulating the cellular arm of a subject's immune system are short peptides of about 8-25 amino acids. A common way to identify T-cell epitopes is to use overlapping synthetic peptides and analyze pools of these peptides, or the individual ones, that are recognized by T cells from animals that are immune to the antigen of interest, using, for example, an enzyme-linked immunospot assay (ELISPOT). These overlapping peptides can also be used in other assays such as the stimulation of cytokine release or secretion, or evaluated by constructing major histocompatibility (MHC) tetramers containing the peptide. Such immunogenically active fragments can also be identified based on their ability to stimulate lymphocyte proliferation in response to stimulation by various fragments from the antigen of interest.

The present invention can be practiced for prophylactic, therapeutic and/or diagnostic purposes. In addition, the invention can be practiced to produce antibodies for any purpose, such as diagnostic or research purposes, or for passive immunization by transfer to another subject.

The present invention further provides a kit comprising one or more compositions of this invention. It would be well understood by one of ordinary skill in the art that the kit of this invention can comprise one or more containers and/or receptacles to hold the reagents (e.g., antibodies, antigens, nucleic acids) of the kit, along with appropriate buffers and/or diluents and/or other solutions and directions for using the kit, as would be well known in the art. Such kits can further comprise adjuvants and/or other immunostimulatory or immunomodulating agents, as are well known in the art.

The compositions and kits of the present invention can also include other medicinal agents, pharmaceutical agents, carriers, diluents, immunostimulatory cytokines, etc. Actual methods of preparing such dosage forms are known, or will be apparent, to those skilled in this art.

Administration to a subject can be by any route known in the art. As non-limiting examples, the route of administration can be by inhalation (e.g., oral and/or nasal inhalation), oral, buccal (e.g., sublingual), rectal, vaginal, topical (including administration to the airways), intraocular, transdermal, by parenteral (e.g., intramuscular [e.g., administration to skeletal muscle], intravenous, intra-arterial, intraperitoneal and the like), subcutaneous (including administration into the footpad), intradermal, intrapleural, intracerebral, and/or intrathecal routes.

The epitopes, polypeptides, VLPs and viral vectors of the invention can be delivered per se or by delivering a nucleic acid (e.g., DNA) that encodes the same.

Immunomodulatory compounds, such as immunomodulatory chemokines and cytokines (preferably, CTL inductive cytokines) can be administered concurrently to a subject.

Cytokines may be administered by any method known in the art. Exogenous cytokines may be administered to the subject, or alternatively, a nucleic acid encoding a cytokine may be delivered to the subject using a suitable vector, and the cytokine produced in vivo. In particular embodiments, a viral adjuvant expresses the cytokine.

In embodiments of the invention, multiple dosages (e.g., two, three or more) of a composition of the invention can be administered without detectable pathogenicity (e.g., Dengue Shock Syndrome/Dengue Hemorrhagic Fever).

In embodiments of the invention, the multivalent vaccines of the invention do not result in immune interference, e.g., a balanced immune response is induced against all antigens presented. In embodiments of the invention, the balanced response results in protective immunity against DENV-1, DENV-2, DENV-3 and DENV-4.

In embodiments of the invention, the multivalent vaccine can be administered to a subject that has anti-dengue maternal antibodies present.

It should be appreciated that the invention can be embodied in different forms and should not be construed as limited to the embodiments set forth herein. Rather, these embodiments are provided so that this disclosure will be thorough and complete, and will fully convey the scope of the invention to those skilled in the art.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

The term "about," as used herein when referring to a measurable value such as an amount of dose (e.g., an amount of a fatty acid) and the like, is meant to encompass variations of ±20%, ±10%, ±5%, ±1%, ±0.5%, or even ±0.1% of the specified amount.

As used herein, the transitional phrase "consisting essentially of" means that the scope of a claim is to be interpreted to encompass the specified materials or steps recited in the claim, "and those that do not materially affect the basic and novel characteristic(s)" of the claimed invention. See, In re Herz, 537 F.2d 549, 551-52, 190 U.S.P.Q. 461, 463 (CCPA 1976) (emphasis in the original); see also MPEP § 2111.03. Thus, the term "consisting essentially of" when used in a claim of this invention is not intended to be interpreted to be equivalent to "comprising."

As used herein, the term "nucleic acid" encompasses both RNA and DNA, including cDNA, genomic DNA, synthetic (e.g., chemically synthesized) DNA and chimeras of RNA and DNA. The nucleic acid may be double-stranded or single-stranded. The nucleic acid may be synthesized using nucleotide analogs or derivatives (e.g., inosine or phosphorothioate nucleotides). Such nucleotides can be used, for example, to prepare nucleic acids that have altered base-pairing abilities or increased resistance to nucleases.

As used herein, the term "polypeptide" encompasses both peptides and proteins (including fusion proteins), unless indicated otherwise.

A "fusion protein" is a polypeptide produced when two heterologous nucleotide sequences or fragments thereof coding for two (or more) different polypeptides not found fused together in nature are fused together in the correct translational reading frame.

A "recombinant" nucleic acid, polynucleotide or nucleotide sequence is one produced by genetic engineering techniques.

A "recombinant" polypeptide is produced from a recombinant nucleic acid, polypeptide or nucleotide sequence.

As used herein, an "isolated" polynucleotide (e.g., an "isolated nucleic acid" or an "isolated nucleotide sequence") means a polynucleotide at least partially separated from at least some of the other components of the naturally occurring organism or virus, for example, the cell or viral structural components or other polypeptides or nucleic acids commonly found associated with the polynucleotide. Optionally, but not necessarily, the "isolated" polynucleotide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polynucleotide is at least about 1%, 5%, 10%, 20%, 30%, 40%, 50%, 60%, 70%, 80%, 90%, 95% or more pure.

An "isolated" polypeptide means a polypeptide that is at least partially separated from at least some of the other components of the naturally occurring organism or virus, for example, the cell or viral structural components or other polypeptides or nucleic acids commonly found associated with the polypeptide. Optionally, but not necessarily, the "isolated" polypeptide is present at a greater concentration (i.e., is enriched) as compared with the starting material (e.g., at least about a two-fold, three-fold, four-fold, ten-fold, twenty-fold, fifty-fold, one-hundred-fold, five-hundred-fold, one thousand-fold, ten thousand-fold or greater concentration). In representative embodiments, the isolated polypeptide is at least about 1%, 5%, 10%, 20%, 30%, 40%, 50%, 60%, 70%, 80%, 90%, 95% or more pure.

Furthermore, an "isolated" cell is a cell that has been partially or completely separated from other components with which it is normally associated in nature. For example, an isolated cell can be a cell in culture medium and/or a cell in a pharmaceutically acceptable carrier.

The terms "immunogen" and "antigen" are used interchangeably herein and mean any compound (including polypeptides) to which a cellular and/or humoral immune response can be directed. In particular embodiments, an immunogen or antigen can induce a protective immune response against the effects of dengue virus infection.

"Effective amount" as used herein refers to an amount of a vector, nucleic acid, epitope, polypeptide, cell, particle, VLP, composition or formulation of the invention that is sufficient to produce a desired effect, which can be a therapeutic and/or beneficial effect. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation.

The term "immunogenic amount" or "effective immunizing dose," as used herein, unless otherwise indicated, means an amount or dose sufficient to induce an immune response (which can optionally be a protective response) in the treated subject that is greater than the inherent immunity of non-immunized subjects. An immunogenic amount or effective immunizing dose in any particular context can be routinely determined using methods known in the art.

The terms "vaccine," "vaccination" and "immunization" are well-understood in the art, and are used interchangeably herein. For example, the terms vaccine, vaccination or immunization can be understood to be a process or composition that increases a subject's immune reaction to an immunogen (e.g., by providing an active immune response), and therefore its ability to resist, overcome and/or recover from infection (i.e., a protective immune response).

By the terms "treat," "treating" or "treatment of" (and grammatical variations thereof) it is meant that the severity of the subject's condition is reduced, at least partially improved or ameliorated and/or that some alleviation, mitigation or decrease in at least one clinical symptom is achieved and/or there is a delay in the progression of the disease or disorder. In representative embodiments, the terms "treat," "treating" or "treatment of" (and grammatical variations thereof) refer to a reduction in the severity of viremia and/or a delay in the progression of viremia, with or without other signs of clinical disease.

A "treatment effective" amount as used herein is an amount that is sufficient to treat (as defined herein) the subject. Those skilled in the art will appreciate that the therapeutic effects need not be complete or curative, as long as some benefit is provided to the subject.

The term "prevent," "preventing" or "prevention of" (and grammatical variations thereof) refer to prevention and/or delay of the onset and/or progression of a disease, disorder and/or a clinical symptom(s) in a subject and/or a reduction in the severity of the onset and/or progression of the disease, disorder and/or clinical symptom(s) relative to what would occur in the absence of the methods of the invention. In representative embodiments, the terms "prevent," "preventing" or "prevention of" (and grammatical variations thereof) refer to prevention and/or delay of the onset and/or progression of viremia in the subject, with or without other signs of clinical disease. The prevention can be complete, e.g., the total absence of the disease, disorder and/or clinical symptom(s). The prevention can also be partial, such that the occurrence of the disease, disorder and/or clinical symptom(s) in the subject and/or the severity of onset and/or the progression is less than what would occur in the absence of the present invention.

A "prevention effective" amount as used herein is an amount that is sufficient to prevent (as defined herein) the disease, disorder and/or clinical symptom in the subject. Those skilled in the art will appreciate that the level of prevention need not be complete, as long as some benefit is provided to the subject.

The efficacy of treating and/or preventing dengue virus infection by the methods of the present invention can be determined by detecting a clinical improvement as indicated by a change in the subject's symptoms and/or clinical parameters (e.g., viremia), as would be well known to one of skill in the art.

Unless indicated otherwise, the terms "protect," "protecting," "protection" and "protective" (and grammatical variations thereof) encompass both methods of preventing and treating dengue virus infection in a subject, whether against one or multiple strains, genotypes or serotypes of dengue virus.

The terms "protective" immune response or "protective" immunity as used herein indicates that the immune response confers some benefit to the subject in that it prevents or reduces the incidence and/or severity and/or duration of disease or any other manifestation of infection. For example, in representative embodiments, a protective immune response or protective immunity results in reduced viremia, whether or not accompanied by clinical disease. Alternatively, a protective immune response or protective immunity may be useful in the therapeutic treatment of existing disease.

An "active immune response" or "active immunity" is characterized by "participation of host tissues and cells after an encounter with the immunogen. It involves differentiation and proliferation of immunocompetent cells in lymphoreticular tissues, which lead to synthesis of antibody or the development of cell-mediated reactivity, or both." Herbert B. Herscowitz, *Immunophysiology: Cell Function and Cellular Interactions in Antibody Formation*, in IMMUNOLOGY: BASIC PROCESSES 117 (Joseph A. Bellanti ed., 1985). Alternatively stated, an active immune response is mounted by the host after exposure to immunogens by infection or by vaccination. Active immunity can be contrasted with passive immunity, which is acquired through the "transfer of preformed substances (antibody, transfer factor, thymic graft, interleukin-2) from an actively immunized host to a non-immune host." Id.

A "subject" of the invention includes any animal susceptible to dengue virus infection. Such a subject is generally a mammalian subject (e.g., a laboratory animal such as a rat, mouse, guinea pig, rabbit, primates, etc.), a farm or commercial animal (e.g., a cow, horse, goat, donkey, sheep, etc.), or a domestic animal (e.g., cat, dog, ferret, etc.). In particular embodiments, the subject is a primate subject, a non-human primate subject (e.g., a chimpanzee, baboon, monkey, gorilla, etc.) or a human. Subjects of the invention can be a subject known or believed to be at risk of infection by dengue virus. Alternatively, a subject according to the invention can also include a subject not previously known or suspected to be infected by dengue virus or in need of treatment for dengue virus infection.

Subjects may be treated for any purpose, such as for eliciting a protective immune response or for eliciting the production of antibodies in that subject, which antibodies can be collected and used for other purposes such as research or diagnostic purposes or for administering to other subjects to produce passive immunity therein, etc.

Subjects include males and/or females of any age, including neonates, juvenile, mature and geriatric subjects. With respect to human subjects, in representative embodiments, the subject can be an infant (e.g., less than about 12 months, 10 months, 9 months, 8 months, 7 months, 6 months, or younger), a toddler (e.g., at least about 12, 18 or 24 months and/or less than about 36, 30 or 24 months), or a child (e.g., at least about 1, 2, 3, 4 or 5 years of age and/or less than about 14, 12, 10, 8, 7, 6, 5, or 4 years of age). In embodiments of the invention, the subject is a human subject that is from about 0 to 3, 4, 5, 6, 9, 12, 15, 18, 24, 30, 36, 48 or 60 months of age, from about 3 to 6, 9, 12, 15, 18, 24, 30, 36, 48 or 60 months of age, from about 6 to 9, 12, 15, 18, 24, 30, 36, 48 or 60 months of age, from about 9 to 12, 15, 18, 24, 30, 36, 48 or 60 months of age, from about 12 to 18, 24, 36, 48 or 60 months of age, from about 18 to 24, 30, 36, 48 or 60 months of age, or from about 24 to 30, 36, 48 or 60 months of age.

In embodiments of the invention, the subject has maternal antibodies to dengue virus.

A "subject in need" of the methods of the invention can be a subject known to be, or suspected of being, infected with, or at risk of being infected with, dengue virus.

Pharmaceutical formulations (e.g., immunogenic formulation) comprising the dengue virus epitopes, polypeptides, chimeric flavivirus VLPs or chimeric flavivirus particles, nucleic acids, vectors, cells or compositions of the invention and a pharmaceutically acceptable carrier are also provided, and can be formulated for administration in a pharmaceutical carrier in accordance with known techniques. See, e.g., Remington, *The Science And Practice of Pharmacy* (latest edition). In the manufacture of a pharmaceutical composition according to embodiments of the present invention, the composition of the invention is typically admixed with, inter alia, a pharmaceutically acceptable carrier. By "pharmaceutically acceptable carrier" is meant a carrier that is compatible with other ingredients in the pharmaceutical composition and that is not harmful or deleterious to the subject. The carrier may be a solid or a liquid, or both, and is preferably formulated with the composition of the invention as a unit-dose formulation, for example, a tablet, which may contain from about 0.01 or 0.5% to about 95% or 99% by weight of the composition. The pharmaceutical compositions are prepared by any of the well-known techniques of pharmacy including, but not limited to, admixing the components, optionally including one or more accessory ingredients. In certain embodiments, the pharmaceutically acceptable carrier is sterile and would be deemed suitable for administration into human subjects according to regulatory guidelines for pharmaceutical compositions comprising the carrier.

Furthermore, a "pharmaceutically acceptable" component such as a salt, carrier, excipient or diluent of a composition according to the present invention is a component that (i) is compatible with the other ingredients of the composition in that it can be combined with the compositions of the present invention without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable components include any of the standard pharmaceutical carriers such as phosphate buffered saline solutions, water, emulsions such as oil/water emulsion, microemulsions and various types of wetting agents.

In some embodiments, the compositions of the invention can further comprise one or more than one adjuvant. The adjuvants of the present invention can be in the form of an amino acid sequence, and/or in the form or a nucleic acid encoding an adjuvant. When in the form of a nucleic acid, the adjuvant can be a component of a nucleic acid encoding the polypeptide(s) or fragment(s) or epitope(s) and/or a separate component of the composition comprising the nucleic acid encoding the polypeptide(s) or fragment(s) or epitope(s) of the invention. According to the present invention, the adjuvant can also be an amino acid sequence that is a peptide, a protein fragment or a whole protein that functions as an adjuvant, and/or the adjuvant can be a nucleic acid encoding a peptide, protein fragment or whole protein that functions as an adjuvant. As used herein, "adjuvant" describes a substance, which can be any immuno-modulating substance capable of being combined with a composition of the invention to enhance, improve or otherwise modulate an immune response in a subject.

In further embodiments, the adjuvant can be, but is not limited to, an immunostimulatory cytokine (including, but not limited to, GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules), SYNTEX adjuvant formulation 1 (SAF-1) composed of 5 percent (wt/vol) squalene (DASF, Parsippany, N.J.), 2.5 percent Pluronic, L121 polymer (Aldrich Chemical, Milwaukee), and 0.2 percent polysorbate (Tween 80, Sigma) in phosphate-buffered saline. Suitable adjuvants also include an aluminum salt such as aluminum hydroxide gel (alum), aluminum phosphate, or algannmulin, but may also be a salt of calcium, iron or zinc, or may be an insoluble suspension of acylated tyrosine, or acylated sugars, cationically or anionically derivatized polysaccharides, or polyphosphazenes.

Other adjuvants are well known in the art and include without limitation MF 59, LT-K63, LT-R72 (Pal et al. Vaccine 24(6):766-75 (2005)), QS-21, Freund's adjuvant (complete and incomplete), aluminum hydroxide, N-acetyl-muramyl-L-threonyl-D-isoglutamine (thr-MDP), N-acetyl-normuramyl-L-alanyl-D-isoglutamine (CGP 11637, referred to as nor-MDP), N-acetylmuramyl-L-alanyl-D-isoglutami-nyl-L-alanine-2-(1'-2'-dipalmitoyl-sn-glycero-3-hydroxy-phosphoryloxy)-ethylamine (CGP 19835A, referred to as MTP-PE) and RIBI, which contains three components extracted from bacteria, monophosphoryl lipid A, trealose dimycolate and cell wall skeleton (MPL+TDM+CWS) in 2% squalene/Tween 80 emulsion.

Additional adjuvants can include, for example, a combination of monophosphoryl lipid A, preferably 3-de-O-acy-lated monophosphoryl. lipid A (3D-MPL) together with an aluminum salt. An enhanced adjuvant system involves the combination of a monophosphoryl lipid A and a saponin derivative, particularly the combination of QS21 and 3D-MPL as disclosed in PCT publication number WO 94/00153, or a less reactogenic composition where the QS21 is quenched with cholesterol as disclosed in PCT publication number WO 96/33739. A particularly potent adjuvant formulation involving QS21 3D-MPL & tocopherol in an oil in water emulsion is described in PCT publication number WO 95/17210. In addition, the nucleic acid compositions of the invention can include an adjuvant by comprising a nucleotide sequence encoding the antigen and a nucleotide sequence that provides an adjuvant function, such as CpG sequences. Such CpG sequences, or motifs, are well known in the art.

An adjuvant for use with the present invention, such as, for example, an immunostimulatory cytokine, can be administered before, concurrent with, and/or within a few hours, several hours, and/or 1, 2, 3, 4, 5, 6, 7, 8, 9, and/or 10 days before and/or after the administration of a composition of the invention to a subject.

Furthermore, any combination of adjuvants, such as immunostimulatory cytokines, can be co-administered to the subject before, after and/or concurrent with the administration of an immunogenic composition of the invention. For example, combinations of immunostimulatory cytokines, can consist of two or more immunostimulatory cytokines, such as GM/CSF, interleukin-2, interleukin-12, interferon-gamma, interleukin-4, tumor necrosis factor-alpha, interleukin-1, hematopoietic factor flt3L, CD40L, B7.1 co-stimulatory molecules and B7.2 co-stimulatory molecules. The effectiveness of an adjuvant or combination of adjuvants can be determined by measuring the immune response produced in response to administration of a composition of this invention to a subject with and without the adjuvant or combination of adjuvants, using standard procedures, as described herein and as known in the art.

In embodiments of the invention, the adjuvant comprises an alphavirus adjuvant as described, for example in U.S. Pat. No. 7,862,829.

Boosting dosages can further be administered over a time course of days, weeks, months or years. In chronic infection, initial high doses followed by boosting doses may be advantageous.

The pharmaceutical formulations of the invention can optionally comprise other medicinal agents, pharmaceutical agents, stabilizing agents, buffers, carriers, diluents, salts, tonicity adjusting agents, wetting agents, and the like, for example, sodium acetate, sodium lactate, sodium chloride, potassium chloride, calcium chloride, sorbitan monolaurate, triethanolamine oleate, etc.

For injection, the carrier will typically be a liquid. For other methods of administration, the carrier may be either solid or liquid. For inhalation administration, the carrier will be respirable, and is typically in a solid or liquid particulate form.

The compositions of the invention can be formulated for administration in a pharmaceutical carrier in accordance with known techniques. See, e.g., Remington, The Science And Practice of Pharmacy (9$^{th}$ Ed. 1995). In the manufacture of a pharmaceutical composition according to the invention, the VLPs are typically admixed with, inter alia, an acceptable carrier. The carrier can be a solid or a liquid, or both, and is optionally formulated with the compound as a unit-dose formulation, for example, a tablet. A variety of pharmaceutically acceptable aqueous carriers can be used, e.g., water, buffered water, 0.9% saline, 0.3% glycine, hyaluronic acid, pyrogen-free water, pyrogen-free phosphate-buffered saline solution, bacteriostatic water, or Cremophor EL[R] (BASF, Parsippany, N.J.), and the like. These compositions can be sterilized by conventional techniques. The formulations of the invention can be prepared by any of the well-known techniques of pharmacy.

The pharmaceutical formulations can be packaged for use as is, or lyophilized, the lyophilized preparation generally being combined with a sterile aqueous solution prior to administration. The compositions can further be packaged in unit/dose or multi-dose containers, for example, in sealed ampoules and vials.

The pharmaceutical formulations can be formulated for administration by any method known in the art according to conventional techniques of pharmacy. For example, the compositions can be formulated to be administered intranasally, by inhalation (e.g., oral inhalation), orally, buccally (e.g., sublingually), rectally, vaginally, topically, intrathecally, intraocularly, transdermally, by parenteral administration (e.g., intramuscular [e.g., skeletal muscle], intravenous, subcutaneous, intradermal, intrapleural, intracerebral and intra-arterial, intrathecal), or topically (e.g., to both skin and mucosal surfaces, including airway surfaces).

For intranasal or inhalation administration, the pharmaceutical formulation can be formulated as an aerosol (this term including both liquid and dry powder aerosols). For example, the pharmaceutical formulation can be provided in a finely divided form along with a surfactant and propellant. Typical percentages of the composition are 0.01-20% by weight, preferably 1-10%. The surfactant is generally non-toxic and soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery. Aerosols of liquid particles can be produced by any suitable means, such as with a pressure-driven aerosol nebulizer or an ultrasonic nebulizer, as is known to those of skill in the art. See, e.g., U.S. Pat. No. 4,501,729. Aerosols of solid particles can likewise be produced with any solid particulate medicament aerosol generator, by techniques known in the pharmaceutical art. Intranasal administration can also be by droplet administration to a nasal surface.

Injectable formulations can be prepared in conventional forms, either as liquid solutions or suspensions, solid forms suitable for solution or suspension in liquid prior to injection, or as emulsions. Alternatively, one can administer the pharmaceutical formulations in a local rather than systemic manner, for example, in a depot or sustained-release formulation.

Extemporaneous injection solutions and suspensions can be prepared from sterile powders, granules and tablets of the kind previously described. For example, an injectable, stable, sterile formulation of the invention in a unit dosage form in a sealed container can be provided. The formulation can be provided in the form of a lyophilizate, which can be reconstituted with a suitable pharmaceutically acceptable carrier to form a liquid composition suitable for injection into a subject. The unit dosage form can be from about 1 μg to about 10 grams of the formulation. When the formulation is substantially water-insoluble, a sufficient amount of emulsifying agent, which is pharmaceutically acceptable, can be included in sufficient quantity to emulsify the formulation in an aqueous carrier. One such useful emulsifying agent is phosphatidyl choline.

Pharmaceutical formulations suitable for oral administration can be presented in discrete units, such as capsules, cachets, lozenges, or tables, as a powder or granules; as a solution or a suspension in an aqueous or non-aqueous liquid; or as an oil-in-water or water-in-oil emulsion. Oral delivery can be performed by complexing a compound(s) of the present invention to a carrier capable of withstanding degradation by digestive enzymes in the gut of an animal. Examples of such carriers include plastic capsules or tablets, as known in the art. Such formulations are prepared by any suitable method of pharmacy, which includes the step of bringing into association the protein(s) and a suitable carrier (which may contain one or more accessory ingredients as noted above). In general, the pharmaceutical formulations are prepared by uniformly and intimately admixing the compound(s) with a liquid or finely divided solid carrier, or both, and then, if necessary, shaping the resulting mixture. For example, a tablet can be prepared by compressing or molding a powder or granules, optionally with one or more accessory ingredients. Compressed tablets are prepared by compressing, in a suitable machine, the formulation in a free-flowing form, such as a powder or granules optionally mixed with a binder, lubricant, inert diluent, and/or surface active/dispersing agent(s). Molded tablets are made by molding, in a suitable machine, the powdered protein moistened with an inert liquid binder.

Pharmaceutical formulations suitable for buccal (sublingual) administration include lozenges comprising the compound(s) in a flavored base, usually sucrose and acacia or tragacanth; and pastilles in an inert base such as gelatin and glycerin or sucrose and acacia.

Pharmaceutical formulations suitable for parenteral administration can comprise sterile aqueous and non-aqueous injection solutions, which preparations are preferably isotonic with the blood of the intended recipient. These preparations can contain anti-oxidants, buffers, bacteriostats and solutes, which render the composition isotonic with the blood of the intended recipient. Aqueous and non-aqueous sterile suspensions, solutions and emulsions can include suspending agents and thickening agents. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Pharmaceutical formulations suitable for rectal administration are optionally presented as unit dose suppositories. These can be prepared by admixing the active agent with one or more conventional solid carriers, such as for example, cocoa butter and then shaping the resulting mixture.

Pharmaceutical formulations suitable for topical application to the skin preferably take the form of an ointment, cream, lotion, paste, gel, spray, aerosol, or oil. Carriers that can be used include, but are not limited to, petroleum jelly, lanoline, polyethylene glycols, alcohols, transdermal enhancers, and combinations of two or more thereof. In some embodiments, for example, topical delivery can be performed by mixing a pharmaceutical formulation of the present invention with a lipophilic reagent (e.g., DMSO) that is capable of passing into the skin.

Pharmaceutical formulations suitable for transdermal administration can be in the form of discrete patches adapted to remain in intimate contact with the epidermis of the subject for a prolonged period of time. Formulations suitable for transdermal administration can also be delivered by iontophoresis (see, for example, *Pharmaceutical Research* 3:318 (1986)) and typically take the form of a buffered aqueous solution of the compound(s). Suitable formulations can comprise citrate or bis\tris buffer (pH 6) or ethanol/water and can contain from 0.1 to 0.2M active ingredient.

In embodiments of the invention, the dosage of a virus particle of this invention can be in a range of about $10^4$ to about $10^7$ plaque forming units (PFUs). In embodiments of this invention, the dosage of a VLP of this invention can be in a range of about 500 micrograms to about 5 milligrams. In embodiments of this invention, the dosage of a protein of this invention can be in a range of about 100 to about $10^4$ micrograms+/–adjuvant.

Further, the composition can be formulated as a liposomal formulation. The lipid layer employed can be of any conventional composition and can either contain cholesterol or can be cholesterol-free. The liposomes that are produced can be reduced in size, for example, through the use of standard sonication and homogenization techniques.

The liposomal formulations can be lyophilized to produce a lyophilizate which can be reconstituted with a pharmaceutically acceptable carrier, such as water, to regenerate a liposomal suspension.

The immunogenic formulations of the invention can optionally be sterile, and can further be provided in a closed pathogen-impermeable container.

EXAMPLES

Example 1: Chimeric DENV 3/1 and DENV 1/3 Epitope Substitutions

Dengue viruses (DENV) are positive-sense RNA viruses belonging to the Flavivirus genus of Flaviviridae and are transmitted to humans by *Aedes aegypti* or *Aedes albopictus* mosquitoes. It is estimated that the 4 serotypes of DENV (DENV1-4) are responsible for over a 100 million new infections each year. While the majority of DENV infections are asymptomatic, symptomatic cases present with symptoms ranging from a mild fever to severe dengue shock syndrome and hemorrhagic fever. Complicating vaccine design, infection with one DENV serotype does not confer lasting protective immunity to the other three serotypes. After a primary infection, type-specific (TS) antibodies to the infection serotype are associated with durable, life-long, protection. Although cross-reactive (CR) antibodies to the other three serotypes develop during a primary infection, such antibodies are only correlated with transient cross-protective immunity. In fact, CR antibodies have been implicated in enhanced viral replication and an increased risk of severe disease. Hence, despite the induction of robust TS immunity, an individual with a single previous DENV infection may remain susceptible to developing severe forms of disease during a secondary infection with virus from a heterologous serotype. Following a secondary infection, the sera of individuals who recover typically have high affinity CR serum antibodies, which are associated with durable serotype cross-protective immunity. However, the full repertoire of antibodies and epitopes elicited following primary and secondary DENV infections remains only partially characterized, preventing a full understanding of the mechanisms of protective immunity and immune enhancement.

The DENV envelope (E) glycoprotein mediates viral binding and entry into cells and is the main target of neutralizing antibodies after infection and vaccination. The four DENV serotypes vary by 25 to 40% in the amino acid sequence of the E protein. Within each serotype, the E protein sequence of different genotypes varies by 6 to 9%. Genotypic variation plays an underappreciated role in immune escape. The DENV E protein consists of three major domains (designated E protein domain I [EDI], EDII, and EDIII), and two of these protomers form head-to-tail dimers on the surface of viral particles. Three dimers lie parallel to each and form thirty rafts in a herringbone pattern on the mature virion. A handful of human TS neutralizing antibodies against DENV1, DENV2, DENV3 or DENV4 have been mapped, many of which recognize quaternary structural epitopes that span different E protein molecules and are therefore only present on the assembled virion. The human antibody response to DENV3 has been studied less than the other serotypes at the clonal level. A single potent TS neutralizing human monoclonal antibody (hmAb) 5J7 was described, which recognizes a complex quaternary epitope spanning across three E protomers in viral particles. Using viral reverse genetics, we demonstrated previously that residues in the DENV3 hmAb 5J7 epitope can be transplanted into infectious virions with a viral E protein that is based on a representative sequence of a DENV1 or DENV4 virus (Andrade et al. 2017 *MBio* 8(5):e01205-17; Messer et al. 2016 *J. Virol.* 90:5090-5097; Widman et al. 2017 *Sci. Rep.* 7:17169). After interrogation with panels of hmAbs and primary sera, these studies revealed that only a small fraction of the polyclonal DENV3-reactive neutralizing antibody response targets the complex hmAb 5J7 epitope, suggesting that major neutralizing epitopes of DENV3 remained undiscovered.

Epitope Mapping using DENV3 Loss of Function Recombinant Viruses. We previously used recombinant chimeric DENVs to map epitopes in DENV1, DENV2, DENV3 and DENV4 recognized by murine and human mAbs (Gallichotte et al. 2018 *Adv. Exp. Med. Biol.* 1062:63-76; Gallichotte et al. 2018 *Cell Rep.* 25:1214-1224; Gallichotte et al. 2018 *PLoS Pathog.* 14:e1006934; Gallichotte et al. 2017 *MSphere* 2(1):e00380-16; Swanstrom et al. 2019 *J. Infect. Dis.* 220:219-22). To further characterize the epitopes recognized by a set of DENV3 TS hmAbs, we first generated a panel of DENV3 loss-of-function mutant viruses that encoded progressively larger portions of the epitopes of the DENV1 TS hmAbs 1F4 and 14c10. These epitopes, which mostly reside in EDI and/or a portion of EDIII of DENV1, were transplanted into the DENV3 backbone (FIGS. 1A-1D, Table 1). To map binding sites for neutralizing antibodies, we used a previously described DENV3/1 EDI-A chimeric virus, which incorporates 22 residues of the DENV1 EDI 1F4 footprint in the E protein. Another closely matched derivative called DENV3/1 EDI-B (23 residues) was also isolated, which extended the original DENV3/1 EDI-A transplanted region to include two residues in EDIII of the neighboring protomer (e.g., D384E and N385K), removed one DENV1 residue from the EDI/II hinge region (N52Q), removed one DENV1 residue from the interior of EDI (V141I) and corrected a tissue-culture-induced mutation at residue F46L. The design of the DENV3/1 EDI/III-C chimeric virus further reduced the number of transplanted residues in the EDI/II hinge region by 3 residues (V50A, P53L and V55T), but converted most of the DENV3 ED I and ED III domains to DENV1, thereby increasing the total number of transplanted residues to 35 amino acids (Table 1). The final derivative, designated the DENV3/1 EDI/III-D chimera, builds upon the DENV3/1 EDI/III-C backbone by converting an additional 3 residues in the domain I/II hinge area of DENV3 to DENV1 (Q52N, L53P and T55V) resulting in a total of 38 residues transplanted into DENV3. All recombinant viruses replicated efficiently in Vero cell monolayer cultures to titers of $10^5$ to $10^6$ FFU/mL (FIGS. 1A-1G).

To demonstrate appropriate epitope exchange had been achieved in the chimeras, the ability of the DENV3 TS 5J7 hmAb and the DENV1 TS hmAbs 1F4 or 14c10 to neutralize the panel of wild-type or DENV3/1 chimeric viruses was investigated (FIG. 1G). Whereas the DENV1 TS hmAb 1F4 neutralized all 4 of the DENV3/1 chimeras, only the DENV3/1 EDI/III-D (38aa) chimera fully restored the DENV1 14c10 antibody neutralization phenotype, reflecting the transplant of the entire 14c10 epitope, which extends across EDI, EDIII and the EDI/II hinge region. The other 3 chimeras partially restored the 14c10 neutralization phenotype. For 14c10, residues Q52N, L53P and T55V, within the EDI/II hinge region were critical for 14c10 neutralization in DENV1 chimeras (FIG. 1G). Conversely, neutralization by hmAb 5J7 was retained in DENV3/1 EDI/III-C, but not in the DENV3/1 EDI/III-D recombinant virus. These data further demonstrate the critical importance of these same three residues for hmAb 5J7 neutralization in DENV3. These data also support previous atomic level resolution studies that show the hmAb 5J7 and 14c10 epitopes extend in opposite directions from an area of overlap within the EDI/II hinge in their respective serotypes. Even though the mAb 1F4 epitope overlapped the EDI/II hinge area as observed in cryogenic electron microscopy (cryo-EM) of the antibody-virus complex, variation in this area did not hinder its ability to neutralize viruses in the chimeric panel. As expected, the CR hmAb EDE1 epitope-specific. Additional DENV3 hmAbs were tested for the ability to neutralize viruses in the chimeric DENV3/1 panel. DENV3-specific hmAbs grouped into three distinct neutralization classes based on ability to neutralize the chimeras, defined as group I antibodies which likely target the core residues of the DENV3 EDI domain and did not neutralize any of the DENV3/1 chimeras detectably; group 2 which efficiently neutralized wild-type DENV3 virus and all DENV3/1 loss-of-function chimeric viruses and likely target residues in EDII and perhaps a small portion of EDIII of DENV3; and group 3 antibodies which only neutralized the chimeras with the smallest transplanted regions (DENV3/1-EDI-A and DENV3/1-EDI-B), which likely target residues outside of the EDI domain.

Chimeric DENV1/3 Gain of Function Recombinant Virus Mapping. Chimeric loss-of-function E glycoproteins may disrupt long-range protein-protein interactions and complicate the interpretation of DENV3/1 antibody-epitope map locations. Therefore, we designed and recovered a panel of DENV1/3 gain-of-function EDI mutant viruses (FIG. 2A) to validate the predicted EDI map locations of the 10 DENV3 hmAbs. Using our DENV1 molecular clone, we introduced progressively larger portions of the EDI domain from DENV3 into DENV1 (FIG. 2). In the DENV1/3-EDI-A recombinant virus, we replaced the varying DENV1 surface contact residues for hmAb 1F4 and 14c10 antibodies in EDI with the corresponding DENV3 residues. The virus expressed by this construct should not be neutralized by DENV1 TS hmAbs 1F4 or 14c10 nor DENV3 TS mAb 5J7 (FIGS. 2A-2D). In DENV1/3 EDI-B, we transplanted the entire EDI of DENV3 into DENV1, including both the previously described surface residues and the interior residues (e.g., V141I, P169S, A180T, T182G, D184E and T293E). In addition, we deleted DENV1 residues E157 and H158, because these two amino acids do not exist in the DENV3 EDI domain. This construct probes the role of both the surface and interior residues in hmAb binding and neutralization. The two gain-of-function chimeric viruses replicated efficiently in Vero cell culture monolayers to titers of ~$10^5$ FFU/mL (FIGS. 2A-2E).

Consistent with the defined structural interaction domains of each antibody/epitope pair, both DENV1/3 EDI-A and DENV1/3 EDI-B chimeric viruses were not neutralized by the DENV1 TS hmAbs 1F4, 14c10 nor DENV3 TS hmAb 5J7 (FIG. 2E).

Figure 3C:
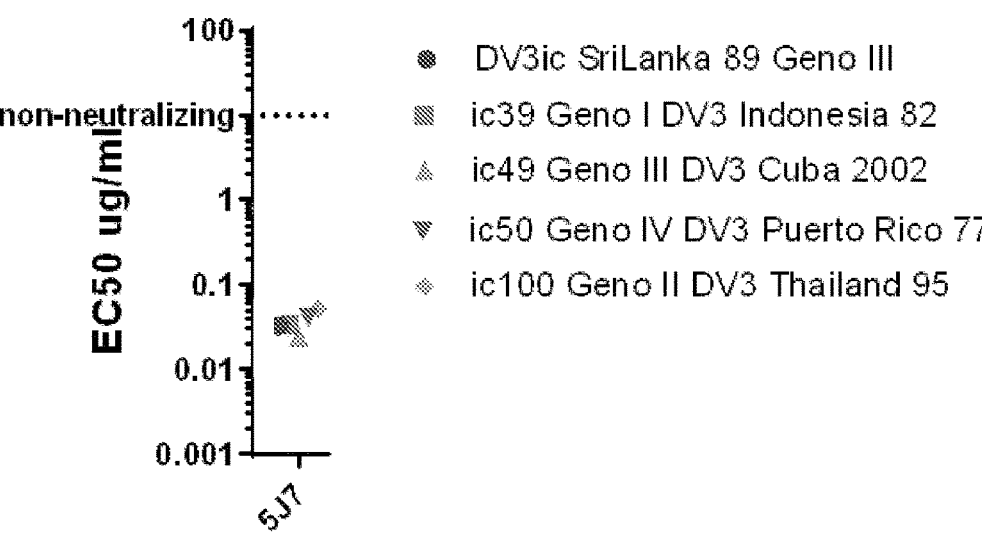
FIG. 3C shows genotype variation alters FRNT neutralization $IC_{50}$ values for select DENV3 5J7 hmAb.
Figure 3C:
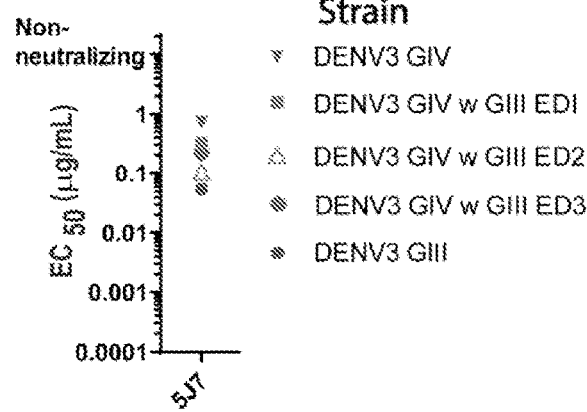
Figure 3C:
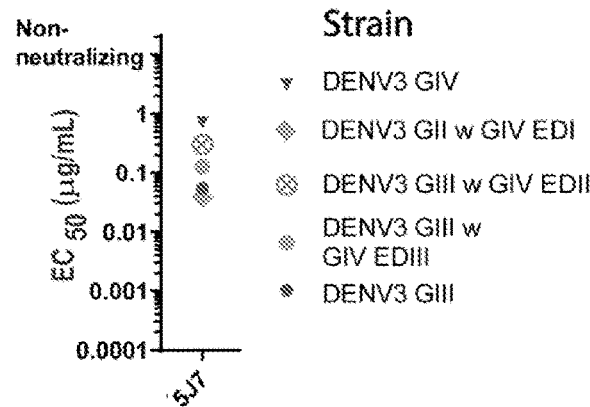

DENV3 Genotypes I-IV Neutralization Phenotypes. To validate the location of the DENV3 epitopes, we determined if natural variation encoded within a panel of recombinant DENV3 viruses representing genotypic variation in field strains altered the neutralization profiles of hmAbs in the panel (FIGS. 3A-3C). Viruses in the DENV3 recombinant panel encode the E glycoproteins from genotypes I, II, III or IV introduced into the DENV3 Sri Lanka genotype III backbone. Although each genotype strain encoded distinct amino acid differences across EDI, EDII and EDIII, all DENV3 genotypes were highly sensitive to neutralization by hmAb 5J7. The largest amino acid variation exists between genotypes III and IV.

Fine Mapping hmAB that target ED1 and EDII Epitope Domains. As natural variation in DENV3 genotype IV contains clustered variation in EDI, EDII and EDIII that altered the neutralization profiles of group 1-3 hmAbs and 5J7, exchange of the ED regions between susceptible (e.g., GIII) and resistant (e.g., GIV) genotypes of DENV3 should localize the epitope domain of selected group 1, 2, and 3 hmAbs and 5J7. We used viral reverse genetics to introduce either the EDI, EDII or the EDIII regions from the resistant DENV3 genotype IV E glycoprotein into the sensitive DENV3 genotype III strain (FIGS. 4A-4C and Table 2) or vice versa, allowing us to map critical functional residues using both gain- and loss-of-function studies. While an exact epitope cannot be gleaned from this mapping approach alone, the functional epitope for each individual antibody neutralization phenotype is defined, identifying core domains/sequences that are required for the antibody to neutralize the virus.

Dengue vaccine-induced immunity relies on the development and maintenance of long-term protective antibody titers and serological memory. Although a licensed live attenuated dengue virus vaccine (Dengvaxia) demonstrated vaccine efficacy in DENV-naive populations, breakthrough infections were common. In particular, vaccine efficacy in naive individuals was less robust than in preimmune individuals, and could result in more severe disease after infection. The best studied correlate for protective immunity after DENV infection is the development of high titers of serum neutralizing antibodies. Using both gain- and loss-of-epitope chimeric viruses, coupled with panels of viruses that encode natural variation or targeted mutations and small animal model studies, three classes of neutralizing antibodies were identified and their "core" epitope locations within the DENV3 E glycoprotein that likely reflect six new and/or overlapping neutralizing epitopes localized in and across EDI, EDII and EDIII. The panels of chimeric viruses and recombinant proteins reported herein provide a powerful resource to determine if uncharacterized antibodies recognize known or unique epitopes in DENV3. Data from this study suggest that the surface topology of the E glycoprotein is more authentic when both surface and underlying residues are exchanged between serotypes.

The recombinant proteins and chimeric viruses reported herein provide key reagents for evaluating vaccine immunogenicity and for measuring epitope specific responses association with natural infections or vaccinations, potentially leading to the identification of new correlates of protective immunity. In particular, breakthrough infections occur in individuals with high titer polyclonal neutralizing responses against all four DENV serotypes, including DENV3. Moreover, naïve children receiving a tetravalent vaccine are at increased risk for severe DENV after infection, reaffirming a critical need for better correlates of protective immunity. This study demonstrates the importance of evaluating the TS neutralizing antibody responses in both children and adults experiencing primary or secondary infections with DENV. It is clear from this study that the DENV3 antigenic neutralizing landscape is very complex and is composed of at least seven epitopes encoded on or across EDI, II and III.

Materials and Methods: The protocols for the Pediatric Dengue Cohort Study and the Pediatric Dengue Hospital-based Study in Nicaragua were reviewed and approved by the Institutional Review Boards of the University of California, Berkeley, (Cohort #2010-09-2245; Hospital #2010-06-1649) and the Nicaraguan Ministry of Health (Cohort NIC-MINSA/CNDR-CIRE-09/03/07-008.ver1; Hospital NIC-MINSA/CNDR-CIRE-01/10/06-13.Ver. 14). Parents or legal guardian of the subjects enrolled in these studies provided written informed consent, and participants 6 years of age and older provided assent. Study population (i) Study enrollment took place at Hospital Infantil Manuel de Jesns Rivera, the national pediatric reference hospital. Children between 6 months and 14 years of age suspected of DENV infection (<7 days since onset of symptoms) were eligible to participate in the hospital study, as described previously. Laboratory-confirmed cases were classified by disease severity according to the 1997 WHO guidelines using a computerized algorithm that compiled all clinical data meeting all criteria for dengue fever (DF), dengue hemorrhagic fever (DHF), or dengue shock syndrome (DSS). Plasma samples were collected in the acute (days 1 to 6 of illness) and convalescent (days 14 to 28 post-onset of symptoms) phases, as well as 3, 6, 12, and 18 months after illness. (ii) The Pediatric Dengue Cohort Study is an ongoing prospective dengue cohort study that follows approximately 3,700 children ages 2-14 in District II of Managua, Nicaragua. Healthy annual blood samples collected from 5 participants from year 1 through 4 post-primary DENV1 infection were used.

DENV-immune sera and immune cells: In the Dengue Cohort Study, DENV infection was identified by serotype-specific RT-PCR for detection of viral RNA, isolation of DENV on C6/36 cells, and/or seroconversion by IgM enzyme-linked immunosorbent assay (ELISA) or a ≥4-fold increase in total serum antibody titer as measured by inhibition ELISA in paired acute- and convalescent-phase samples. In the hospital study, primary dengue cases were determined by inhibition ELISA, where antibody titers of <2,560 in days 14-28 post-onset of symptoms (early convalescent phase) defined primary infection status. In the cohort study, primary infection with DENV was detected by seroconversion (a titer of <1:10 to ≥1:10 as determined by inhibition ELISA) in paired consecutive annual samples.

Virus, rE and rEDIII ELISA: To evaluate if the oligomeric state of the E protein influences the binding efficiency of the mAbs, we subjected the mAbs to an antigen-capture ELISA using DENV3 recombinant E (rE) proteins. DENV rE proteins exist in a concentration- and temperature-dependent monomer-to-dimer equilibrium (PMID:29678884). At physiological conditions, rE is mainly present as a monomer ($rE^M$). Stable DENV3 homodimers ($rE^D$) were generated by introducing a disulfide interaction at the EDII-dimer interface (A257C). $Ni^{2+}$-coated ELISA plates (Pierce Thermo) were coated with 5 ng/µL DENV3 $rE^M$ or $rE^D$ for 1 hour at 37° C. Next, the plates were blocked with TBS+0.05% Tween-20+3% skim milk for 1 hour at 37° C. Plates subsequently were washed three times with TBS+0.2% Tween-20 and incubated with serially diluted mAb (2-0.015 ng/µL) for 1 hour at 37° C. Next, plates were washed and incubated with 1:2,500 diluted alkaline-phosphatase (AP) conjugated anti-human IgG (Sigma) for 45 minutes at 37° C. After washing, wells were developed with AP substrate (Sigma) and absorbance was measured at 405 nm wavelength.

Cell lines and viruses: Vero-81 cells (ATCC #CCL-81) were maintained in Dulbecco's modified Eagle's/Ham's F-12 50/50 Mix (DMEM/F-12 50/50) supplemented with non-essential amino acids (NEAA), glutamine and sodium bicarbonate (Vero cell medium) at 37° C. C6/36 cells (ATCC CRL-1660) were maintained in Gibco minimal essential medium (MEM) supplemented with 1% NEAA at 32° C. Both media were supplemented with 5% fetal bovine serum (FBS) and penicillin/streptomycin antibiotics. The rDENV1 clone is based on DENV strain West Pac 74, the rDENV2 clone is based on DENV strain S16803, the rDENV3 clone is based on a Sri Lankan 1989 DENV strain and the DENV4 molecular clone was based on the sequence of Sri Lankan DENV strain 1992a.

Generation of the rDENV3/1and rDENV1/3 recombinant virus panels: A four-component cDNA cloning system was used in which the DENV genome is divided into four segments that can be replicated separately as plasmids in *Escherichia coli* cells. Purified plasmids are cut with designated restriction enzymes to yield unique type IIS restriction endonuclease cleavage sites that can be ligated simultaneously to yield full-length DENV genome cDNA. A built-in T7 site is used to generate RNA, which is electroporated into C6/36 or Vero-81 cells to recover virus. Virus harvested from medium is subsequently passaged and sequence verified. To generate several additional chimeric rDENV3/1 viruses, we systematically increased the numbers and/or locations of amino acid residues from EDI and EDIII that were transplanted into DENV3 from DENV1. The viruses were designed to gain DENV1 1F4 and 14c10 hmAb neutralizing epitopes, while differentially preserving the DENV3-specific hmAb 5J7 neutralizing epitope, allowing us to measure loss of neutralization with the new panel of DENV3 hmAb. As a result of our quadripartite infectious clone design, all changes were isolated to the A and B fragments of the DENV3 genome backbone. cDNAs encoding E proteins incorporating three increasing sizes of the DENV1 ED1/EDIII transplant were synthesized (BioBasic, Buffalo, N.Y.) and incorporated into three different DENV3 fully assembled DNA genomes and transcribed. Then, the genome-length RNAs were electroporated into Vero-81 cells to generate a panel of viable recombinant rDENV3/1 viruses. Recombinant viruses were subjected to full-length sequencing to demonstrate the presence of appropriate subsets of mutations.

We also synthetically reconstructed two gain-of-function DENV1/3 recombinant chimeras. We replaced all of the varying surface residues in the ED1 of our DENV1 ic with corresponding residues from DENV3 (DENV1/3 ED1-A). In parallel, we constructed a second chimera in which the varying residues in the surface and interior of the ED1 of DENV1 were replaced with DENV3 residues (rDENV1/3 EDI-B). Both viruses were viable and sequence confirmed, allowing for systematic measures of gain-of-function neutralization assays with the new panel of DENV hmAb.

Generation of DENV3 genotype III/IV domain swap virus panel: Infectious clones DENV3 GIV with GIII EDI, DENV3 GIV with GIII EDII, DENV3 GIV with GIII EDIII, DENV3 GIII with GIV EDI, DENV3 GIII with GIV EDII, and DENV3 GIII with GIV EDIII were constructed similarly, as above. We substituted residues in EDI, EDII or EDIII from our DENV3 Puerto Rico genotype IV ic into our Sri Lanka 89 genotype III ic or vice versa using the quadripartite system described above and electroporated into C6/36 or Vero cells. All six viruses were viable and sequence confirmed.

Vero cell titration and focus assays: For viral titrations, viral stocks were diluted 10-fold serially in Vero medium supplemented with 2% heat-inactivated fetal bovine serum (HI-FBS; Hyclone Defined) and 1× antibiotic. The inoculum was added to Vero-81 cells that were seeded into a 96 well plate ($2\times10^4$ cells/well) the previous day and incubated at 37° C. for 1 hour, then overlaid with overlay medium (Opti-MEM I Grand Island, N.Y., with 1% methyl cellulose and 2% heat-inactivated FBS). Viral foci were detected at 44 to 48 h after infection, following fixation/permeabilization with 10% buffered formalin/0.01% saponin using primary murine mAbs 2H2 and 4G2 and secondary horseradish peroxidase (H1RP)-conjugated goat anti-mouse IgG (Sigma), followed by TrueBlue substrate (KPL). Number and size of foci were analyzed with a CTL Immunospot instrument.

Vero cell neutralization assays: Neutralization on Vero-81 cells has been described previously (Gallichotte et al., 2015). Briefly, monolayers of Vero-81 cells in 96-well plates were inoculated with a virus and antibody or serum mix that had been incubated for 1 h at 37° C. to allow for Ab:virion binding. Following a 1 hr incubation on cells at 37° C. for infection, cells and inoculum were overlaid with overlay medium. Viral foci were detected at 44 to 48 h after infection, following fixation/permeabilization with 10% buffered formalin/0.01% saponin using primary mAbs 2H2 and 4G2 (Swanstrom et al., 2016) and secondary horseradish peroxidase (HRP)-conjugated goat anti-mouse IgG (Sigma), followed by TrueBlue substrate (KPL). Numbers of foci were analyzed with an Immunospot Analyzer instrument (Cellular Technology Limited).

Quantification and statistical analysis: Statistical analysis was performed using Prism 5.0 (GraphPad, La Jolla, Calif.). Variable slope sigmoidal dose-response curves are calculated with top or bottom restraints of 100 or 0, respectively. $IC_{50}$ is the concentration of antibody that neutralizes 50% of the virus being tested.

Example 2: New Antigenic Epitopes on Dengue Virus Serotype 3

Four serotypes (1-4) of dengue virus (DENV) circulate in human populations, and immunity to one serotype does not confer long-lasting immunity to the others. Rather, pre-existing DENV immunity may actually increase the risk of severe dengue after exposure to a second serotype. The possibility of antibody-mediated enhancement has complicated vaccine development because of the need to induce robust immunity to all 4 serotypes simultaneously. After a primary infection, type-specific (TS) antibodies to individual serotypes of DENV is thought to be associated with robust, life-long homotypic protection, but the full repertoire of primary neutralizing antibody epitopes in each DENV serotype remains incomplete. Currently, the only DENV3 TS neutralizing human monoclonal antibody (mAb) is 5J7, which recognizes a complex quaternary epitope spanning 3 monomers of the envelope (E) glycoprotein. Importantly, several studies in natural DENV-infected cohorts suggest only a fraction of the polyclonal response targets the 5J7 epitope and there are additional neutralizing epitopes. To test this hypothesis, memory B cells from DENV3 infected individuals were immortalized from a cohort in Nicaragua. New DENV3 TS neutralizing mAbs were identified that do not compete with 5J7 in competition assays. A panel of four chimeric DENV3/1 viruses was designed containing increasingly larger transplants of the DENV1 specific 1F4 and 14c10 epitopes into the DENV3 E protein along with chimeric DENV1/3 viruses containing increasing portions of domain I of DENV3 transplanted into DENV1. Using the panels of DENV3/1 and DENV1/3 chimeras along with an existing panel of five DENV3 genotype E protein swaps, new human mAbs were mapped to four distinct areas of the E protein. When tested in mice, some of the new mAbs were highly protective of challenge with DENV3. These findings provide new insights into the mechanism of DENV3 neutralization and will lead to assays for defining the primary neutralizing epitopes associated with DENV3 protective immunity following natural infection or vaccination.

The dengue virus E glycoprotein assembles as three parallel homodimers which form a raft. 30 rafts cover the surface of the virus. The epitope of 5J7 spans three monomers and is the only characterized human neutralizing DENV3-specific epitope. A chimeric DENV4/3 virus, containing the 5J7 epitope transplanted into a DENV4 backbone, was used to determine the portion of primary DENV3 sera that contains antibodies that target the 5J7 epitope. It was found that 5J7 is not an immunodominant epitope.

Memory B cells were immortalized post DENV3 infection. Recovered hmAbs were screened by ELISA. Fifteen DENV3-specific neutralizing hmAbs were recovered. None of the hmAbs neutralized the DENV4/3 M16 virus which carries the 5J7 epitope on a DENV4 backbone.

FIGS. 1A-1D show chimeric DENV3/1 viruses with transplants (enlarged spheres) from DENV1 1F4+14c10 epitopes into a DENV3 backbone. Substituted amino acids are shown in FIG. 1F. All DENV3/1 chimeras were neutralized by hmAbs 1F4 and 14c10. Only DENV3/1C retained 5J7 neutralization (FIG. 1G). All new DENV3 specific hmAbs were tested for their ability to neutralize the 4 DENV3/1 chimeras in addition to parental viruses in a Vero-81 micro-neut assay. Ten of the hmAbs failed to neutralize any of the chimeras, indicating their epitopes lie within the smallest common transplanted area, likely in domain I (classified as Group I). A subset of hmAbs neutralized all DENV3/1 chimeras indicating their epitopes lie outside of the transplanted areas, likely in domain II (classified as Group II). Two hmAbs neutralized only the smaller chimeras and may use domain III (classified as Group III).

FIGS. 2A-2B show DENV1/3 chimeric viruses with DENV3 surface residues (DENV1/3 A) or surface plus substructure residues (DENV1/3 B) of domain I transplanted into a DENV1 backbone. Transplanted residues are shown in blue—top and side views. Substituted amino acids are shown in FIG. 2D. 9 of the 10 hmAbs that mapped to domain I showed gain-of-function, neutralizing both DENV1/3 chimeras, indicating that the epitopes for these hmAbs are in domain I of DENV3. Interestingly, a subset of hmAbs showed a distinct preference for DENV3/1 B over DENV3/1 A, indicating substructure residues and topology are important for these epitopes. Vero-81 micro-neut assays were performed in duplicate.

FIGS. 3A and 4C show representations of DENV3 Susceptible-Genotype III and Resistant-Genotype IV, as well as DENV3 Genotype IV with E domain I, II, or III changed to Genotype III. Black spheres are changed residues. Amino acid changes and domains are shown in the top table of FIG. 4C. Group I hmAbs showed gain-of-function when EDI was G-III. Group II mAbs showed gain-of-function when EDII was G-III. Group III showed gain-of-function when EDIII was G-III. Vero-81 micro-neut assays were performed in duplicate.

To test in vivo protection against DENV3 challenge, AGM129 mice were given 50 ug of hmAb IP prior to challenge with 5×10⁶ pfu DENV3 and normalized to GAPDH. HmAbs mapping to all four epitopes were protective against challenge in mice.

Antigenic mapping of viruses is important both to diagnostics and evaluation of immunity as well as vaccine design and efficacy. This study identified additional DENV3-specific neutralizing hmAbs. Panels of chimeric DENV3 and DENV1 were used to map the area of the E-glycoprotein targeted by each hmAb. Thirteen of the 15 hmAbs were mapped by gain-of-function to domains of interaction. While exact epitopes cannot be gleaned from this mapping approach alone, the functional epitope for each antibody neutralization phenotype is defined. This study identified five additional antigenically targeted areas of the E glycoprotein.

Example 3: Additional DENV1/3 Chimeras

The following additional DENV 1/3 chimeras were generated according to the methods as described herein.

In these chimeras, different residues of the domain II and I-II hinge region of DENV3 E glycoprotein were swapped into the wildtype DENV1 WestPac '74 E glycoprotein. FIG. 5 indicates the substitutions made against the wildtype DENV1 strain, wherein "E_of_DENV1_West_Pac_'74-DENV3_Domain_2_with DV1 hinge" is identified as DENV1/3-C, "E_of_DENV1_West Pac_'74-DENV3_Domain_2 with DV1 hinge bigger" is identified as DENV1/3-D, "E_of_DENV1_West_Pac_'74-DENV3_Domain_2_+hinge+Q46" is identified as DENV1/3-E, and "E_of_DENV1_West_Pac_'74-DENV3_Domain_2_+hinge w DV1 L46" is identified as DENV1/3-F. The relevant amino acid of DENV3 in each position of the sequences is indicated in the bottom row. These E glycoprotein chimeras may interact with a chimeric prM protein comprising one or more of the following substitutions, wherein the numbering is based on the reference amino acid sequence of a prM protein of dengue virus serotype 1 (DENV1) identified below: T5S, G7D, H11R, S15G, Q17N, S28A, A29S, V31I, L44M, E46D, M49L, R55H, T59V, D61E, V64I, A70L, E72S, S81N, T83A, L101M, E104D, and/or E108Q.

```
>prM_DV1_WP74
                                        (SEQ ID NO: 15)
FHLTTRGGEPHMIVSKQERGKSLLFKTSAGVNMCTLIAMDLGELCEDT

MTYKCPRITETEPDDVDCWCNATETWVTYGTCSQTGEHRRDKRSVALA

PHVGLGLETRTETWMSSEGAWKQIQKVETWALRHPGFTVIALFLAHAI

GTSITQKGIIFILLMLVTPSMA
```

Example 4: Additional DENV1/3 Chimeras

The additional DENV 1/3 chimeras shown below were generated according to the methods as described herein.

In these chimeras, different residues of the domain III region of DENV3 E glycoprotein were swapped into the wildtype DENV1 WestPac '74 E glycoprotein. FIG. 6A indicates the substitutions made against the wildtype DENV1 strain. FIG. 6B indicates positions of substitutions in PyMOL representation.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented

TABLE 1

Dengue Chimeric Viruses

| Name | Recombinant Virus Backbone | DENV3 5J7 Neut | DENV1 1F4 Neut | AA changes | Epitope Transplant | Neutralized by hmAB |
|---|---|---|---|---|---|---|
| DENV4/3 M16 | DENV4 Baric genotype I | +++ | – | 36 aa | 5J7 DENV3 | 5J7 |
| DENV3/1 EDI A | DENV3 Baric genotype III | – | +++ | 23 aa | 1F4 DENV1 | 5J7 |
| DENV3/1 EDI B | DENV3 Baric genotype III | – | +++ | 23 aa | 1F4 + 14c10 DENV1 | |
| DENV3/1 EDI/III C | DENV3 Baric genotype III | +++ | +++ | 35 aa | 1F4 + 14c10 DENV1 | 5J7 |
| DENV3/1 EDI/III D | DENV3 Baric genotype III | – | +++ | 37 aa | 1F4 + 14c10 DENV1 | |
| DENV1/3 EDI A | DENV1 Baric | – | – | 18 aa | EDI surface aa DENV3 | |
| DENV1/3 EDI B | DENV1 Baric | – | – | 22 aa | EDI all aa DENV3 | |

TABLE 2

Additional Dengue Chimeric Viruses

| Chimera name | Recombinant DENV3 Baric virus backbone | Envelope domain (ED) swap | No. of AA changes |
|---|---|---|---|
| DENV3 G-III | GIII Sri Lanka | None | 0 |
| DENV3 G-IV | GIV Puerto Rico | None | 0 |
| DENV3 GIV with G-III EDI | GIV Puerto Rico | I | 9 |

TABLE 2-continued

Additional Dengue Chimeric Viruses

| Chimera name | Recombinant DENV3 Baric virus backbone | Envelope domain (ED) swap | No. of AA changes |
|---|---|---|---|
| DENV3 GIV with G-III EDII | GIV Puerto Rico | II | 9 |
| DENV3 GIV with G-III EDIII | GIV Puerto Rico | III | 6 |
| DENV3 GIII with G-IV EDI | GIII Sri Lanka | I | 8 |

TABLE 2-continued

Additional Dengue Chimeric Viruses

| Chimera name | Recombinant DENV3 Baric virus backbone | Envelope domain (ED) swap | No. of AA changes |
|---|---|---|---|
| DENV3 GIII with G-IV EDII | GIII Sri Lanka | II | 10 |
| DENV3 GIII with G-IV EDIII | GIII Sri Lanka | III | 6 |

SEQUENCES

```
>E_pro_DENV3_3001_baric (DENV3 reference seq)
MRCVGIGNRDFVEGLSGATWVDVVLEHGGCVTTMAKNKPTLDIELQKTEATQLATLRKLCIEGKITNITTDSRCPTQGE
AVLPEEQDQNYVCKHTYVDRGWGNGCGLFGKGSLVTCAKFQCLEPIEGKVVQYENLKYTVIITVHTGDQHQVGNETQGV
TAEITPQASTTEAILPEYGTLGLECSPRTGLDFNEMILLTMKNKAWMVHRQWFFDLPLPWTSGATTETPTWNRKELLVT
FKNAHAKKQEVVVLGSQEGAMHTALTGATEIQNSGGTSIFAGHLKCRLKMDKLELKGMSYAMCTNTFVLKKEVSETQHG
TILIKVEYKGEDAPCKIPFSTEDGQGKAHNGRLITANPVVTKKEEPVNIEAEPPFGESNIVIGIGDNALKINWYKKGSS
IGKMFEATARGARRMAILGDTAWDFGSVGGVLNSLGKMVHQIFGSAYTALFSGVSWVMKIGIGVLLTWIGLNSKNTSMS
FSCIAIGIITLYLGAWQA (SEQ ID NO: 1)

>E_pro_DV1 (DENV1 reference seq)
MRCVGIGNRDFVEGLSGATWVDVVLEHGSCVTTMAKDKPTLDIELLKTEVTNPAVLRKLCIEAKISNTTTDSRCPTQGE
ATLVEEQDTNFVCRRTFVDRGWGNGCGLFGKGSLITCAKFKCVTKLEGKIVQYENLKYSVIVTVHTGDQHQVGNETTEH
GTIATITPQAPTSEIQLTDYGALTLDCSPRTGLDFNEMVLLTMKKKSWLVHKQWFLDLPLPWTSGASTSQETWNRQDLL
VTFKTAHAKKQEVVVLGSQEGAMHTALTGATEIQTSGTTTIFAGHLKCRLKMDKLTLKGMSYAMCTGSFKLEKEVAETQ
HGTVLVQVKYEGTDAPCKIPFSSQDEKGVTQNGRLITANPIVTDKEKPVNIEAEPPFGESYIVVGAGEKALKLSWFKKG
SSIGKMEEATARGARRMAILGDTAWDEGSIGGVFTSVGKLIHQIFGTAYGVLFSGVSWTMKIGIGILLTWLGLNSRSTS
LSMTCIAVGMVTLYLGVMVQA (SEQ ID NO: 2)

DENV 3/1 Chimeras

>Epro_3001_DV3-1match_TDV_large ("3/1 large" also referred to as "3/1 B")
MRCVGIGNRDFVEGLSGATWVDVVLEHGGCVTTMAKNKPTLDIELLKTEVTQPAVLRKLCIEGKITNITTDSRCPTQGE
AVLPEEQDQNYVCKHTYVDRGWGNGCGLFGKGSLVTCAKFQCLEPIEGKVVQYENLKYSVIITVHTGDQHQVGNETTEH
GTIATITPQAPTSEIQLTDYGALGLECSPRTGLDFNEMILLTMKNKAWMVHRQWFFDLPLPWTSGATTETPTWNRKELL
VTFKNAHAKKQEVVVLGSQEGAMHTALTGATEIQTSGTTTIFAGHLKCRLKMDKLELKGMSYAMCTNTFVLKKEVSETQ
HGTILIKVEYKGEDAPCKIPFSTEDGQGKAHNGRLITANPVVTKKEEPVNIEAEPPFGESNIVIGIGEKALKINWYKKG
SSIGKMFEATARGARRMAILGDTAWDFGSVGGVLNSLGKMVHQIFGSAYTALFSGVSWVMKIGIGVLLTWIGLNSKNTS
MSFSCIAIGIITLYLGAVV (SEQ ID NO: 3)

>Epro_DV3-1_1F4_14c10_5J7_whole ("3/1 whole + 5J7" also referred to as "3/1 C")
MRCVGIGNRDFVEGLSGATWVDVVLEHGGCVTTMAKNKPTLDIELLKTEATQLATLRKLCIEGKITNITTDSRCPTQGE
AVLPEEQDQNYVCKHTYVDRGWGNGCGLFGKGSLVTCAKFQCLEPIEGKVVQYENLKYSVIVTVHTGDQHQVGNETTEH
GTIATITPQAPTSEIQLTDYGALTLDCSPRTGLDFNEMILLTMKNKAWMVHRQWFFDLPLPWTSGATTETPTWNRKELL
VTFKNAHAKKQEVVVLGSQEGAMHTALTGATEIQTSGTTTIFAGHLKCRLKMDKLTLKGMSYAMCTGSFKLKKEVSETQ
HGTILIKVKYEGTDAPCKIPFSTEDGQGKAHNGRLITANPVVTKKEEPVNIEAEPPFGESYIVVGAGEKALKLSWYKKG
SSIGKMFEATARGARRMAILGDTAWDFGSVGGVLNSLGKMVHQIFGSAYTALFSGVSWVMKIGIGVLLTWIGLNSKNTS
MSFSCIAIGIITLYLGAVV (SEQ ID NO: 4)

>Epro_DV3-1_1F4_14c10_whole ("3/1 whole - 5J7" also referred to as "371 D")
MRCVGIGNRDFVEGLSGATWVDVVLEHGGCVTTMAKNKPTLDIELLKTEATNPATLRKLCIEGKITNITTDSRCPTQGE
AVLPEEQDQNYVCKHTYVDRGWGNGCGLFGKGSLVTCAKFQCLEPIEGKVVQYENLKYSVIVTVHTGDQHQVGNETTEH
GTIATITPQAPTSEIQLTDYGALTLDCSPRTGLDFNEMILLTMKNKAWMVHRQWFFDLPLPWTSGATTETPTWNRKELL
VTFKNAHAKKQEVVVLGSQEGAMHTALTGATEIQTSGTTTIFAGHLKCRLKMDKLTLKGMSYAMCTGSFKLKKEVSETQ
HGTILIKVKYEGTDAPCKIPFSTEDGQGKAHNGRLITANPVVTKKEEPVNIEAEPPFGESYIVVGAGEKALKLSWYKKG
SSIGKMFEATARGARRMAILGDTAWDFGSVGGVLNSLGKMVHQIFGSAYTALFSGVSWVMKIGIGVLLTWIGLNSKNTS
MSFSCIAIGIITLYLGAW (SEQ ID NO: 5)

DENV 1/3 Chimeras

>DENV1-3-A
MRCVGIGNRDFVEGLSGATWVDVVLEHGSCVTTMAKDKPTLDIELQKTEVTQPAVLRKLCIEAKISNTTTDSRCPTQGE
ATLVEEQDTNFVCRRTFVDRGWGNGCGLFGKGSLITCAKFKCVTKLEGKIVQYENLKYTVIVTVHTGDQHQVGNETQSH
GVTAEITPQAPTTEAILPEYGALTLDCSPRTGLDFNEMVLLTMKKKSWLVHKQWFLDLPLPWTSGASTSQETWNRQDLL
VTFKTAHAKKQEVVVLGSQEGAMHTALTGATEIQNSGGTSIFAGHLKCRLKMDKLTLKGMSYVMCTGSFKLEKEVAETQ
HGTVLVQVKYEGTDAPCKIPFSSQDEKGVTQNGRLITANPIVTDKEKPVNIEAEPPFGESYIVVGAGDNALKLSWFKKG
SSIGKMEEATARGARRMAILGDTAWDFGSIGGVFTSVGKLIHQIFGTAYGVLFSGVSWTMKIGIGILLTWLGLNSRSTS
LSMTCIAVGMVTLYLGVMVQA (SEQ ID NO: 6)

YDENV1-3-B
MRCVGIGNRDFVEGLSGATWVDVVLEHGSCVTTMAKDKPTLDIELQKTEVTNPAVLRKLCIEAKISNTTTDSRCPTQGE
ATLVEEQDTNFVCRRTFVDRGWGNGCGLFGKGSLITCAKFKCVTKLEGKIVQYENLKYTVIITVHTGDQHQVGNETQGV
TAEITPQASTTEAILPEYGTLGLECSPRTGLDFNEMVLLTMKKKSWLVHKQWFLDLPLPWTSGASTSQETWNRQDLLVT
FKTAHAKKQEVVVLGSQEGAMHTALTGATEIQNSGGTSIFAGHLKCRLKMDKLELKGMSYVMCTGSFKLEKEVAETQHG
```

SEQUENCES

```
TVLVQVKYEGTDAPCKIPFSSQDEKGVTQNGRLITANPIVTDKEKPVNIEAEPPFGESYIVVGAGEKALKLSWFKKGSS
IGKMFEATARGARRMAILGDTAWDFGSIGGVFTSVGKLIHQIFGTAYGVLFSGVSWTMKIGIGILLTWLGLNSRSTSLS
MTCIAVGMVTLYLGVMVQA (SEQ ID NO: 7)

>E_of_DENV1_West_Pac_'74-DENV3_Domain_2_with DV1 hinge "DENV1/3-C"
MRCVGIGNRDFVEGLSGATWVDVVLEHGSCVTTMAKDKPTLDIELLKTEVTNLATLRKLCIEGKITNITTDSRCPTQGE
AVLPEEQDQNYVCKHTYVDRGWGNGCGLFGKGSLVTCAKFQCLEPIEGKVVQYENLKYSVIVTVHTGDQHQVGNETTEH
GTIATITPQAPTSEIQLTDYGALTLDCSPRTGLDFNEMILLTMKNKAWMVHRQWFFDLPLPWTSGATTETPTWNRKELL
VTFKNAHAKKQEVVVLGSQEGAMHTALTGATEIQNSGTTTIFAGHLKCRLKMDKLTLKGMSYVMCTGSFKLEKEVAETQ
HGTVLVQVKYEGTDAPCKIPFSSQDEKGVTQNGRLITANPIVTDKEKPVNIEAEPPFGESYIVVGAGEKALKLSWFKKG
SSIGKMFEATARGARRMAILGDTAWDFGSIGGVFTSVGKLIHQIFGTAYGVLFSGVSWTMKIGIGILLLTWLGLNSRSTS
LSMTCIAVGMVTLYLGVMVQA (SEQ ID NO: 8)

>E_of_DENV1_West_Pac_'74-DENV3_Domain_2_with DV1 hinge bigger "DENV1/3-D"
MRCVGIGNRDFVEGLSGATWVDVVLEHGSCVTTMAKDKPTLDIELLKTEVTNPAVLRKLCIEGKITNITTDSRCPTQGE
AVLPEEQDQNYVCKHTYVDRGWGNGCGLFGKGSLVTCAKFQCLEPIEGKIVQYENLKYSVIVTVHTGDQHQVGNETTEH
GTIATITPQAPTSEIQLTDYGALTLDCSPRTGLDFNEMVLLTMKKKSWLVHKQWFFDLPLPWTSGATTETPTWNRKELL
VTFKNAHAKKQEVVVLGSQEGAMHTALTGATEIQTSGTTTIFAGHLKCRLKMDKLTLKGMSYVMCTGSFKLEKEVAETQ
HGTVLVQVKYEGTDAPCKIPFSSQDEKGVTQNGRLITANPIVTDKEKPVNIEAEPPFGESYIVVGAGEKALKLSWFKKG
SSIGKMEEATARGARRMAILGDTAWDFGSIGGVFTSVGKLIHQIFGTAYGVLFSGVSWTMKIGIGILLLTWLGLNSRSTS
LSMTCIAVGMVTLYLGVMVQA (SEQ ID NO: 9)

>E_of_DENV1_West_Pac_'74-DENV3_Domain_2_ + hinge + Q46 "DENV1/3-E"
MRCVGIGNRDFVEGLSGATWVDVVLEHGSCVTTMAKDKPTLDIELLKTEATQLATLRKLCIEGKITNITTDSRCPTQGE
AVLPEEQDQNYVCKHTYVDRGWGNGCGLFGKGSLVTCAKFQCLEPIEGKVVQYENLKYSVIVTVHTGDQHQVGNETTEH
GTIATITPQAPTSEIQLTDYGALTLDCSPRTGLDFNEMILLTMKNKAWMVHRQWFFDLPLPWTSGATTETPTWNRKELL
VTFKNAHAKKQEVVVLGSQEGAMHTALTGATEIQNSGGTSIFAGHLKCRLKMDKLTLKGMSYVMCTGSFKLEKEVAETQ
HGTVLVQVKYEGTDAPCKIPFSSQDEKGVTQNGRLITANPIVTDKEKPVNIEAEPPFGESYIVVGAGEKALKLSWFKKG
SSIGKMFEATARGARRMAILGDTAWDFGSIGGVFTSVGKLIHQIFGTAYGVLFSGVSWTMKIGIGILLLTWLGLNSRSTS
LSMTCIAVGMVTLYLGVMVQA (SEQ ID NO: 10)

>E_of_DENV1_West_Pac_'74-DENV3_Domain_2_ + hinge w DV1 L46 "DENV1/3-F"
MRCVGIGNRDFVEGLSGATWVDVVLEHGSCVTTMAKDKPTLDIELLKTEATQLATLRKLCIEGKITNITTDSRCPTQGE
AVLPEEQDQNYVCKHTYVDRGWGNGCGLFGKGSLVTCAKFQCLEPIEGKVVQYENLKYSVIVTVHTGDQHQVGNETTEH
GTIATITPQAPTSEIQLTDYGALTLDCSPRTGLDFNEMILLTMKNKAWMVHRQWFFDLPLPWTSGATTETPTWNRKELL
VTFKNAHAKKQEVVVLGSQEGAMHTALTGATEIQNSGGTSIFAGHLKCRLKMDKLTLKGMSYVMCTGSFKLEKEVAETQ
HGTVLVQVKYEGTDAPCKIPFSSQDEKGVTQNGRLITANPIVTDKEKPVNIEAEPPFGESYIVVGAGEKALKLSWFKKG
SSIGKMFEATARGARRMAILGDTAWDFGSIGGVFTSVGKLIHQIFGTAYGVLFSGVSWTMKIGIGILLLTWLGLNSRSTS
LSMTCIAVGMVTLYLGVMVQA (SEQ ID NO: 11)
```

Sequences for prM protein in DENV1/3 EDII (domain 2) chimeras DENV/1/3 C-F. All use the same chimeric prM below.

>prM_DV1_WP74

(SEQ ID NO: 15)

FHLTTRGGEPHMIVSKQERGKSLLFKTSAGVNMCTLIAMDLGELCEDTM

TYKCPRITETEPDDVDCWCNATETWVTYGTCSQTGEHRRDKRSVALAPH

VGLGLETRTETWMSSEGAWKQIQKVETWALRHPGFTVIALFLAHAIGTS

ITQKGIIFILLMLVTPSMA

>prM_of_DENV1_West_Pac_'74-DENV3_Dom_2_s
Chimeric prM (SEQ ID NO: 17)

FHLTSRDGEPRMIVGKNERGKSLLFKTASGINMCTLIAMDLGEMCDDTL

TYKCPHITEVEPEDIDCWCNLTSTWVTYGTCNQAGEHRRDKRSVALAPH

VGMGLDTRTQTWMSSEGAWKQIQKVETWALRHPGFTVIALFLAHAIGTS

ITQKGIIFILLMLVTPSMA

>prM_DV3_3001

(SEQ ID NO: 16)

FHLTSRDGEPRMIVGKNERGKSLLFKTASGINMCTLIAMDLGEMCDDTV

TYKCPHITEVEPEDIDCWCNLTSTWVTYGTCNQAGEHRRDKRSVALAPH

VGMGLDTRTQTWMSAEGAWRQVEKVETWALRHPGFTILALFLAHYIGTS

-continued

LTQKWIFILLMLVTPSMT

Additional DENV 1/3 Chimeras

Eprotein DENV1/3 domain 3 is DENV3 except amino acids E342, K343 and T346 are DENV1
>E_pro_DV1-3_domain3_A346T_3aaDV1

(SEQ ID NO: 12)

MRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDEK

GKTHNGRLITANPVVTKKEEPVNIEAEPPFGESNIVIGIGDNALKINWF

KKGSSIGKMEEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

Eprotein DENV1/3 domain 3 is DENV3 except amino acids E342 and K343 are DENV1
>E_pro_DV1-3_domain3_354-2 + 5

(SEQ ID NO: 13)

-continued

MRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDEK

GKAHNGRLITANPVVTKKEEPVNIEAEPPFGESNIVIGIGDNALKINWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

Eprotein DENV1/3 domain 3 is DENV3

-continued

>E_pro_DV1-3_domain3_all_DV3

(SEQ ID NO: 14)

MRCVGIGNRDFVEGLSGATWVDVVLEHGSCVTTMAKDKPTLDIELLKTE

VTNPAVLRKLCIEAKISNTTTDSRCPTQGEATLVEEQDTNFVCRRTFVD

RGWGNGCGLFGKGSLITCAKFKCVTKLEGKIVQYENLKYSVIVTVHTGD

QHQVGNETTEHGTIATITPQAPTSEIQLTDYGALTLDCSPRTGLDFNEM

VLLTMKKKSWLVHKQWFLDLPLPWTSGASTSQETWNRQDLLVTFKTAHA

KKQEVVVLGSQEGAMHTALTGATEIQTSGTTTIFAGHLKCRLKMDKLTL

KGMSYAMCTNTFVLKKEVSETQHGTILIKVEYKGEDAPCKIPFSTEDGQ

GKAHNGRLITANPVVTKKEEPVNIEAEPPFGESNIVIGIGDNALKINWF

KKGSSIGKMFEATARGARRMAILGDTAWDFGSIGGVFTSVGKLIHQIFG

TAYGVLFSGVSWTMKIGIGILLTWLGLNSRSTSLSMTCIAVGMVTLYLG

VMVQA

What is claimed is:

1. A chimeric dengue virus E glycoprotein, comprising the following amino acid substitutions wherein the numbering is based on the reference amino acid sequence of an E glycoprotein of dengue virus serotype 3 (DENV3) identified as SEQ ID NO: 1:

T138S, Q156H, V158T, S167P, A171I, I172Q, P174T, E175D, N270T, G273T, S275T, and D382E, and wherein said dengue virus E glycoprotein further comprises an insertion of the amino acid residues T and E between amino acid residues 155 and 156.

2. A chimeric dengue virus E glycoprotein, comprising the following amino acid substitutions wherein the numbering is based on the reference amino acid sequence of an E glycoprotein of dengue virus serotype 3 (DENV3) identified as SEQ ID NO: 1:

(i) Q46L, A50V, L53P, T55V, T138S, Q156H, V158T, T159I, E161T, S167P, T169S, A171I, I172Q, P174T, E175D, T178A, N270T, G273T, S275T, D382E, and N383K;

(ii) Q46L, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L; or (iii) Q46L, Q52N, L53P, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S, and wherein said dengue virus E glycoprotein further comprises an insertion of the amino acid residues T and E between amino acid residues 155 and 156.

3. The chimeric dengue virus E glycoprotein of claim 2, comprising the amino acid sequence of SEQ ID NO:1, wherein said amino acid sequence comprises the following amino acid substitutions:

(i) Q46L, A50V, L53P, T55V, T138S, Q156H, V158T, T159I, E161T, S167P, T169S, A171I, I172Q, P174T, E175D, T178A, N270T, G273T, S275T, D382E, and N383K;

(ii) Q46L, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S; and/or (iii) Q46L, Q52N, L53P, T138S, I141V, Q156H, V158T, T159I, E161T, S167P, T169S, A171I, I172Q, P174T, E175D, T178A, G180T, E182D, N270T, G273T, S275T, E291T, N302G, T303S, V305K, E323K, K325E, E327T, N375Y, I378V, I380A, D382E, N383K, I387L, and N388S, and wherein said dengue virus E glycoprotein further comprises an insertion of the amino acid residues T and E between amino acid residues 155 and 156.

4. The chimeric dengue virus E glycoprotein of claim 3, comprising the amino acid sequence of any one of SEQ ID NOs: 3-5.

5. A chimeric dengue virus E glycoprotein, comprising the following amino acid substitutions wherein the numbering is based on the reference amino acid sequence of an E glycoprotein of dengue virus serotype 1 (DENV1) identified as SEQ ID NO: 2:

(i) L46Q, N52Q, S138T, T156Q, E157S, T160V, I161T, T163E, S171T, I173A, Q174I, T176P, D177E, T272N, T275G, T277S, E384D, and K385N;

(ii) L46Q, S138T, V141I, T156Q, T160V, I161T, T163E, P169S, S171T, I173A, Q174I, T176P, D177E, A180T, T182G, D184E, T272N, T275G, T277S, and T293E, and wherein said dengue virus E glycoprotein further comprises a deletion of the amino acid residues E157 and H158;

(iii) P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, and T272N;

(iv) A63G, S66T, T68I, T81V, V83P, T88Q, F90Y, R93K, R94H, F96Y, I114V, K120Q, V122L, T123E, K124P, L125I, L214F, S225T, S227E, Q228T, E229P, Q234K, D235E, T242N, and T272N;

(v) L46Q, V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S;

(vi) V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D23SE, T242N, T272N, T275G, and T277S;

(vii) V300A, G304N, S305T, K307V, E309K, A313S, V320I, V322I, Q323K, K325E, E327K, T329E, S339T, Q340E, V345K, Q347H, I357V, D360K, K363E, Y377N, V380I, A382I, E384D, K385N, L389I, and S390N;

(viii) V300A, G304N, S305T, K307V, E309K, A313S, V320I, V322I, Q323K, K325E, E327K, T329E, S339T, Q340E, V345K, T346A, Q347H, I357V, D360K, K363E, Y377N, V380I, A382I, E384D, K385N, L389I, and S390N; or (ix) V300A, G304N, S305T, K307V, E309K, A313S, V320I, V322I, Q323K, K325E, E327K, T329E, S339T, Q340E, E342G, K343Q, V345K, T346A, Q347H, I357V, D360K, K363E, Y377N, V380I, A382I, E384D, K385N, L389I, and S390N.

6. The chimeric dengue virus E glycoprotein of claim 5, comprising the amino acid sequence of SEQ ID NO:2, wherein said amino acid sequence comprises the following amino acid substitutions:

(i) L46Q, N52Q, S138T, T156Q, E157S, T160V, I161T, T163E, S171T, I173A, Q174I, T176P, D177E, T272N, T275G, T277S, E384D, and K385N;

(ii) L46Q, S138T, V141I, T156Q, T160V, I161T, T163E, P169S, S171T, I173A, Q174I, T176P, D177E, A180T, T182G, D184E, T272N, T275G, T277S, and T293E, and wherein said dengue virus E glycoprotein further comprises a deletion of the amino acid residues E157 and H158;

(iii) P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, and T272N;

(iv) A63G, S66T, T68I, T81V, V83P, T88Q, F90Y, R93K, R94H, F96Y, I114V, K120Q, V122L, T123E, K124P, L125I, L214F, S225T, S227E, Q228T, E229P, Q234K, D235E, T242N, and T272N;

(v) L46Q, V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S;

(vi) V50A, N52Q, P53L, V55T, A63G, S66T, T68I, T81V, V83P, T88Q, F90Y, R93K, R94H, F96Y, I114V, K120Q, V122L, T123E, K124P, L125I, I129V, V197I, K203N, S205A, L207M, K210R, L214F, S225T, S227E, Q228T, E229P, Q234K, D235E, T242N, T272N, T275G, and T277S;

(vii) V300A, G304N, S305T, K307V, E309K, A313S, V320I, V322I, Q323K, K325E, E327K, T329E, S339T, Q340E, V345K, Q347H, I357V, D360K, K363E, Y377N, V380I, A382I, E384D, K385N, L389I, and S390N;

(viii) V300A, G304N, S305T, K307V, E309K, A313S, V320I, V322I, Q323K, K325E, E327K, T329E, S339T, Q340E, V345K, T346A, Q347H, I357V, D360K, K363E, Y377N, V380I, A382I, E384D, K385N, L389I, and S390N; and/or (ix) V300A, G304N, S305T, K307V, E309K, A313S, V320I, V322I, Q323K, K325E, E327K, T329E, S339T, Q340E, E342G, K343Q, V345K, T346A, Q347H, I357V, D360K, K363E, Y377N, V380I, A382I, E384D, K385N, L389I, and S390N.

7. The chimeric dengue virus E glycoprotein of claim 6 comprising the amino acid sequence of any one of SEQ ID NOs: 6-14.

8. A flavivirus particle or virus like particle (VLP) comprising the E glycoprotein of claim 2.

9. An isolated nucleic acid molecule encoding the E glycoprotein of claim 2.

10. An isolated nucleic acid molecule encoding the flavivirus particle or VLP of claim 8.

11. A population of flavivirus particles comprising the flavivirus particle of claim 8.

12. A composition comprising the E glycoprotein of claim 2, in a pharmaceutically acceptable carrier.

13. A method of producing an immune response to a dengue virus in a subject, comprising administering to the subject an effective amount of the E glycoprotein of claim 2.

14. A method of treating a dengue virus infection in a subject, comprising administering to the subject an effective amount of the E glycoprotein of claim 2.

15. A method of protecting a subject from the effects of dengue virus serotype 1 (DENV1) infection and dengue virus serotype 3 (DENV3) infection, comprising administering to the subject an effective amount of the E glycoprotein of claim 2.

16. A flavivirus particle or virus like particle (VLP) comprising the E glycoprotein of claim 1.

17. An isolated nucleic acid molecule encoding the E glycoprotein of claim 1.

18. An isolated nucleic acid molecule encoding the flavivirus particle or VLP of claim 16.

19. A population of flavivirus particles comprising the flavivirus particle of claim 16.

20. A composition comprising the E glycoprotein of claim 1, in a pharmaceutically acceptable carrier.

21. A method of producing an immune response to a dengue virus in a subject, comprising administering to the subject an effective amount of the E glycoprotein of claim 1.

22. A method of treating a dengue virus infection in a subject, comprising administering to the subject an effective amount of the E glycoprotein of claim 1.

23. A method of protecting a subject from the effects of dengue virus serotype 1 (DENV1) infection and dengue virus serotype 3 (DENV3) infection comprising administering to the subject an effective amount of the E glycoprotein of claim 1.

24. A flavivirus particle or virus like particle (VLP) comprising the E glycoprotein of claim 5.

25. An isolated nucleic acid molecule encoding the E glycoprotein of claim 5.

26. An isolated nucleic acid molecule encoding the flavivirus particle or VLP of claim 24.

27. A population of flavivirus particles comprising the flavivirus particle of claim 24.

28. A composition comprising the E glycoprotein of claim 5, in a pharmaceutically acceptable carrier.

29. A method of producing an immune response to a dengue virus in a subject, comprising administering to the subject an effective amount of the E glycoprotein of claim 5.

30. A method of treating a dengue virus infection in a subject, comprising administering to the subject an effective amount of the E glycoprotein of claim 5.

31. A method of protecting a subject from the effects of dengue virus serotype 1 (DENV1) infection and dengue virus serotype 3 (DENV3) infection comprising administering to the subject an effective amount of the E glycoprotein of claim 5.

* * * * *